US007972870B2

(12) United States Patent
Kufe

(10) Patent No.: US 7,972,870 B2
(45) Date of Patent: Jul. 5, 2011

(54) METHODS AND COMPOSITIONS RELATING TO THE REGULATION OF MUC1 BY HSF1 AND STAT3

(75) Inventor: Donald W. Kufe, Wellesley, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 205 days.

(21) Appl. No.: 12/024,692

(22) Filed: Feb. 1, 2008

(65) Prior Publication Data

US 2009/0092600 A1 Apr. 9, 2009

Related U.S. Application Data

(60) Provisional application No. 60/888,014, filed on Feb. 2, 2007.

(51) Int. Cl.
G01N 33/567 (2006.01)
G01N 33/543 (2006.01)
(52) U.S. Cl. ..................... 436/503; 436/518
(58) Field of Classification Search .................. None
See application file for complete search history.

(56) References Cited

U.S. PATENT DOCUMENTS

| 4,497,796 | A | 2/1985 | Salser et al. ............ 514/44 |
|---|---|---|---|
| 4,522,811 | A | 6/1985 | Eppstein et al. .......... 514/2 |
| 4,675,382 | A | 6/1987 | Murphy ............... 260/112 |
| 4,894,227 | A | 1/1990 | Stevens et al. .......... 424/85.2 |
| 4,963,484 | A | 10/1990 | Kufe ..................... 435/69.3 |
| 5,053,489 | A | 10/1991 | Kufe ..................... 530/350 |
| 5,080,898 | A | 1/1992 | Murphy ............... 424/94.1 |
| 5,380,712 | A | 1/1995 | Ballance et al. .......... 514/12 |
| 5,506,343 | A | 4/1996 | Kufe ................... 530/387.7 |
| 5,530,101 | A | 6/1996 | Queen et al. ........... 530/387.3 |
| 5,565,334 | A | 10/1996 | Kufe et al. ............. 435/69.1 |
| 5,597,457 | A | 1/1997 | Craig et al. ............. 204/165 |
| 5,612,895 | A | 3/1997 | Balaji et al. ............. 702/19 |
| 5,766,833 | A | 6/1998 | Balance et al. .......... 435/69.7 |
| 5,776,427 | A | 7/1998 | Thorpe et al. ........... 424/1.49 |
| 5,790,421 | A | 8/1998 | Osslund ................. 703/2 |
| 5,801,154 | A | 9/1998 | Baracchini et al. ........ 514/44 |
| 5,827,516 | A | 10/1998 | Urban et al. ............ 424/93.21 |
| 5,861,381 | A | 1/1999 | Chambon et al. ......... 514/44 |
| 5,874,415 | A | 2/1999 | Kufe et al. ............. 514/44 |
| 5,965,386 | A | 10/1999 | Kerry-Williams et al. .. 435/69.1 |
| 5,998,148 | A | 12/1999 | Bennett et al. ........... 435/6 |
| 6,004,746 | A | 12/1999 | Brent et al. ............. 435/6 |
| 6,020,363 | A | 2/2000 | Hirano et al. ............ 514/456 |
| 6,054,438 | A | 4/2000 | Taylor-Papadimitriou et al. .................. 514/44 |
| 6,074,841 | A | 6/2000 | Gearing et al. .......... 435/69.1 |
| 6,093,573 | A | 7/2000 | Beamer et al. ........... 436/86 |
| 6,222,020 | B1 | 4/2001 | Taylor-Papadimitriou et al. .................. 530/395 |
| 6,303,302 | B1 | 10/2001 | Rupp et al. ............. 435/6 |
| 6,344,203 | B1 | 2/2002 | Sandrin ................ 424/277.1 |
| 6,589,921 | B2 | 7/2003 | Herrmann et al. ........ 514/456 |
| 6,716,627 | B2 | 4/2004 | Dobie ................. 435/375 |
| 6,716,966 | B1 | 4/2004 | Madiyalakan et al. .... 530/387.1 |
| 7,147,850 | B2 | 12/2006 | Madiyalakan ........... 514/12 |
| 2002/0110841 | A1 | 8/2002 | Kufe .................. 435/7.23 |
| 2003/0235857 | A1 | 12/2003 | Rupp et al. ............ 435/6 |
| 2004/0018181 | A1 | 1/2004 | Kufe et al. ............. 424/93.21 |
| 2004/0166543 | A1 | 8/2004 | Kufe .................. 435/7.23 |
| 2004/0209832 | A1 | 10/2004 | McSwiggen ............ 514/44 |
| 2005/0042209 | A1 | 2/2005 | Kufe et al. ............. 424/93.21 |
| 2005/0053606 | A1* | 3/2005 | Kufe et al. ............. 424/155.1 |
| 2006/0019256 | A1 | 1/2006 | Clarke et al. ........... 435/6 |
| 2007/0105767 | A1* | 5/2007 | Kharbanda et al. ....... 514/12 |
| 2008/0090770 | A1 | 4/2008 | Belmares et al. ........ 514/18 |
| 2008/0286264 | A1* | 11/2008 | Kufe ................. 424/130.1 |

FOREIGN PATENT DOCUMENTS

| EP | 1103623 | 7/1998 |
|---|---|---|
| WO | WO 93/20841 | 10/1993 |
| WO | WO 96/03502 | 2/1996 |
| WO | WO 99/23114 | 5/1999 |
| WO | WO 91/09867 | 7/1999 |
| WO | WO 00/09744 | 2/2000 |
| WO | WO 00/11206 | 3/2000 |
| WO | WO 00/25827 | 5/2000 |
| WO | WO 00/34468 | 6/2000 |
| WO | WO 00/47763 | 8/2000 |
| WO | WO 00/77031 | 12/2000 |
| WO | WO 01/12217 | 2/2001 |
| WO | WO 01/18035 | 3/2001 |
| WO | WO 01/57068 | 8/2001 |
| WO | WO 02/22685 | 3/2002 |
| WO | WO 02/31512 | 4/2002 |
| WO | WO 02/058450 | 8/2002 |
| WO | WO 2003/014303 | 2/2003 |
| WO | WO 2003/088995 | 10/2003 |

(Continued)

OTHER PUBLICATIONS

Skolnick and Fetrow. From genes to protein structure and function: novel applications of computational approaches in the genomic era. Trends in Biotechnology, 2000. vol. 18, pp. 34-39.*
Burgess, Shaheen, Ravera, Jaye, Donohue, and Winkles. Possible dissociation of the heparin binding and mitogenic activities of heparin binding (acidic fibroblast) growth factor-1 from its receptor binding activities by site directed mutagenesis of a single lysine residue. Journal of Cell Biology, 1990. vol. 111, pp. 2129-2138.*
Lazar, Watanabe, Dalton, and Sporn. Transforming growth factor alpha: mutation of aspartic acid 47 and leucine 48 results in different biological activities. Molecular and Cellular Biology, 1988. vol. 8, pp. 1247-1252.*
Ren et al., "MUC1 oncoprotein functions in activation of fibroblast growth factor receptor signaling," Mol. Cancer Res., 4(11): 873-883, 2006.
U.S. Appl. No. 10/486,278, filed Jun. 23, 2004, Reinherz et al.
U.S. Appl. No. 60/308,307, filed Jul. 27, 2001, Kufe.
U.S. Appl. No. 60/502,111, filed Sep. 11, 2003, Jecminek et al.
"MUC-1/X mucin short variant," GenBank Accession No. AAD10856, dated Jun. 5, 2001.

(Continued)

Primary Examiner — Anne M. Gussow
(74) Attorney, Agent, or Firm — Fulbright & Jaworski

(57) ABSTRACT

This invention relates to regulation of cell signaling, cell growth, and more particularly to the regulation of cancer or inflammatory cell growth and/or activation. The invention provides methods of inhibiting interactions between MUC1 and a heat shock factor, method of inhibiting interactions between transcription factors and the MUC1 promoter, and methods of inhibiting MUC1 expression. The invention also provides screening methods for identifying compounds that inhibit the aforementioned interactions. Pharmaceutical compositions containing the identified compounds can be useful in treating cancers and inflammatory conditions.

1 Claim, 8 Drawing Sheets

FOREIGN PATENT DOCUMENTS

| WO | WO 2004/044160 | 5/2004 |
|----|----------------|--------|
| WO | WO 2004/092339 | 10/2004 |

OTHER PUBLICATIONS

"MUC-1/Z mucin short variant," GenBank Accession No. AAD10858, dated Jun. 5, 2001.
"Mucin 1 precursor, non-repetitive splice from Y [validated]-human," GenBank Accession No. S48146, dated Apr. 20, 2000.
Abe et al., "Characterization of cis-acting elements regulating transcription of the human DF3 breat carcinoma-associated antigen (MUC1) gene," *Proc. Natl. Acad. Sci. USA.*, 90:282-286, 1993.
Abe et al., "Identification of a family of high molecular weight tumor-associated glycoproteins," *J. Immun.*, 139:257-261, 1987.
Abe et al., "Sequence Anaylsis of the 5' region of the human DF3 breast carcinoma-associated antigen gene," *Bio. Biophys. Research Comm.*, 165:644-649, 1989.
Abe et al., "Sodium butyrate induction of milk-related antigens in human MCF-7 breast carcinoma cells," *Cancer Res.*, 44:4574-4577, 1984.
Abe et al., "Structural analysis of the DF3 human breat carcinoma-associated protein," *Cancer Res.*, 49:2834-2839, 1989.
Abe et al., "Transcriptional regulation of DF3 gene expression in human MCF-7 breast carcinoma cells," *J. Cell. Physio.*, 143:226-231, 1990.
Adams and Cory, "The Bcl-2 Protein Family: Arbiters of Cell Survival," *Science*, 281:1322-1326, 1998.
Agrawal and Kandimalla, "Antisense therapeutics: is it as simple as complementary base recognition?" *Molecular Medicine Today*, 6:72-81, 2000.
Akagi et al., "CA19-9 epitope a possible marker for MUC-1/Y protein," *Int. J. Oncol.*, 18:1085-1091, 2001.
Alfieri et al., "Activation of heat-shock transcription factor 1 by hypertonic shock in 3T3 cells," *Biochem. J.*, 319:601-606, 1996.
Apostolopoulos et al., "Production of anti-breast cancer monoclonal antibodies using a glutathione-S-transferase-MUC1 bacterial fusion protein," *British J. Cancer.*, 67:713-720, 1993.
Arklie et al., "Differentiation antigens expressed by epithelial cells in the lactating breast are also detectable in breast cancers," *Int. J. Cancer*, 28:23-29, 1981.
Ashkenazi and Dixit, "Apoptosis control by death and decoy receptors," *Curr. Opin. Cell Biol.*, 11:255-260, 1999.
Ashkenazi and Dixit, "Death Receptors: Signaling and Modulation," *Science*, 281:1305-1308, 1998.
Ashkenazi et al., "Safety and antitumor activity of recombinant soluble Apo2 ligand," *J. Clin. Invest.*, 104:155-162, 1999.
Backstom et al., "Recombinant MUC1 mucin with a breast cancer-like O-glycosylation produced in large amounts in Chinese-hamster ovary cells," *Biochemical Journal*, 376:677-686, 2003.
Banerjee, "Omega amino acids in peptide design: incorporation into helices ," *Biopolymers*, 39:769-77, 1996.
Barrett et al., "PLU-1 nuclear protein, which is upregulated in breast cancer, shows restricted expression in normal human adult tissues: a new cancer/testis antigen?," *Int. J. Cancer*, 101:581-588, 2002.
Barry and Sharkey, "Observer reproducibility during computer-assisted planimetric measurements of nuclear features," *Hum. Pathol.*, 16:225-7, 1985.
Barry et al., "Activation of programmed cell death (apoptosis) by cisplatin, other anticancer drugs, toxins and hyperthermia," *Biochemical Pharmacology*, 40:2353-2362, 1990.
Baruch et al., "Preferential expression of novel MUC1 tumor antigen isoforms in human epithelial tumors and their tumor-potentiating function," *Int. J. Cancer*, 71:741-749, 1997.
Baruch et al., "The breast cancer-associated MUC1 gene generates both a receptor and its cognate binding protein," *Cancer Res.*, 59:1552-1561, 1999.
Bass, "The short answer," *Nature*, 411:428-429, 2001.
Batra et al., "Transfection of the human MUC1 mucin gene into a poorly differentiated human pancreatic tumor cell line, Panc1: integration, expression and ultrastructural changes," *J. Cell Science*, 100:841-849, 1991.
Becker et al., "Three-dimensional structure of the Stat3beta homodimer bound to DNA," *Nature*, 394:145-151, 1998.
Bellgrau et al., "A role for CD95 ligand in preventing graft rejection," *Nature*, 377:630-632, 1995.
Berger et al., "Respiratory carcinoma cell lines: MUC genes and glycoconjugates," *American Journal of Respiratory Cell and Molecular Biology*, 20:500-510, 1999.
Bergeron et al., "MAUB is a new mucin antigen associated with bladder cancer," *J. Biol. Chem.*, 271:6933-6940, 1996.
Beusen et al., "Conformational mimicry: synthesis and solution conformation of a cyclic somatostatin hexapeptide containing a tetrazole cis amide bond surrogate," *Biopolymers*, 36:181-200, 1995.
Bevilacqua et al., "Developmental activation of an episomic hsp70 gene promoter in two-cell mouse embryos by transcription factor Sp1," *Nucleic Acids Res.*, 25:1333-1338, 1997.
Bird et al., "Single-chain antigen-binding proteins," *Science*, 242:423-6, 1988.
Bitko et al., "Inhibition of respiratory viruses by nasally administered siRNA," *Nature Med.*, 11:50-55, 2005.
Bodmer et al., "Cysteine 230 is essential for the structure and activity of the cytotoxic ligand TRAIL," *J. Biol. Chem.*, 275:20632-20637, 2000.
Boldin et al., "Involvement of MACH, a novel MORT1/FADD-interacting protease, in Fas/APO-1- and TNF receptor-induced cell death," *Cell*, 85:803-815, 1996.
Brody and Gold, "Aptamers as therapeutic and diagnostic agents," *Rev. Mol. Biotech.*, 74:5-13, 2000.
Brossart et al., "Identification of HLA-A2-restricted T-cell epitopes derived from MUC1 tumor antigen for broadly applicable vaccine therapies," *Blood*, 93:4309-4317, 1999.
Broughton, "Molecular modeling," *Curr. Opin. Chem. Biol.*, 1, 392-398, 1997.
Brunner et al.,"*pangolin*encodes a Lef-1 homologue that acts downstream of Armadillo to transduce the Wingless signal in *Drosophila*," *Nature*, 385:829-33, 1997.
Bumcrot et al., "RNAi therapeutics: a potential new class of pharmaceutical drugs," *Nature Chemical Biology*, 2:711-719, 2006.
Bunz, "Cell death and cancer therapy," *Curr. Opin. Pharmacol.*, 1:337-341, 2001.
Burchell et al., "A short sequence, within the amino acid tandem repeat of a cancer-associated mucin, contains immunodominant epitopes," *Int. J. Cancer*, 44:691-696, 1989.
Burchell et al., "Development and characterization of breast cancer reactive monoclonal antibodies directed to the core protein of the human milk mucin," *Cancer Res.*, 47:5476-5482, 1987.
Burns and El-Deiry, "Identification of inhibitors of TRAIL-induced death (ITIDs) in the TRAIL-sensitive colon carcinoma cell line SW480 using a genetic approach," *J. Biol. Chem.*, 276:37879-37886, 2001.
Burton et al., "Epithelial mucin (MUC1) expression and MA5 anti-MUC1 monoclonal antibody targeting in multiple myeloma," *Clin. Can. Res.*, 5:3065s-3072s, 1999.
Busfield et al., "Characterization of a neuregulin-related gene, *Don-1*, that is highly expressed in restricted regions of the cerebellum and hippocampus," *Mol. Cell. Biol.*, 17:4007-4014, 1997.
Cane et al., "Harnessing the biosynthetic code: combinations, permutations, and mutations," *Science*, 282:63-68, 1998.
Cawley et al., "Epidermal growth factor—toxin A chain conjugates: EGF-Ricin A is a potent toxin while EGF-Diphtheria fragment A is nontoxic," *Cell*, 22:563-570, 1980.
Certo et al., "Mitochondria primed by death signals determine cellular addiction to antiapoptotic BCL-2 family members," *Cancer Cell*, 9:351-365, 2006.
Chang et al., "Artificial hybrid protein containing a toxic protein fragment and a cell membrane receptor-binding moiety in a disulfide conjugate," *J. Biol. Chem.*, 252:1515-1522, 1977.
Chang et al., "Ligands for ErbB-family receptors encoded by a neuregulin-like gene," *Nature*, 387:509-512, 1997.
Chaudhary et al., "A rapid method of cloning functional variable-region antibody genes in *Escherichia coli* as single-chain immunotoxins," *Proc. Natl. Acad. Sci. U.S.A.*, 87:1066-70, 1990.
Chaudhary et al., "Activity of a recombinant fusion protein between transforming growth factor type alpha and *Pseudomonas* toxin," *Proc. Natl. Acad. Sci. USA*, 84:4538-4542, 1987.

Chen et al., "Heat shock factor 1 represses Ras-induced transcriptional activation of the c-fos gene," *J. Biol. Chem.*, 272:26803-26806, 1997.

Chou et al., "Solution structure of BID, an intracellular amplifier of apoptotic signaling," *Cell*, 96(5):615-625, 1999.

Ciborowski et al., "Screening of anti-MUC1 antibodies for reactivity with native (ascites) and recombinant (baculovirus) MUC1 and for blocking MUC1 specific cytotoxic T-lymphocytes," *Tumor Biology*, 19:147-151, 1998.

Cohen et al., "Molecular modeling software and methods for medicinal chemistry," *J. Med. Chem.*, 33:883-894, 1990.

Console et al., "Antennapedia and HIV transactivator of transcription (TAT) "protein transduction domains" promote endocytosis of high molecular weight cargo upon binding to cell surface glycosaminoglycans," *J. Biol. Chem.*, 278 :35109-14, 2003.

Creagan et al., "Phase III clinical trial of the combination of cisplatin, dacarbazine, and carmustine with or without tamoxifen in patients with advanced malignant melanoma," *J. Clin. Oncol.*, 17:1884-1890, 1999.

Cristiano et al., "Molecular conjugates: a targeted gene delivery vector for molecular medicine," *J. Mol. Med.*, 73:479, 1995.

Croghan et al., "Tissue distribution of an epithelial and tumor-associated antigen recognized by monoclonal antibody F36/22," *Cancer Res.*, 43:4980-4988, 1983.

Cunningham et al., "Calreticulin binding and other biological activities of survival peptide Y-P30 including effects of systemic treatment of rats," *Exp. Neurol.*, 163:457-468, 2000.

Cunningham et al., "Identification of a survival-promoting peptide in medium conditioned by oxidatively stressed cell lines of nervous system origin," *J. Neurosci.*, 18:7047-7060, 1998.

Cunningham et al., "Identification of the human cDNA for new survival/evasion peptide (DSEP): studies in vitro and in vivo of overexpression by neural cells," *Exp. Neurol.*, 177:32-39, 2002.

Danial et al., "Cell death critical control points," *Cell*, 116:205-219, 2004.

Daniel and Reynolds, "The catenin p120(ctn) interacts with Kaiso, a novel BTB/POZ domain zinc finger transcription factor," *Mol. Cell. Biol.*, 19:3614-23, 1999.

Datta et al., "Overexpression of Bcl-XL by cytotoxic drug exposure confers resistance to ionizing radiation-induced internucleosomal DNA fragmentation," *Cell Growth Differ*, 6:363-370, 1995.

Dawson et al., "Synthesis of proteins by native chemical ligation ," *Science*, 266:776-779, 1994.

Debnath et al., "Morphogenesis and oncogenesis of MCF-10A mammary epithelial acini grown in three-dimensional basement membrane cultures,". *Methods* 30:256-268. 2003.

Degterev et al., "Identification of small-molecule inhibitors of interaction between the BH3 domain and Bcl-xL," *Nat. Cell Biol.* 3(2):173-182, 2001.

Dejean et al., "Is MAC the knife that cuts cytochrome *c* from mitochondria during apoptosis?" *Cell Death and Differentiation*, 13:1387-1395, 2006.

Dejean et al., "Oligomeric Bax Is a Component of the Putative Cytochrome *c* Release Channel MAC, Mitochondrial Apoptosis-induced Channel," *Mol. Biol. Cell*, 16:2424-2432, 2005.

Dejean et al., "Regulation of the mitochondrial apoptosis-induced channel, MAC, by BCL-2 family proteins," *Biochem. Biophys. Acta. Mol. Basis Dis.*, 1762(2):191-201, 2006.

Deng et al., "TRAIL-induced apoptosis requires Bax-dependent mitochondrial release of Smac/DIABLO," *Genes Dev.*, 16:33-45, 2002.

Derossi et al., "Cell internalization of the third helix of the *Antennapedia* homeodomain is receptor-independent," *J Biol. Chem.*, 271:18188-93, 1996.

Derossi et al., "The third helix of the *Antennapedia* homeodomain translocates through biological membranes," *J Biol. Chem.*, 269:10444-50, 1994.

Deveraux and Reed, "IAP family proteins—suppressors of apoptosis," *Genes Dev.*, 13:239-52, 1999.

Dillman, "Antibodies as cytotoxic therapy," *J. Clin. Oncology*, 12:1497-1515, 1994.

Dorn et al., "Down-regulation of the human tumor antigen mucin by gemcitabine on the pancreatic cancer cell line capan-2," *Anticancer Research*, 24:821-826, 2004.

Doyle, "Crystal structures of a complexed and peptide-free membrane protein-binding domain: molecular basis of peptide recognition by PDZ," *Cell*, 85:1067-76, 1996.

Drucker et al., "Tamoxifen enhances apoptotic effect of cisplatin on primary endometrial cell cultures," *Anticancer Research*, 23:1549-1554, 2003.

Du et al., "Smac, a Mitochondrial Protein that Promotes Cytochrome c-Dependent Caspase Activation by Eliminating IAP Inhibition," *Cell*, 102:33-42, 2000.

Dykxhoorn et al., "The silent treatment: siRNAs as small molecule drugs," *Gene Therapy*, 13:541-552, 2006.

Elbashir et al., "Analysis of gene function in somatic mammalian cells using small interfering RNAs," *Methods*, 26:199-213, 2002.

Elbashir et al., "Functional anatomy of siRNAs for mediating efficient RNAi in *Drosophila melanogaster* embryo lysate," *EMBO Journal*, 20:6877-6888, 2001.

Elbashir et al., "RNA interference is mediated by 21-and 22-nucleotide RNAs," *Genes and Development*, 15:188-200, 2001.

Elliot and O'Hare, "Intercellular trafficking and protein delivery by a herpesvirus structural protein," *Cell*, 88:223-33, 1997.

Elmquist et al., "VE-cadherin-derived cell-penetrating peptide, pVEC, with carrier functions," *Exp. Cell Res.*, 269:237-44, 2001.

Emoto et al., "Proteolytic activation of protein kinase C delta by an ICE-like protease in apoptotic cells," *EMBO J.*, 14:6148-6156, 1995.

Enyedy et al., "Discovery of Small-Molecule Inhibitors of Bcl-2 through Structure-Based Computer Screening" *J. Med. Chem.*, 44(25):4313-4324, 2001.

Faivre et al., "Supraadditive effect of 2',2'difluorodeoxycytidine (gemcitabine) in combination with oxaliplatin in human cancer cell lines," *Cancer Chemother. Pharmacol.*, 44:117-123, 1999.

Feigl, "2,8-Dimethyl-4-(carboxymethyl)-6-(aminomethyl)phenoxathiin S-Dioxide: An Organic Substitute for the beta-Turn in Peptides," *J. Amer. Chem. Soc.*, 108:181-2, 1986.

Finn et al., "MUC-1 Epithelial Tumor Mucin-Based Immunity and Cancer Vaccines," *Immunol. Rev.*, 145:61-89, 1995.

Fontenot et al., "Biophysical characterization of one-, two-, and three-tandem repeats of human musin (muc-1) protein core," *Cancer Research*, 53:5386-5394, 1993.

Frankel and Pabo, "Cellular uptake of the tat protein from human immunodeficiency virus ," *Cell*, 55:1189-93, 1989.

French and Tschopp, "Inhibition of Death Receptor Signaling by FLICE-inhibitory Protein as a Mechanism for Immune Escape of Tumors," *J. Exp. Med.*, 190:891-893, 1999.

Futaki et al., "Arginine-rich peptides. An abundant source of membrane-permeable peptides having potential as carriers for intracellular protein delivery," *J. Biol. Chem.*, 276:5836-40, 2001.

Gay et al., "Selective BRB2 SH2 inhibitors as anti-RAS therapy," *Int. J. Cancer*, 83:235-241, 1999.

Geisbert et al., "Postexposure Protection of Guinea Pigs against a Lethal Ebola Virus Challenge is Conferred by RNA Interference," *J. Infectious Diseases*, 193:1650-1657, 2006.

Gendler et al., "A highly immunogenic region of a human polymorphic epithelial mucin expressed by carcinomas is made up of tandem repeats," *J. Biol. Chem.*, 263:12820-12823, 1988.

Gendler et al., "Molecular cloning and expression of human tumor-associated polymorphic epithelial mucin,"*J. Biol. Chem.*, 265:15286-15293, 1990.

George, D.G. et al., "Chapter 12. Current Methods in Sequence Comparison and Analysis," in: Macromolecular Sequencing and Synthesis. Selected Methods and Applications, Alan R. Liss, Inc., pp. 127-149 (1988).

Giardina and Lis, "Dynamic protein-DNA architecture of a yeast heat shock promoter," *Mol. Cell. Biol.*, 15:2737-2744, 1995.

Gopalakrishnan et al., "Application of Micro Arrayed Compound Screening (microARCS) to identify inhibitors of caspase-3," *J. Biomol. Screen*, 7:317-23, 2002.

Green and Loewenstein, "Autonomous functional domains of chemically synthesized human immunodeficiency virus tat trans-activator protein ," *Cell*, 55:1179-88, 1989.

Green et al., "Apoptotic pathways: ten minutes to dead," *Cell*, 121:671-674, 2005.

Griffith et al., "CD95-Induced Apoptosis of Lymphocytes in an Immune Privileged Site Induces Immunological Tolerance," *Immunity*, 5:7-16, 1996.

Gronenborn et al., "Protein structure determination in solution by two-dimensional and three-dimensional nuclear magnetic resonance spectroscopy," *Anal. Chem.*, 62(1):2-15, 1990.

Gross et al., "Caspase cleaved BID targets mitochondria and is required for cytochrome c release, while BCL-XL prevents this release but not tumor necrosis factor-R1/Fas death," *J. Biol. Chem.*, 274:1156-1163, 1999.

Grzelinski et al., "RNA interference-mediated gene silencing of pleiotrophin through polyethylenimine-complexed small interfering RNAs in vivo exerts antitumoral effects in glioblastoma xenografts," *Human Gene Therapy*, 17:751-766, 2006.

Guihard et al., "The Mitochondrial Apoptosis-induced Channel (MAC) Corresponds to a Late Apoptotic Event," *J. Biol. Chem.*, 45:46542-46550, 2004.

Gutierrez et al., "Gene therapy for cancer," *The Lancet*, 339:715-721, 1992.

Haim et al., "Dexamethasone, cytarabine, ifosfamide, and cisplatin as salvage therapy in Non-Hodgkin lymphoma," *Am. J. Clin. Oncol.*, 22:47-50, 1999.

Hammond et al., "Post-transcriptional gene silencing by double-stranded RNA," *Nature Genetics*, 2:110-119, 2001.

Hanson et al., "MUC1 expression in primary breast cancer: the effect of tamoxifen treatment," *Breast Cancer Research and Treatment*, 67:215-222, 2001.

Harborth et al., "Identification of essential genes in cultured mammalian cells using small interfering RNAs," *J. Cell Science*, 114:4557-4565, 2001.

Hareuveni et al., "A transcribed gene, containing a variable number of tandem repeats, codes for a human epithelial tumor antigen. cDNA cloning, expression of the transfected gene and over-expression in breast cancer tissue," *Eur. J. Biochem.*, 189:475-486, 1990.

Harlow and Lane, "Antibodies, A Lab Manual," Cold Spring Harbor, 1988.

Harris et al., "Therapeutic antibodies—the coming of age," *Tibtech*, 11:12-44, 1993.

Harrison, "Peptide-surface association: the case of PDZ and PTB domains," *Cell*, 86:341-343, 1996.

Hartman et al., "MUC1 isoform specific monoclonal antibody 6E6/2 detects preferential expression of the novel MUC1/Y protein in breast and ovarian cancer," *Int. J. Cancer*, 82:256-267, 1999.

Hayes et al., "Comparison of circulating CA15-3 and carcinembryonic antigen levels in patients with breast cancer," *J. Clin. Oncol.*, 4:1542-1550, 1986.

Hayes et al., "Genetically determined polymorphism of the circulating human breast cancer-associated DF3 antigen," *Blood*, 71:436-440, 1998.

Herr and Debatin, "Cellular stress response and apoptosis in cancer therapy," *Blood*, 98:2603-2614, 2001.

Higashiyama et al., "A novel brain-derived member of the epidermal growth factor family that interacts with ErbB3 and ErbB4," *J. Biochem.*, 122:675-680, 1997.

Higgins, "Comparison of the solution conformations of a human immunodeficiency virus peptidomimetic and its retro-inverso isomer using 1H NMR spectroscopy," *J. Pept. Res.*, 50:421-35, 1997.

Hilkens et al., "Biosynthesis of MAM-6, an epithelial sialomucin," *J. Biol. Chem.*, 263:4215-4222, 1988.

Hilkens et al., "Cell membrane-associated mucins and their adhesion-modulating property," *Trends in Biochem. Sciences*, 17:359-362, 1992.

Hilkens et al., "Complexity of MAM-6, an epithelial sialomucin associated with carcinomas," *Cancer Res.*, 49:786-793, 1989.

Hilkens et al., "Monoclonal antibodies against human milk-fat globulte membranes detecting differentiation antigens of the mammary gland and its tumors," *Int. J. Cancer*, 34:197-206, 1984.

Hird et al., "Adjuvant therapy of ovarian cancer with radioactive monoclonal antibody," *Br. J. Cancer*, 68:403-406, 1993.

Hodge et al., "The role of IL-6 and STAT3 in inflammation and cancer," *Eur. J. Cancer*, 41:2502-2512, 2005.

Honemann et al., "The IL-6 receptor antagonist SANT-7 overcomes bone marrow stromal cell-mediated drug resistance of multiple myeloma cells," *Int. J. Cancer*, 93:674-680, 2001.

Hopp, "Protein surface analysis. Methods for identifying antigenic determinants and other interaction sites," *J. Immunol. Methods*, 88:1-18, 1986.

Houghton et al., "Monoclonal antibodies: potential applications to the treatment of cancer," *Seminars in Oncology*, 13:165-179, 1986.

Hruby et al., "Design of peptides, proteins, and peptidomimetics in chi space," *Biopolymers*, 43:219-66, 1997.

Huang et al., "MUC1 cytoplasmic domain coactivates Wnt target gene transcription and confers transformation," *Cancer Biol. Ther.*, 2:702-706, 2003.

Hug et al., "Liposomes for the transformation of eukaryotic cells," *Biochem. Biophys. Acta.*, 1097:1-17, 1991.

Hull et al., "Oligosaccharide differences in the DF3 sialomucin antigen from normal human milk and the BT-20 human breast carcinomas cell line," *Cancer Commun.*, 1:261-267, 1989.

Hunt and Evans, "Till Death Us Do Part," *Science*, 293:1784-1785, 2001.

Huston et al., "Protein engineering of antibody binding sites: recovery of specific activity in an anti-digoxin single-chain Fv analogue produced in *Escherichia coli,*" *Proc. Natl. Acad. Sci U.S.A.*, 85:5879-83, 1988.

Hymowitz et al., "Triggering cell death: the crystal structure of Apo2L/TRAIL in a complex with death receptor 5," *Mol. Cell.*, 4:563-571, 1999.

Ikeda et al., "Induction of redox imbalance and apoptosis in multiple myeloma cells by the novel triterpenoid 2-cyano-3, 12-dioxoolean-1, 9-dien-28-oic acid," *Molecular Cancer Therapeutics*, 3:39-45, 2004.

Irmler et al., "Inhibition of death receptor signals by cellular FLIP," *Nature*, 388:190-195, 1997.

Itzkowitz et al., "Sialosyl-Tn. A novel mucin antigen associated with prognosis in colorectal cancer patients," *Cancer*, 66:1960-6, 1990.

J. Cavanagh et al., *Protein NMR Spectroscopy, Principles and Practice*, Academic Press, San Diego, 1996.

Jaattela et al., "Bcl-x and Bcl-2 inhibit TNF and Fas-induced apoptosis and activation of phospholipase A2 in breast carcinoma cells," *Oncogene*, 10:2297-2305, 1995.

Jackson et al., "Blockade of epidermal growth factor- or heregulin-dependent ErbB2 activation with the anti-ErbB2 monoclonal antibody 2C4 has divergent downstream signaling and growth effects," *Cancer Res.*, 64:2601-2609, 2004.

Jackson, "Contributions of protein structure-based drug design to cancer chemotherapy," *Seminars in Oncology*, 24:L164-172, 1997.

Jawhari et al., "Up-regulated cytoplasmic expression, with reduced membranous distribution, of the src substrate p120(ctn) in gastric carcinoma," *J. Pathol.* 189:180-5, 1999.

Jen et al., "Suppression of gene expression by targeted disruption of messenger RNA: available options and current strategies," *Stem Cells*, 18:307-319, 2000.

Jin et al., "CIAP1 and the serine protease HTRA2 are involved in a novel p53-dependent apoptosis pathway in mammals," *Genes Dev.*, 17:359-67, 2003.

Jones et al., "Structure-based design of lipophilic quinazoline inhibitors of thymidylate synthase," *J. Med. Chem.*, 39:904-917, 1996.

Julian and Carson, "Formation of MUC1 metabolic complex is conserved in tumor-derived and normal epithelial cells," *Biochem. Biophys. Res. Commun.*, 293:1183-1190, 2002.

Kahn et al., "Nonpeptide Mimetics of beta-Turns: A Facile Oxidative Intramolecular Cycloaddition of an Azodicarbonyl System," *J. Amer. Chem. Soc.*, 110:1638-9, 1988.

Kahn, "The design and synthesis of mimetics of peptide beta-turns," *J. Molec. Recognition*, 1:75-9, 1988.

Kalofonos et al., "Kinetics, quantitative analysis and radioimmunolocalisation using indium-111-HMFG1 monoclonal antibody in patients with breast cancer," *Cr. J. Cancer*, 59:939-942, 1989.

Kalofonos et al., "Radioimmunoschintigraphy in patients with ovarian cancer," *Acta Oncologica*, 38:629-634, 1999.

Kam et al., "MUC1 synthetic peptide inhibition of intracellular adhesion molecule-1 and MUC1 binding requires six tandem repeats," *Cancer Res.*, 58:5577-5581, 1988.

Karlsson et al., "A genetic polymorphism of a human urinary mucin," *Ann. Hum. Genet.*, 47:263, 1983.

Karvinen et al., "Homogeneous time-resolved fluorescence quenching assay (LANCE) for caspase-3," *J. Biomol. Screen.*, 7:223-31, 2002.

Kataoka et al., "FLIP prevents apoptosis induced by death receptors but not by perforin/granzyme B, chemotherapeutic drugs, and gamma irradiation," *J. Immunol.*, 161:3936-3942, 1998.

Kayagaki et al., "Metalloproteinase-mediated release of human Fas ligand," *J. Exp. Med.*, 182:1777-1783, 1995.

Kelekar et al., "Bcl-2-family proteins: the role of the BH3 domain in apoptosis," *Trends Cell Biol.*, 8:324-330, 1998.

Kemp and Stites, "A convenient preparation of derivatives of 3(s)-amino-109(r)-carboxy-1,6-diaza-cyclodeca-2,7-dione the dilactam of L-alph,gamma-diaminobutyric acid and d-glutamic acid: a beta-turn template," *Tet. Lett.*, 29:5057-60, 1988.

Kennerdell et al., "Heritable gene silencing in *Drosophila* using double-stranded RNA," *Nature Biotechnology*, 17:896-898, 2000.

Khaleque et al., "Induction of heat shock proteins by heregulin beta1 leads to protection from apoptosis and anchorage-independent growth," *Oncogene*, 24:6564-6573, 2005.

Kharbanda et al., "Nuclear signaling induced by ionizing radiation involves colocalization of the activated p56/p53lyn tyrosine kinase with p34cdc2," *Cancer Res.*, 56:3617-3621, 1996.

Kim et al., "Cholesteryl oligoarginine delivering vascular endothelial growth factor siRNA effectively inhibits tumor growth in colon adenocarcinoma," *Molecular Therapy*, 14:343-350, 2006.

Kischkel et al., "Cytotoxicity-dependent APO-1 (Fas/CD95)-associated proteins form a death-inducing signaling complex (DISC) with the receptor," *EMBO J.*, 14:5579-5588, 1995.

Kluck et al., "The Release of Cytochrome c from Mitochondria: A Primary Site for BCL-2 Regulation of Apoptosis," *Science*, 275:1132-1136, 1997.

Kondo et al., "Decreased MUC1 expression induces E-Cadherin-mediated cell adhesion of breast cancer cell lines," *Cancer Research*, 58:2014-2019, 1998.

Kotera et al., "Humoral immunity against a tandem repeat epitope of human mucin MUC-1 in Ser from breat, pancreatic, and colon cancer patients," *Cancer Research*, 54:2856-2860, 1994.

Kroemer and Reed, "Mitochondrial control of cell death," *Nat. Med.*, 6:513-519, 2000.

Kufe et al., "Differential reactivity of a novel monoclonal antibody (DF3) with human malignant versus benign breast tumors," *Hybridoma*, 3:223-232, 1984.

Kumar et al., "Abrogation of the cell death response to oxidative stress by the c-Abl tyrosine kinase inhibitor STI571," *Mol. Pharmacol.*, 63:276-282, 2003.

Kuppuswamy et al., "Multiple functional domains of Tat, the transactivator of HIV-1, defined by mutational analysis," *Nucl. Acids Res.*, 17:3551-61, 1989.

Kuwana et al., "Bid, Bax, and Lipids Cooperate to Form Supramolecular Openings in the Outer Mitochondrial Membrane," *Cell*, 111:331-342, 2002.

Lancaster et al., "Structure and expression of the human polymorphic epithelial mucin gene: an expressed VNTR unit," *Biochm. Biophys. Res. Comm.*, 173:1019-1029, 1990.

LaVallee et al., "2-Methoxyestradiol up-regulates death receptor 5 and induces apoptosis through activation of the extrinsic pathway," *Cancer Research*, 63:468-475, 2003.

LeBlanc et al., "Tumor-cell resistance to death receptor—induced apoptosis through mutational inactivation of the proapoptotic Bcl-2 homolog Bax," *Nat. Med.*, 8:274-281, 2002.

Letai et al., "Distinct BH3 domains either sensitize or activate mitochondrial apoptosis, serving as prototype cancer therapeutics," *Cell*, 2:183-192, 2002.

Lewis et al., "Efficient delivery of siRNA for inhibition of gene expression in postnatal mice," *Nature Genetics*, 32:107-108, 2002.

Li and Kufe, "The human DF3/MUC1 carcinoma-associated antigen signals nuclear localization of the catenin p120$^{ctn}$," *Biochem. Biophys. Res. Commun.*, 281:440-443, 2001.

Li et al., "The c-Src tyrosime kinase regulates signaling of the human DF3/MUC1 carcinoma-associated anitgen with GSK3β and β-catenin," *J. Biol. Chem.*, 276:6061-6064, 2001.

Li et al., "Cleavage of BID by Caspase 8 Mediates the Mitochondrial Damage in the FAS Pathway of Apoptosis," *Cell*, 94:491-501, 1998.

Li et al., "Cytochrome c and dATP-Dependent Formation of Apaf-1/Caspase-9 Complex initiates and Apoptotic Protease Cascade," *Cell*, 91:479-489, 1997.

Li et al., "DF3/MUC1 signaling in multiple myeloma cells is regulated by interleukin-7," *Cancer Biol. Ther.*, 2:187-193, 2003.

Li et al., "Heregulin targets gamma-catenin to the nucleolus by a mechanism dependent on the DF3/MUC1 oncoprotein," *Mol. Cancer Res.*, 1:765-775, 2003.

Li et al., "Human DF3/MUC1 carcinoma-associated protein functions as an oncogene," *Oncogene*, 22:6107-6110, 2003.

Li et al., "Interaction of glycogen synthase kinase 3β with the DF3/MUC1 carcinoma-associated antigen and β-catenin," *Mol. Cell. Biol.*, 18:7216-7224, 1998.

Li et al., "The c-Src tyrosine kinase regulates signaling of the human DF3/MUC1 carcinoma-associated antigen with GSK3β and β-catenin," *J. Biol. Chem.*, 276:6061-6064, 2001.

Li et al., "The EGF receptor regulates interaction of the human DF3/MUC1 carcinoma antigen with c-SRC and β-catenin," *JBC Papers in Press*, manuscript C100359200, Aug. 1, 2001.

Li et al., "The epidermal growth factor receptor regulates interaction of the human DF3/MUC1 carcinoma antigen with c-Src and beta-catenin," *J. Biol. Chem.*, 276:35239-42, 2001.

Li et al., "Using siRNA in prophylactic and therapeutic regimens against SARS coronavirus in Rhesus macaque," *Nature Med.*, 11:944-951, 2005.

Ligtenberg et al., "Cell associated episialin is a complex containing two proteins derived from a common precurso," *J. Biol. Chem.*, 267:6171-6177, 1992.

Ligtenberg et al., "Suppression of Cellular Aggregation by High Levels of Episialin," *Cancer Res.*, 52:2318-2324, 1992.

Lin et al., "Inhibition of nuclear translocation of transcription factor NF-kappa B by a synthetic peptide containing a cell membrane-permeable motif and nuclear localization sequence," *J. Biol. Chem.*, 270:14255-8, 1995.

Liu et al., "Identification of a functionally important sequence in the cytoplasmic tail of integrin beta 3 by using cell-permeable peptide analogs," *Proc. Natl Acad. Sci. U.S.A.*, 93 :11819-24, 1996.

Liu et al., "Induction of Apoptotic Program in Cell-Free Extracts: Requirement of dATP and Cyochrome c," *Cell*, 86:147-157, 1996.

Liu et al., "The Structure of a Bcl-$x_L$/Bim Fragment Complex Implications for Bim Function," *Immunity*, 19(3):341-352, 2003.

Lundy et al., "Monoclonal antibody DF3 correlates with tumor differentiation and hormone receptor status in breast cancer patients," *Breast Cancer Res. Treat.*, 5:269-276, 1985.

Luo et al., "An efficient intrathecal delivery of small interfering RNA to the spinal cord and peripheral neurons," *Molecular Pain*, 1:29, 2005.

Luo et al., "Bid, a Bcl2 Interacting Protein, Mediates Cytochrome c Release from Mitochondria in Response to Activation of Cell Surface Death Receptors," *Cell*, 94:481-490, 1998.

Makimura et al., "Reducing hypothalamic AGRP by RNA interference increases metabolic rate and decreases body weight without influencing food intake," *BMC Neuroscience*, 3:18, 2002.

Manome et al., "Enhancer sequences of the DF3 gene regulate expression of the herpes simplex virus thymidine kinase gene and confer sensitivity of human breast cancer cells to ganciclovir," *Cancer Research*, 54:5408-5413, 1994.

Maraveyas et al., "Pharmacokinetics and toxicity of an Yttrium-90-CITC-DTPA-HMFG1 radioimmunoconjugate for intraperitoneal radioimmunotherapy of ovarian cancer," *Cancer*, 73:1067-1075, 1994.

Maraveyas et al., "Pharmacokinetics, biodistribution, and dosimetry of specific and control radiolabeled monoclonal antibodies in patients with primary head and neck squamous cell carcinoma," *Cancer Research*, 55:1060-1069, 1995.

Mariani et al., "Regulation of cell surface APO-1/Fas (CD95) ligand expression by metalloproteases," *Eur. J. Immunol.*, 25:2303-2307, 1995.

Marsters et al., "A novel receptor for Apo2L/TRAIL contains a truncated death domain," *Curr. Biol.*, 7:1003-1006, 1997.

Martinez et al., "Single-stranded antisense siRNAs guide target RNA cleavage in RNAi," *Cell*, 110:563-574, 2002.

Martins, "The serine protease Omi/HtrA2: a second mammalian protein with a Reaper-like function," *Cell Death Diff.*, 9:699-701, 2002.

McGrath et al., "The Yeast STE6 gene encodes a homologue of the mammalian mulitdrug resistance P-Glycoprotein," *Nature*, 340:400, 1989.

McGuckin et al., "Prognostic significance of MUC1 epithelial mucin expression in breast cancer," *Human Pathology*, 26:432-439, 1995.

McPherson, "Crystallization of proteins from polyethylene glycol," *J. Biol. Chem.*, 251:6300-6306, 1976.

Melani et al., "Inhibition of proliferation by c-myb antisense oligodeoxynucleoides in colon adenocarcinoma cell lines that express c-myb," *Cancer Research*, 51:2897-2901, 1991.

Merlo et al., "Frequent alteraion of the DF3 tumor-associated antigen gene in primary human breat carcinomas," *Cancer Res.*, 49:6966-6971, 1989.

Mi et al., "Characterization of a class of cationic peptides able to facilitate efficient protein transduction in vitro and in vivo," *Mol. Ther.*, 2:339-47, 2000.

Milik et al., "Lung lymphocyte elimination by apoptosis in the murine response to intratracheal particulate antigen," *J. Clin. Invest.*, 99:1082-1091, 1997.

Minakuchi et al., "Atelocollagen-mediated synthetic small interfering RNA delivery for effective gene silencing in vitro and in vivo," *Nucleic Acids Research*, 32:e109, 2004.

Molenaar et al., XTcf-3 transcription factor mediates beta-catenin-induced axis formation in Xenopus embryos, *Cell*, 86:391-9, 1996.

Morris et al., "A new peptide vector for efficient delivery of oligonucleotides into mammalian cells," *Nucleic Acid Res.*, 25:2730-6, 1997.

Muthuswamy et al., "ErbB2, but not ErbB1, reinitiates proliferation and induces luminal repopulation in epithelial acini," *Nat. Cell Biol.*, 3:785-792, 2001.

Muzio et al., "FLICE, A Novel FADD-Homologous ICE/CED-3-like Protease, Is Recruited to the CD95 (fas/APO-1) Death-Inducing Signaling Complex," *Cell*, 85:817-827, 1996.

Myers, "Will combinatorial chemistry deliver real medicines?," *Curr. Opin. Biotechnol.*, 8:701-707, 1997.

Nagai and Sato, "Synthesis of a bicylic dipeptide with the shape of beta-turn central part," *Tet. Lett.*, 26:647-50, 1985.

Nagata, "Apoptosis by Death Factor," *Cell*, 88:355-365, 1997.

Nakamura et al., "RNA interference targeting transforming growth factor-beta type II receptor suppresses ocular inflammation and fibrosis," *Molecular Vision*, 10:703-711, 2004.

Nakashima et al., "Inhibition of angiogenesis by a new isocoumarin, NM-3," *J. Antibiotics*, 52:426-428, 1999.

Navia et al., "Use of structural information in drug design," *Current Opinions in Structural Biology*, 2, pp. 202-210, 1992.

Neyfakh et al., "Efflux-mediated multidrug resistance in *Bacillus subtilis*: similarities and dissimilarities with the mammalian system," *Proc. Natl. Acad. Sci. USA*, 88:4781-4785, 1991.

Nicholson et al., "Radioimmunotherapy after chemotherapy compared to chemotherapy alone in the treatment of advanced ovarian cancer: a matched analysis," *Oncology Reports* 5:223-226, 1998.

Niethammer et al., "CRIPT, a novel postsynaptic protein that binds to the third PDZ domain of PSD-95/SAP90," *Neuron*, 20:693-707, 1989.

Nishimoto et al., "Humanized anti-interleukin-6 receptor antibody treatment of multicentric Castleman disease," *Blood*, 106:2627-2632, 2005.

Niu et al., "Inhibition of HPV 16 E6 oncogene expression by RNA interference in vitro and in vivo," *Int. J. Gynecol. Cancer*, 16:743-751, 2006.

Novak and Dedhar, "Signaling through beta-catenin and Lef/Tcf," *Cell Mol. Life Sci.*, 523-37, 1999.

Obermair et al., "Expression of MUC1 splice variants in benign and malignant ovarian tumours," *Int. J. Cancer*, 100:166-171, 2002.

Oehlke et al., "Cellular uptake of an alpha-helical amphipathic model peptide with the potential to deliver polar compounds into the cell interior non-endocytically," *Biochim. Biophys. Acta.*, 1414:127-39, 1998.

Okazaki et al., "Downregulation of gastric mucin gene expression and its biosynthesis by dexamethasone in the human," *J. Clin. Gastroenterol.*, 27(suppl. 1):S91-S92, 1998.

Oosterkamp et al., "Comparison of MUC-1 mucin expression in epithelial and non-epithelial cancer cell lines and demonstration of a new short variant form (MUC-1/Z)," *Int. J. Cancer*, 72:87-94, 1997.

Opalinska et al., "Nucleic-acid therapeutics: basic principles and recent applications," *Nature Reviews Drug Discovery*, 1:503-514, 2002.

Orkin Report & Recommendations of The Panel to Assess the NIH Investment in Research on Gene Therapy, 1995.

Padrón et al., "Selective cell kill of the combination of gemcitabine and cisplatin in multilayered postconfluent tumor cell cultures," *Anti-Cancer Drugs*, 10:445-452, 1999.

Palliser et al., "An siRNA-based microbicide protects mice from lethal herpes simplex virus 2 infection," *Nature*, 439:89-94, 2006.

Pan et al., "An Antagonist Decoy Receptor and a Death Domain-Containing Receptor for TRAIL," *Science*, 277:815-818, 1997.

Pan et al., "The Receptor for the Cytotoxic Ligand TRAIL," *Science*, 276:111-113, 1997.

Pandy et al., "Association of the DF3/MUC1 breast cancer antigen with Grb2 and the Sos/Ras exchange protein," *Cancer Res.*, 55:4000-4003, 1995.

Parrish et al., "Functional anatomy of a dsRNA trigger: differential requirement for the two trigger strands in RNA interference," *Molecular Cell*, 8:1077-1087, 2000.

Parry et al., "Identification of MUC1 proteolytic cleavage sites in vivo," *Biochem. Biophys. Res. Commun.*, 283:715-720, 2001.

Paszkiewicz-Gadek et al., "Biosynthesis of MUC1 mucin in human endometrial adenocarcinoma is modulated by estradiol and tamoxifen," *Gynecol. Endocrinol.*, 17:37-44, 2003.

Pavlovic et al., "Targeting of non-small cell lung cancer using HMFG1-$^{99m}$TC monoclonal antibodies," *Med Pregl.*, 46 Suppl 1:26-28, 1993.

Perey et al., "Tumor selective reactivity of a monoclonal antibody prepared against a recombinant peptide derived from the DF3 human breast carcinoma-associated antigen," *Cancer Research*, 52:2563-2568, 1992.

Perez et al., "Antennapedia homeobox as a signal for the cellular internalization and nuclear addressing of a small exogenous peptide," *J. Cell. Sci.*, 102:717-22, 1992.

Pescarolo et al., "A retro-inverso peptide homologous to helix 1 of c-Myc is a potent and specific inhibitor of proliferation in different cellular systems," *FASEB J.*, 15:31-3, 2001.

Pitti et al., "Induction of Apoptosis by Apo-2 Ligand, a New Member of the Tumor Necrosis Factor Cytokine Family," *J. Biol. Chem.*, 271:12687-12690, 1996.

Pooga et al., "Cell penetrating PNA constructs regulate galanin receptor levels and modify pain transmission in vivo," *Nature Biotech.*, 16:857-61, 1998.

Porowska et al., "MUC1 expression in human breast cancer cells is altered by the factors affecting cell proliferation," *Neoplasma*, 49:104-109, 2002.

Porter et al., "A neural survival factor is a candidate oncogene in breast cancer," *Proc. Natl. Acad. Sci. USA*, 100:10931-10936, 2003.

Price et al, "Immunological and structural features of the protein core of human polymorphic epithelial mucin," *Molecular Immunology*, 27:795-802, 1990.

Price et al., "Summary report on the ISOBM TD-4 workshop: analysis of 56 monoclonal antibodies against the MUC1 mucin," San Diego, California, Nov. 17-23, 1996, *Tumor Biol.*, 19:sup. 1:1-20, 1998.

Raina et al. "The MUC1 oncoprotein activates the anti-apoptotic phosphoinositide 3-kinase/Akt and Bcl-xL pathways in rat 3Y1 fibroblasts," *J. Biol. Chem*,. 279:20607-20612, 2004.

Reddish et al., "Pre-immunotherapy serum CA27.29 (MUC-1) mucin level and CD69+ lymphocytes correlate with effects of Theratope sialyl-Tn-KLH cancer vaccine in active specific immunotherapy," *Cancer Immunol. Immunother.*, 42:303-9, 1996.

Reich et al., "Small interfering RNA (siRNA) targeting VEGF effectively inhibits ocular neovascularization in a mouse model," *Molecular Vision*, 9:210-216, 2003.

Ren et al., "Human MUC1 carcinoma-associated protein confers resistance to genotoxic anticancer agents," *Cancer Cell*, 5:163-175, 2004.

Ren et al., "MUC1 oncoprotein is targeted to mitochondria by heregulin-induced activation of c-Src and the molecular chaperone HSP90," *Oncogene*, 25:20-31, 2006.

Ren et al., "Protein kinase C delta regulates function of the DF3/MUC1 carcinoma antigen in beta-catenin signaling," *J. Biol. Chem.*, 277:17616-17622, 2002.

Rewcastle et al., "Tyrosine kinase inhibitors. 14. Structure-activity relationships for methylamino-substituted derivatives of 4-[(3-Bromophenyl) amino]-6-(methylamino)-pyride [3,4-*d*] pyrimidine (PD 158780), a potent and specific inhibitor of the tyrosine kinase activity of receptors for the EGF family of growth factors," *J. Med. Chem.*, 41:742-751, 1998.

Reynolds et al., "Identification of a new catenin: the tyrosine kinase substrate p120cas associates with E-cadherin complexes," *Mol. Cell. Biol.*, 14:8333-42, 1994.

Reynolds et al., "Transformation-specific tyrosine phosphorylation of a novel cellular protein in chicken cells expressing oncogenic variants of the avian cellular src gene," *Mol. Cell. Biol.*, 9:629-38, 1989.

Rondinone, "Therapeutic potential of rnai in metabolic diseases," *BioTechniques*, 40:S31-S36, 2006.

Rousselle et al., "New advances in the transport of doxorubicin through the blood-brain barrier by a peptide vector-mediated strategy," *Mol. Pharmacol.*, 57:679-86, 2000.

Ruben et al., "Structural and functional characterization of human immunodeficiency virus tat protein," *J. Virol.*, 63(1):1-8, 1989.

Sato et al., "FAP-1: A Protein Tyrosine Phosphatase That Associates with Fas," *Science*, 268:411-415, 1995.

Sattler et al., "Structure of Bcl-xL-Bak peptide complex: Recognition between regulators of apoptosis," *Science*, 275(5302):983-986, 1997.

Scaffidi et al., "Differential Modulation of Apoptosis Sensitivity in CD95 Type I and Type II Cells," *J. Biol. Chem.*, 274:22532-22538, 1999.

Schiffelers et al., "Cancer siRNA therapy by tumor selective delivery with ligand-targeted sterically stabilized nanoparticle," *Nucleic Acids Research*, 32:e149, 2004.

Schneider et al., "Mutagenesis and selection of PDZ domains that bind new protein targets," *Nat. Biotech.*, 17:170-5, 1998.

Schroeder et al., "Transgenic MUC1 interacts with epidermal growth factor receptor and correlates with mitogen-activated protein kinase activation in the mouse mammary gland," *J Biol Chem*, 276:13057-13064, 2001.

Schultz et al., "Specific interactions between the syntrophin PDZ domain and voltage-gated sodium channels," *Nat. Struct. Biol.*, 5:19-24, 1998.

Schumacher et al., "Immunoscintigraphy with positron emission tomography: Gallium-68 chelate imaging of breast cancer pretargeted with bispecific anti-MUC1/anti-Ga chelate antibodies," *Cancer Research*, 61:3712-3717, 2001.

Sekine et al., "Purification and characterization of a high molecular weight glycoprotein detectable in human milk and breast carcinomas," *J. Immunol.*, 135:3610-3615, 1985.

Shen et al., "Suppression of ocular neovascularization with siRNA targeting VEGF receptor 1," *Gene Therapy*, 13:225-234, 2006.

Sherman et al., "Ionizing radiation regulates expression of the c-jun protooncogene," *Proc. Natl. Acad. Sci. USA*, 87:5663-5666, 1990.

Shimazui et al., "Prognostic value of cadherin-associated molecules (alpha-, beta-, and gamma-catenins and p120cas) in bladder tumors," *Cancer Res.*, 56:4154-8, 1996.

Siddiqui et al., "Isolation and sequencing of a cDNA coding for the human DF3 breast carcinoma-associated antigen," *Proc. Natl. Acad. Sci. USA*, 85:2320-2323, 1988.

Sloan et al., Distribution of epithelial membrane antigen in normal and neoplastic tissues and its value in diagnostic tumor pathology, *Cancer*, 47:1786-1795, 1981.

Smith and Waterman, "Comparison of Biosequences," *Adv. Appl. Math.*, 2:482-9, 1981.

Smith et al., "Design, Synthesis, and Crystal Structure of a Pyrrolinon-Based Peptidomimetic Possessing the Conformation of a beta-Strand: Potential Application to the Design of Novel Inhibitors of Proteolytic Enzymes," *J. Amer. Chem. Soc.*, 114:10672-4, 1992.

Smolen and Maini, "Interleukin-6: a new therapeutic target," *Arthritis Res. & Ther.*, 8(Suppl. 2):S5, 2006.

Snyder et al., "Treatment of Terminal Peritoneal Carcinomatosis by a Transducible p53-Activating peptide," *PLoS Biology*, 2:186-93, 2004.

Songyang et al., "Recognition of unique carboxyl-terminal motifs by distinct PDZ domains," *Science*, 275:73-7, 1997.

Soomets et al., "Deletion analogues of transportan," *Biochim. Biophys. Acta*, 1467:165-176, 2000.

Soutschek et al., "Therapeutic silencing of an endogenous gene by systemic administration of modified siRNAs," *Nature*, 432:173-178, 2004.

Spatola, "A Peptide Backbone Modifications," In: Chemistry and Biochemistry of Amino Acids, Peptides and Proteins, 7:267-357, Marcell Dekker, NY, 1983.

Srinivasan et al., "Bcl-xL functions downstream of caspase-8 to inhibit Fas- and tumor necrosis factor receptor 1-induced apoptosis of MCF7 breast carcinoma cells," *J. Biol. Chem.*, 273:4523-4529, 1998.

Srinivasula et al., "Autoactivation of procaspase-9 by Apaf-1-mediated oligomerization," *Mol. Cell.*, 1:949-957, 1998.

Stennicke et al., "Pro-caspase-3 is a major physiologic target of caspase-8," *J. Biol. Chem.*, 273:27084-27090, 1998.

Strous and Decker, "Mucin-Type Glycoproteins," *Crit. Rev. Biochem., Mol. Biol.*, 27:57-92, 1992.

Struhl, "Delection mapping a eukaryotic promoter," *Proc. Natl. Acad. Sci. USA*, 78:4461-4465, 1981.

Subbarao et al., "pH-dependent bilayer destabilization by an amphipathic peptide," *Biochemistry*, 26:2964-2972, 1987.

Suzuki et al., "Structure of Bax: coregulation of dimer formation and intracellular localization," *Cell*, 103:645-654, 2000.

Swallow et al., "The human tumour-associated epithelial mucins are coded by an expressed hypervariable gene locus PUM," *Nature*, 328:82-84, 1987.

Takei et al., "A small interfering RNA targeting vascular endothelial growth factor as cancer therapeutics," *Cancer Research*, 64:3365-3370, 2004.

Takeichi, "Cadherins: a molecular family important in selective cell-cell adhesion," *Annu. Rev. Biochem.*, 59:237-52, 1990.

Talpaz et al., "Dasatinib in imatinib-resistant Philadelphia chromosome-positive leukemias," *N. Engl. J. Med.*, 354:2531-41, 2006.

Taylor et al., "Antisense oligonucleotides: a systematic high-throughput approach to target validation and gene function determination," *Drug Discovery Today*, 4:562-567, 1999.

Thakker et al., "siRNA-mediated knockdown of the serotonin transporter in the adult mouse brain," *Molecular Psychiatry*, 10:782-789, 2005.

Timmer et al., "Fas receptor-mediated apoptosis: a clinical application?" *J. Pathol.*, 196:125-134, 2002.

Tondini et al., "Comparison of CA15-3 and carcinoembryonic antigen in monitoring the clinical course of patients with metastatic breast cancer," *Cancer Res.*, 48:4107-4112, 1988.

Tondini et al., "Evaluation of monoclonal antibody DF3 conjugated with ricin as a specific immunotoxin for in Vitro purging of human bone marrow," *Cancer Research*, 50:1170-1175, 1990.

Topp et al., "MUC-1 specific T-cells are present in multiple myeloma patients at high frequency after allogeneic transplantation buy may not mediated the graft versus myeloma effect," *Blood*, 100: page Abstract No. 5191, 2002.

Torchilin and Levchenko, "TAT-liposomes: a novel intracellular drug carrier," *Curr. Protein Pept. Sci.*, 4:133-40, 2003.

Tseng et al., "Translocation of liposomes into cancer cells by cell-penetrating peptides penetratin and tat: a kinetic and efficacy study," *Mol. Pharmacol.*, 62:864-72, 2002.

Urban-Klein et al., "RNAi-mediated gene-targeting through systemic application of polyethylenimine (PEI)-complexed siRNA in vivo," *Gene Therapy*, 12:461-466, 2005.

Van Hof et al., "Biodistribution of 111Indium-labeled engineered human antibody CTMO1 in ovarian cancer patients: influence of protein dose," *Cancer Research*, 56:5179-5185, 1996.

Van Zonneveld et al., "Type 1 plasminogen activator inhibitor gene: Functional analysis and glucocorticoid regulation of its promoter," *Proc. Natl. Acad. Sci. USA*, 85:5525-5529, 1988.

Verhagen et al., "Identifcation of DIABLO, a Mammalian Protein that Promotes Apoptosis by Binding to and Antagonizing IAP Proteins," *Cell*, 102:43-53, 2000.

Vermeer et al., "Segregation of receptor and ligand regulates activation of epithelial growth factor receptor," *Nature*, 422:322-326, 2003.

Vives et al., "A truncated HIV-1 Tat protein basic domain rapidly translocates through the plasma membrane and accumulates in the cell nucleus," *J. Biol. Chem.*, 272 :16010-7, 1997.

Vleck et al., "Pseudorabies virus immediate-early gene overlaps with an oppositely oriented open reading frame: Characterization of their promoter and enhancer regions," *Virology*, 179:365,337, 1990.

Walczak et al., "TRAIL-R2: a novel apoptosis-mediating receptor for TRAIL," *EMBO J.*, 16:5386-5397, 1997.

Walczak et al., "Tumoricidal activity of tumor necrosis factor-related apoptosis-inducing ligand in vivo," *Nat. Med.*, 5:157-163, 1999.

Waldmann, "Monoclonal antibodies in diagnosis and therapy," *Science* 252:1657-1662, 1991.

Walsh et al., "Heterogeneity of MUC1 expression by human breast carcinoma cell lines in vivo and in vitro," *Breast Cancer Research and Treatment*, 58:255-266, 2000.

Wang and El-Deiry, "TRAIL and apoptosis induction by TNF-family death receptors," *Oncogene*, 24:8628-8633, 2003.

Wang et al., "Expression of a dominant negative heat shock factor-1 construct inhibits aneuploidy in prostate carcinoma cells," *J. Biol. Chem.*, 279:32651-32659, 2004.

Wang et al., "Phosphorylation of HSF1 by MAPK-activated protein kinase 2 on serine 121, inhibits transcriptional activity and promotes HSP90 binding," *J. Biol. Chem.*, 281:782-791, 2006.

Weber, "Physical principles of protein crystallization," *Advances in Protein Chemistry*, 41:1-36, 1991.

Wei et al., "Human MUC1 oncoprotein regulates p53-responsive gene transcription in the genotoxic stress response," *Cancer Cell*, 7:167-178, 2005.

Wei et al., "MUC1 oncoprotein stabilizes and activates estrogen receptor α," *Molecular Cell*, 21:295-305, 2006.

Wei et al., "Proapoptotic BAX and BAK: A requisite gateway to mitochondrial dysfunction and death," *Science*, 292:727-730, 2001.

Wender et al., "The design, synthesis, and evaluation of molecules that enable or enhance cellular uptake: peptoid molecular transporters," *Proc. Natl. Acad. Sci., U.S.A.*, 97:13003-8, 2000.

Wider, "Structure determination of biological macromolecules in solution using NMR spectroscopy," *BioTechniques*, 29:1278-1294, 2000.

Williams et al., "Selective inhibition of growth factor-stimulated mitogenesis by a cell-permeable Grb2-binding peptide," *J. Biol. Chem.*, 272:22349-54, 1997.

Wreschner et al., "Does a novel form of the breast cancer marker protein MUC1, act as receptor molecule that modulates signal transduction," In: *Antigen and Antibody Molecular Engineering in Breast Cancer Diagnosis and Treatment*, Ed. Ceriani Plenum Press, New York, pp. 17-26, 1994.

Xia et al., "siRNA-mediated gene silencing in vitro and invivo," *Nature Biotechnology*, 20:1006-1010, 2002.

Xing et al, "Synthetic peptides reactive with anti-human milk fat globule membrane monoclonal antibodies," *Cancer Research*, 50:89-96, 1990.

Xing et al., "Effect of variations in peptide sequence on anti-human milk fat globule membrane antibody reactions," *Immunology*, 72:304-311, 1991.

Xing et al., "Epitope mapping of anti-breast and anti-ovarian mucin monoclonal antibodies," *Molecular Immunology*, 29:641-650, 1992.

Xing et al., "Monoclonal antibodies reactive with mucin expressed in breast cancer," *Immunol. Cell. Biol.*, 67:183-195, 1989.

Xing et al., Second generation anti-MUC1 peptide monoclonal antibodies, *Cancer Research*, 52:2310-2317, 1992.

Yamamoto et al., "Interaction of the DF3/MUC1 breast carcinoma-associated antigen and beta-catenin in cell adhesion," *J. Biol. Chem.*, 272:12492-4, 1997.

Yang et al., "Prevention of Apoptosis by Bcl-2: Release of Cytochrome c from Mitochondria Blocked," *Science*, 275:1129-1132, 1997.

Yang et al., "Structure-based design and characterization of a Novel IL-6 antagonist peptide," *Mol. Immunol.*, 42:1015-1021, 2005.

Yeh et al., "Design of yeast-secreted albumin derivatives for human therapy: biological and antiviral properties of a serum albumin-CD4 genetic conjugate," *Proc. Natl. Acad. Sci. USA*, 89:1904-1908, 1992.

Yin et al., "Human MUC1 carcinoma antigen regulates intracellular oxidant levels and the apoptotic response to oxidative stress," *Biol. Chem.*, 278:35458-35464, 2003.

Yin et al., "MUC1 oncoprotein activates the FOXO3a transcription factor in a survival response to oxidative stress," *Biol. Chem.*, 279:45721-45727, 2004.

Zhang et al., "Nucleic acid aptamers in human viral disease," *Arch. Immunol. Ther. Exp.*, 52:307-315, 2004.

Zhao et al., "An RNA aptamer that interferes with the DNA binding of the HSF transcription activator," *Nucleic Acids Res.*, 34:3755-3761, 2006.

Zimmerman et al., "RNAi-mediated gene silencing in non-human primates," *Nature*, 441:111-114, 2006.

Zrihan-Licht et al., "Characterization and molecular cloning of a novel MUC1 protein, devoid of tandem repeats, expressed in human breast cancer tissue," *Eur. J. Biochem.*, 224:787-795, 1994.

Zrihan-Licht et al., "Tyrosine phosphorylation of the MUC1 breast cancer membrane proteins: cytokine receptor-like molecules," *FEBS Let.*, 356:130-136, 1994.

International Search Report and Written Opinion, issued in International Application No. PCT/US08/52792, dated Oct. 7, 2008.

* cited by examiner

```
GCTTCCGTGCGCCTAGAGCGCAGCCTGCGACTGCGGGACCCAACAACCACGTGCTG
CCGCGGCCTGGGATAGCTTCCTCCCCTCTGGCACTGCTGCCGCACACACCTCTTGGC
TGTCGCGCATTACGCACCTCACGTGTGCTTTTGCCCCCGCCTACGTGCCTACCTGTCC
CCAATACCACTCTGCTCCCCAAAGGATAGTTCTGTGTCCGTAAATCCCATTCTGTCA
CCCCACCTACTCTCTGCCCCCCCCTTTTTTGTTTTGAGACGGAGTCTTGCTCTGTCGC
CCAGGCTGGAGTGCAATGGCGCGATCTCGGCTCACTGCAACCTCCGCCTCCCGGGTT
CAAGCGATTCTCCTGCCTCAGCCTCCTGAGTAGCTGGGGTTACAGCGCCCGCCACCA
CGCTCGGCTAATTTTTGTAGTTTTTAGTAGAGACGAGGTTTCACCATCTTGGCCAGGC
TGGTCTTGAACCCCTGACCTTGTGATCCACTCGCCTCGGCCTTCCAAAGTGTTGGGAT
TACGGGCGTGACGACCGTGCCACGCCCGATCTGCCTCTTAAGTACATAACGGCCCAC
ACAGAACGTGTCCAACTCCCCCGCCCACGTTCCAACGTCCTCTCCCACATACCTCGG
TGCCCCTTCCACATACCTCAGGACCCCACCCGCTTAGCTCCATTTCCTCCAGACGCC
ACCACCACGCGTCCCGGAGTGCCCCCTCCTAAAGCTCCCAGCCGTCCACCATGCTGT
GCGTTCCTCCCTCCCTGGCCACGGCAGTGACCCTTCTCTCCCGGGCCCTGCTTCCCTC
TCGCGGGCTCTCGCTGCCTCACTTAAGCAGCGCTGCCCTTACTCCTCTCCGCCCGGTC
CGAGCGGCCCCTCAGCTTGCGCGGCCCAGCCCCGCAAGGCTCCCGGTGACCACTAG
AGGGCGGGAGGAGCTCCTGGCCAGTGGTGGAGAGTGGCAAGGAAGGACCCTAGGG
TTCATCGGAGCCCAGGTTTACTCCCTTAAGTGGAAATTTCTTCCCCCACTCCCTCCTT
GGCTTTCTCCAAGGAGGGAACCCAGGCTGCTGGAAAGTCCGGCTGGGCGGGGACT
GTGGGTTTCAGGGTAGAACTGCGTGTGGAACGGGACAGGGAGCGGTTAGAAGGGTG
GGGCTATTCCGGGAAGTGGTGGGGGGAGGGAGCCCAAAACTAGCACCTAGTCCACT
CATTATCCAGCCCTCTTATTTCTCGGCCCCGCTCTGCTTCAGTGGACCCGGGGAGGG
CGGGGAAGTGGAGTGGGAGACCTAGGGGTGGGCTTCCCGACCTTGCTGTACAGGAC
CTCGACCTAGCTGGCTTTCTTCCCCATCCCCACGTTAGTTGTTGCCCTGAGGCTAAAA
CTAGAGCCCAGGGGCCCCAAGTTCCAGACTGCCCCTCCCCCCTCCCCCGGAGCCAGG
GAGTGGTTGGTGAAAGGGGGAGGCCAGCTGGAGAACAAACGGGTAGTCAGGGGGT
TGAGCGATTAGAGCCCTTGTACCCTACCCAGGAATGGTTGGGGAGGAGGAGGAAGA
GGTAGGAGGTAGGGGAGGGGCGGGGTTTTGTCACCTGTCACCTGCTCCGGCTGTG
CCTAGGGCGGGCGGGCGGGGAGTGGGGGGACCGGTATAAAGCGGTAGGCGCCTGT
GCCCGCTCCACCTCTCAAGCAGCCAGCGCCTGCCTGAATCTGTTCTGCCCCCTCCCC
ACCCATTTCACCACCACCATG
```

FIG. 1B

```
1              221    310                529
│ │ DBD │ HR-A/B │ RD  │      │-C│  AD   │  HSF1
```

FIG. 4A

```
1        10        20        30        40        50        60        72
CQCRRKNYGQLDIFPARDTYHPMSEYPTYHTHGRYVPPSSTDRSPYEKVSAGNGGSSLSYTNPAVAAASANL  MUC1-CD
─────────────────────────────────────────────                              MUC1-CD(1-45)
                                              ───────────────────────────  MUC1-CD(46-72)
```

FIG. 4B

MDLPVGPGAAGPSNVPAFLTKLWTLVSDPDTDALICWSPSGNSFHVFDQGQFAKEVLP
KYFKHNNMASFVRQLNMYGFRKVVHIEQGGLVKPERDDTEFQHPCFLRGQEQLLENIK
RKVTSVSTLKSEDIKIRQDSVTKLLTDVQLMKGKQECMDSKLLAMKHENEALWREVAS
LRQKHAQQQKVVNKLIQFLISLVQSNRILGVKRKIPLMLNDSGSAHSMPKYSRQFSLEH
VHGSGPYSAPSPAYSSSSLYAPDAVASSGPIISDITELAPASPMASPGGSIDERPLSSSPLVR
VKEEPPSPPQSPRVEEASPGRPSSVDTLLSPTALIDSILRESEPAPASVTALTDARGHTDTE
GRPPSPPPTSTPEKCLSVACLDKNELSDHLDAMDSNLDNLQTMLSSHGFSVDTSALLDLF
SPSVTVPDMSLPDLDSSLASIQELLSPQEPPRPPEAENSSPDSGKQLVHYTAQPLFLLDPG
SVDTGSNDLPVLFELGEGSYFSEGDGFAEDPTISLLTGSEPPKAKDPTVS

FIG. 4C

MAQWNQLQQLDTRYLEQLHQLYSDSFPMELRQFLAPWIESQDWAYAASKESHATLVF
HNLLGEIDQQYSRFLQESNVLYQHNLRRIKQFLQSRYLEKPMEIARIVARCLWEESRLLQ
TAATAAQQGGQANHPTAAVVTEKQQMLEQHLQDVRKRVQDLEQKMKVVENLQDDFD
FNYKTLKSQGDMQDLNGNNQSVTRQKMQQLEQMLTALDQMRRSIVSELAGLLSAMEY
VQKTLTDEELADWKRRQQIACIGGPPNICLDRLENWITSLAESQLQTRQQIKKLEELQQK
VSYKGDPIVQHRPMLEERIVELFRNLMKSAFVVERQPCMPMHPDRPLVIKTGVQFTTKV
RLLVKFPELNYQLKIKVCIDKDSGDVAALRGSRKFNILGTNTKVMNMEESNNGSLSAEF
KHLTLREQRCGNGGRANCDASLIVTEELHLITFETEVYHQGLKIDLETHSLPVVVISNICQ
MPNAWASILWYNMLTNNPKNVNFFTKPPIGTWDQVAEVLSWQFSSTTKRGLSIEQLTTL
AEKLLGPGVNYSGCQITWAKFCKENMAGKGFSFWVWLDNIIDLVKKYILALWNEGYIM
GFISKERERAILSTKPPGTFLLRFSESSKEGGVTFTWVEKDISGKTQIQSVEPYTKQQLNN
MSFAEIIMGYKIMDATNILVSPLVYLYPDIPKEEAFGKYCRPESQEHPEADPGSAAPYLK
TKFICVTPTTCSNTIDLPMSPRTLDSLMQFGNNGEGAEPSAGGQFESLTFDMELTSECATS
PM

FIG. 4D

MEIYSPDMSEVAAERSSSPSTQLSADPSLDGLPAAEDMPEPQTEDGRTPGLVGLAVPCC
ACLEAERLRGCLNSEKICIVPILACLVSLCLCIAGLKWVFVDKIFEYDSPTHLDPGGLGQD
PIISLDATAASAVWVSSEAYTSPVSRAQSESEVQVTVQGDKAVVSFEPSAAPTPKNRIFA
FSFLPSTAPSFPSPTRNPEVRTPKSATQPQTTETNLQTAPKLSTSTSTTGTSHLVKCAEKEK
TFCVNGGECFMVKDLSNPSRYLCKCPNEFTGDRCQNYVMASFYSTSTPFLSLPE

FIG. 4E

METHODS AND COMPOSITIONS RELATING TO THE REGULATION OF MUC1 BY HSF1 AND STAT3

This application claims the benefit of the filing date of U.S. provisional patent application Ser. No. 60/888,014, filed Feb. 2, 2007, the entire content of which is hereby incorporated by reference.

The research described in this application was supported by grant no. CA97098 from the National Cancer Institute of the National Institutes of Health. Thus, the government has certain rights in the invention.

BACKGROUND OF THE INVENTION

I. Field of the Invention

This invention relates to regulation of cell signaling, cell growth and particularly to the regulation of cancer or cell growth.

II. Description of Related Art

The MUC1 heterodimeric mucin-type glycoprotein is expressed on the apical borders of secretory epithelial cells (Kufe et al. (1984) Hybridoma 3:223-232). With transformation and loss of polarity, MUC1 is expressed at high levels over the entire cell membrane and in the cytoplasm (Kufe et al. (1984) Hybridoma 3:223-232). The MUC1 N-terminal ectodomain, which consists of variable numbers of 20 amino acid tandem repeats that are extensively modified by O-linked glycans, is tethered to the cell surface through a complex with the MUC1 C-terminal transmembrane subunit (MUC1-C) (Siddiqui et al. (1988) Proc. Natl. Acad. Sci. USA 85:2320-2323; Gendler et al. (1988) J. Biol. Chem. 263:12820-12823; and Merlo et al. (1989) Cancer Res. 49:6966-6971). MUC1-C integrates receptor tyrosine kinase signaling with the Wnt pathway (Li et al. (1998) Mol. Cell. Biol. 18:7216-7224; Li et al. (2001) J. Biol. Chem. 276:35239-35242; and Li et al. (2001) J. Biol. Chem. 276:6061-6064). MUC1-C is also targeted to mitochondria and to the nucleus, where it contributes to the regulation of β-catenin/Tcf- and p53-mediated gene transcription (Ren et al. (2004) Cancer Cell 5:163-175; Huang et al. (2003) Cancer Biol. Ther. 2:702-706; and Wei et al. (2005) Cancer Cell 7:167-178). Overexpression of MUC1 is sufficient to induce transformation and to attenuate apoptosis in the response of cells to oxidative and genotoxic stress (Ren et al. (2004) Cancer Cell 5:163-175; Huang et al. (2003) Cancer Biol. Ther. 2:702-706; Li et al. (2003) Oncogene 22:6107-6110; Raina et al. (2004) J. Biol. Chem. 279:20607-20612; and Yin et al. (2004) J. Biol. Chem. 279:45721-45727).

Studies of human breast cancer cell lines and primary human breast cancers have demonstrated that overexpression of MUC1 is, at least in large part, due to increases in MUC1 mRNA levels (Abe et al. (1990) J. Cell. Physiol. 143:226-231; Hilkens et al. (1992) Trends in Biochem. Sciences 17:359-362; and Hareuveni et al. (1990) Eur. J. Biochem. 189:475-486). The precise mechanisms responsible for upregulation of MUC1 transcription in breast cancers are not known.

SUMMARY OF THE INVENTION

This invention is based, in part, on the discovery that MUC1 expression is regulated by the heregulin(HRG)/human epidermal growth factor receptor (HER), IL-6/STAT3 and heat shock (i.e., by the heat shock factor (HSF)) signaling pathways. These pathways not only have been implicated in the promotion and development of cancers but also in inflammatory conditions. For example, HSFs have been shown to promote the expression of genes such as heat shock protein 70 in response to elevated temperatures (e.g., resulting from fever or inflammation). While the invention is not limited by any particular theory or mechanism, since MUC1 expression is known to promote cell (e.g., cancer cell) viability and proliferation, inhibition of these pathways (i.e., inhibition of the expression of MUC1 through inhibition of these signaling pathways) can be useful in the treatment of cancers and inflammatory conditions.

The invention features a method of identifying a compound that inhibits the binding of MUC1 to an HSF. The method includes the steps of contacting a MUC1 reagent with an HSF (e.g., HSF1) reagent in the presence of a candidate compound and determining whether the candidate compound inhibits binding of the MUC1 reagent to the HSF (e.g., HSF1) reagent. The method can optionally include the steps of providing a MUC1 reagent and/or providing an HSF (e.g., HSF1) reagent. The method can also, optionally, include the steps of contacting a MUC1 reagent with a HSF reagent (e.g., an HSF1 reagent) in the presence of a candidate compound in the further presence of a STAT3 reagent and/or providing a STAT3 reagent. The method can be performed (i.e., carried out) in a cell or in a cell-free system. In embodiments where the method is carried out in a cell, cells suitable for the method can be any prokaryotic cell (e.g., a bacterial cell) or eukaryotic cell (e.g., a yeast cell, a nematode cell, an insect cell, a bird cell, a mammalian cell (e.g., a mouse cell, a rat cell, a guinea pig cell, a horse cell, a cow cell, a pig cell, a goat cell, a donkey cell, a monkey cell, or a human cell)). MUC1 reagents can include any agent containing a full-length, wild-type, mature MUC1 or the MUC1-cytoplasmic domain (MUC1-CD) (SEQ ID NO:2), or fragments (e.g., functional fragments) of the full-length, wild-type, MUC1 or MUC1-CD (see below). The HSF (e.g., HSF1) reagents can include any HSF (e.g., HSF1) reagent described herein.

Also provided is a process of manufacturing a compound, which includes the steps of after determining that a compound inhibits the interaction between MUC1 and HSF1 (through the preceding method), manufacturing the compound.

The invention also features a method of identifying a compound that inhibits the binding of MUC1 to STAT3. The method includes the steps of contacting a MUC1 reagent with STAT3 reagent in the presence of a candidate compound and determining whether the candidate compound inhibits binding of the MUC1 reagent to the STAT3 reagent. The method can optionally include the steps of providing a MUC1 reagent and/or providing a STAT3 reagent. The method can also, optionally, include the steps of contacting a MUC1 reagent with a STAT3 reagent in the presence of a candidate compound in the further presence of a HSF reagent (e.g., an HSF1 reagent) and/or providing an HSF reagent (e.g., an HSF1 reagent). The method can be performed (i.e., carried out) in a cell or in a cell-free system. In embodiments where the method is carried out in a cell, cells suitable for the method can be any of those described herein. MUC1 reagents can include any agent containing a full-length, wild-type, mature MUC1 or the MUC1-cytoplasmic domain (MUC1-CD) (SEQ ID NO:2), or fragments (e.g., functional fragments) of the full-length, wild-type, MUC1 or MUC1-CD (see below).

Also provided is a process of manufacturing a compound, which includes the steps of after determining that a compound inhibits the interaction between MUC1 and STAT3 (through the preceding method), manufacturing the compound.

The invention also features a method of identifying a compound that inhibits the binding of HSF (e.g., HSF1) to the MUC1 promoter, which includes the steps of: contacting an HSF (e.g., HSF1) reagent with a MUC1 promoter reagent in the presence of a candidate compound and determining whether the candidate compound inhibits binding of the HSF (e.g., HSF1) reagent to the MUC1 promoter reagent. The method can also further include the steps of contacting a MUC1 reagent, an HSF (e.g., HSF1) reagent, and a MUC1 promoter reagent in the presence of a candidate compound and determining whether the candidate compound inhibits binding of the HSF (e.g., HSF1) reagent to the MUC1 promoter reagent. The method can optionally include the steps of providing a MUC1 reagent, providing an HSF (e.g., HSF1) reagent, and/or providing a MUC1 promoter reagent. The HSF and MUC1 reagents can be any of those described herein. In some embodiments, the MUC1 promoter reagent can include or be (i) the human MUC1 promoter of SEQ ID NO:3, (ii) the heat shock element of the MUC1 promoter, or (iii) the heat shock element of the human MUC1 promoter having the sequence of SEQ ID NO:4. The method can be performed (i.e., carried out) in a cell or in a cell-free system. In embodiments where the method is carried out in a cell, cells suitable for the method can be any cell described above.

Also provided is a process of manufacturing a compound, which includes the steps of: after determining that a compound inhibits the interaction between an HSF (e.g., HSF1) and a MUC1 promoter (through the preceding method) manufacturing the compound.

Also featured is a method of identifying a compound that inhibits the binding of STAT3 to the MUC1 promoter. The method includes the steps of: contacting a STAT3 reagent with a MUC1 promoter reagent in the presence of a candidate compound and determining whether the candidate compound inhibits binding of the STAT3 reagent to the MUC1 promoter reagent. The method can further include the steps of (a) contacting a MUC1 promoter reagent with the STAT3 reagent in the presence of a candidate compound in the further presence of an HSF reagent and/or a MUC1 reagent and/or (b) providing a MUC1 reagent, a MUC1 promoter reagent, a STAT3 reagent, and/or an HSF reagent. The method can be performed (i.e., carried out) in a cell or in a cell-free system. In embodiments where the method is carried out in a cell, cells suitable for the method can be any cell described above. The MUC1 reagent and the STAT3 reagent can be any of those described herein (e.g., the MUC1 reagent can be or contain a MUC1 cytoplasmic domain (MUC1-CD) such as the MUC1-CD of SEQ ID NO:2). The MUC1 promoter reagent can contain or be the human MUC1 promoter of SEQ ID NO:3, a STAT3-binding element of the human MUC1 promoter, or the STAT3-binding element of the human MUC1 promoter of SEQ ID NO:5. In some embodiments, the MUC1 promoter reagent can be or contain both an HSE and a STAT3-binding element (e.g., the HSE of SEQ ID NO:4 and the STAT3-binding element of SEQ ID NO:5).

Also provided is a process of manufacturing a compound, which includes the steps of: after determining that a compound inhibits the interaction between STAT3 and a MUC1 promoter (through the preceding method), manufacturing the compound.

The invention provides a method of generating a compound that inhibits the interaction between MUC1 and HSF1, which includes the steps of: providing a three-dimensional structure of a molecule or a molecular complex comprising: (a) the cytoplasmic domain of MUC1 or a HSF1-binding fragment thereof; (b) a molecule comprising HSF1 or a MUC1-binding fragment thereof; or (c) a molecular complex comprising (a) and (b); designing, based on the three-dimensional structure, a compound comprising a region that inhibits the interaction between MUC1 and HSF1; and producing the compound. In some embodiments, the method can further include the step of determining whether the compound identified by the method inhibits the interaction between MUC1 and an HSF. The MUC1-CD can have the sequence SEQ ID NO:2.

Also provided herein is a method of generating a compound that inhibits the interaction between an HSF (e.g., HSF1) and the MUC1 promoter, which includes the steps of: providing a three-dimensional structure of a molecule or a molecular complex comprising: (a) an HSF (e.g., HSF1) or a heat shock element-binding fragment thereof; (b) a molecule comprising the heat shock element of the MUC1 promoter; or (c) a molecular complex of (a) and (b); designing, based on the three-dimensional structure, a compound comprising a region that inhibits the interaction between an HSF (e.g., HSF1) and the heat shock element of the MUC1 promoter; and producing the compound. The method can further include the step of determining whether the compound identified by the method inhibits the interaction between an HSF (e.g., HSF1) and a MUC1 promoter. The heat shock element can contain or be SEQ ID NO:4.

The invention features a method of generating a compound that inhibits the interaction between STAT3 and the MUC1 promoter. The method includes the steps of: providing a three-dimensional structure of a molecule or a molecular complex comprising: (a) STAT3 or a fragment thereof capable of binding to the STAT3-binding element of the MUC1 promoter; (b) a molecule comprising the STAT3-binding element of the MUC1 promoter; or (c) a molecular complex of (a) and (b); designing, based on the three-dimensional structure, a compound comprising a region that inhibits the interaction between STAT3 and the STAT3-binding element of the MUC1 promoter; and producing the compound. In some embodiments, the method can also include the step of determining whether the compound identified by the method inhibits the interaction between STAT3 and a MUC1 promoter (e.g. the STAT3-binding element of the MUC1 promoter). The STAT3-binding element can contain or be SEQ ID NO:5.

Herein is provided an in vitro method of inhibiting an interaction between MUC1 and an HSF (e.g., HSF1), which includes the steps of: contacting (i) a MUC1 reagent; (ii) an HSF reagent; or (iii) a molecular complex comprising (i) and (ii) with a compound that inhibits the interaction between MUC1 and an HSF. The method can also optionally include the step of determining whether inhibition of an interaction between the MUC1 reagent and the HSF reagent has occurred. The contacting can occur in a cell. The cell can be a human cell. The cell can be a cancer cell such as a lung cancer cell, a breast cancer cell, a colon cancer cell, a pancreatic cancer cell, a renal cancer cell, a stomach cancer cell, a liver cancer cell, a bone cancer cell, a hematological cancer cell, a neural tissue cancer cell, a melanoma cell, a thyroid cancer cell, an ovarian cancer cell, a testicular cancer cell, a prostate cancer cell, a cervical cancer cell, a vaginal cancer cell, or a bladder cancer cell. The MUC1 reagent can include the MUC1-CD, e.g., the MUC1-CD as depicted in SEQ ID NO:2. The compound can contain or be the MUC1 cytoplasmic domain, for example, the MUC1-CD as depicted in SEQ ID NO:2.

Also provided an in vitro method of inhibiting an interaction between MUC1 and STAT3, which includes the steps of: contacting (i) a MUC1 reagent; (ii) a STAT3 reagent; or (iii) a molecular complex comprising (i) and (ii) with a compound that inhibits the interaction between MUC1 and STAT3. The method can also optionally include the step of determining whether inhibition of an interaction between the MUC1 reagent and the STAT3 reagent has occurred. The contacting can occur in a cell. The cell can be a human cell. The cell can be a cancer cell such as a lung cancer cell, a breast cancer cell, a colon cancer cell, a pancreatic cancer cell, a renal cancer cell, a stomach cancer cell, a liver cancer cell, a bone cancer cell, a hematological cancer cell, a neural tissue cancer cell, a melanoma cell, a thyroid cancer cell, an ovarian cancer cell, a testicular cancer cell, a prostate cancer cell, a cervical cancer cell, a vaginal cancer cell, or a bladder cancer cell. The MUC1 reagent can include the MUC1-CD, e.g., the MUC1-CD as depicted in SEQ ID NO:2. The compound can contain or be the MUC1 cytoplasmic domain, for example, the MUC1-CD as depicted in SEQ ID NO:2.

Also provided is an in vitro method of inhibiting an interaction between an HSF and the MUC1 promoter. The method includes the steps of: contacting (i) an HSF reagent; (ii) a MUC1 promoter reagent; or (iii) a molecular complex comprising (i) and (ii) with a compound that inhibits the interaction between an HSF and the MUC1 promoter. The molecular complex (iii) can also include an STAT3 reagent and/or a MUC1 reagent. The method can also optionally include the step of determining whether inhibition of an interaction between HSF1 and the MUC1 promoter reagent has occurred. The contacting can occur in a cell. The cell can be a human cell. The cell can be a cancer cell such as any described herein. The MUC1 promoter reagent can be or contain the human MUC1 promoter as depicted in SEQ ID NO:3. The MUC1 promoter reagent can also be or contain an HSE of a human MUC1 promoter such as that depicted in SEQ ID NO:4. The compound can be an aptamer.

Herein is featured an in vitro method of inhibiting an interaction between STAT3 and the MUC1 promoter, which includes the steps of: contacting (i) a STAT3 reagent; (ii) a MUC1 promoter reagent; or (iii) a molecular complex comprising (i) and (ii) with a compound that inhibits the interaction between STAT3 and the MUC1 promoter. The molecular complex (iii) can also include an HSF reagent and/or a MUC1 reagent. The molecular complex (iii) can also include an HSF reagent and/or a MUC1 reagent. The method can also optionally include the step of determining whether inhibition of an interaction between STAT3 and the MUC1 promoter reagent has occurred. The contacting can occur in a cell. The cell can be a human cell. The cell can be a cancer cell such as any described herein. The MUC1 promoter reagent can be or contain the human MUC1 promoter of SEQ ID NO:3. The MUC1 promoter reagent can also be or contain a STAT3-binding element of a human MUC1 promoter such as that depicted in SEQ ID NO:5. The compound can be an aptamer.

The invention also provides an in vitro method of inhibiting MUC1 expression (or a method of inhibiting the growth of a cell, e.g., a cancer cell or an immune cell). The method includes the steps of: optionally identifying a cell as one expressing MUC1; and culturing the cell with a compound that inhibits a human epidermal growth factor receptor, e.g., HER2 (ErbB2/neu). The method can also, optionally, include the step of identifying a cell as one expressing a human epidermal growth factor receptor, e.g., HER2. The method can also, optionally, include the step of determining whether inhibition of MUC1 expression and/or inhibition of a HER has occurred. The cell can be a human cell. The cell can be a cancer cell such as any described herein. Inhibition of a human epidermal growth factor receptor (e.g., HER2) can be inhibition of the expression (e.g., mRNA or protein expression) of a human epidermal growth factor receptor, inhibition of the kinase activity of an epidermal growth factor receptor, inhibition of cell growth (cell proliferation), inhibition of viability, or inhibition of one or more downstream functions of an epidermal growth factor receptor such promoting the expression (e.g., mRNA or protein expression) of MUC1 or another signaling target of a human epidermal growth factor, or promoting the src-dependent phosphorylation of MUC1 (e.g., the phosphorylation of the MUC1-CD on tyrosine-46) (see, for example, Ren et al. (2006) Oncogene 25:20-31).

"Inhibition of MUC1 expression" as used herein refers to inhibition of MUC1 mRNA or MUC1 protein expression. It is understood that inhibition of MUC1 expression includes increased degradation of MUC1 mRNA or MUC1 protein (e.g., increased traffick of MUC1 protein through the proteasome).

The invention also features an in vitro method of inhibiting MUC1 expression (or a method of inhibiting the growth of a cell, e.g., a cancer cell or an immune cell), which includes the steps of: optionally identifying a cell as one expressing MUC1; and culturing the cell with a compound that inhibits the binding of heregulin (e.g., heregulin alpha or heregulin beta) with a human epidermal growth factor receptor (e.g., HER1, HER2, HER3 or HER4). The method can also, optionally, include the step of identifying a cell as one expressing a human epidermal growth factor receptor, e.g., HER1, HER2, HER3 or HER4. The method can also, optionally, include the step of determining whether inhibition of binding of heregulin with a human epidermal growth factor receptor has occurred. The cell can be a human cell. The cell can be a cancer cell such as any described herein. The heregulin can be or contain heregulin alpha or heregulin beta. The human epidermal growth factor receptor can be or contain HER1, HER2, HER3 or HER4. The compound can be or contain a soluble human epidermal growth factor receptor, e.g., an extracellular domain of a human epidermal growth factor receptor such as HER1, HER2, HER3 or HER4.

Also provided is an in vitro method of inhibiting MUC1 expression (or a method of inhibiting the growth of a cell, e.g., a cancer cell or an immune cell), which method includes the steps of: optionally identifying a cell as one expressing MUC1; and culturing the cell with a compound that inhibits IL-6 receptor. The method can also, optionally, include the step of determining whether inhibition of IL-6 receptor has occurred. The method can also, optionally, include the step of identifying a cell as one expressing IL-6R. The cell can be a human cell. The cell can be a cancer cell such as any described herein. Inhibition of IL-6R can be inhibition of the expression (e.g., mRNA or protein expression) of IL-6R, inhibition of the kinase activity of IL-6R, or inhibition of one or more downstream functions of an epidermal growth factor receptor such promoting the expression (e.g., mRNA or protein expression) of MUC1 or another signaling target of IL-6R (e.g., JAK or STAT (e.g, STAT3) proteins).

Also featured is an in vitro method of inhibiting MUC1 expression. The method includes the steps of: identifying a cell as one expressing MUC1; and culturing the cell with a compound that inhibits the binding of IL-6 to IL-6 receptor. The method can also, optionally, include the step of identifying a cell as one expressing IL-6R. The method can also, optionally, include the step of determining whether inhibition of binding of IL-6 to IL-6 receptor has occurred. The cell can be a human cell. The cell can be a cancer cell such as any described herein. The compound can be or contain IL-6R, e.g., an extracellular domain of IL-6R.

In some embodiments of any of the in vitro methods described herein, the compound can be any of the compounds described herein, e.g., any of the compounds identified through the methods of the invention. The compound can be a small molecule, an antibody, an antibody fragment, a polypeptide, or a peptidomimetic.

The invention also provides an in vivo method of inhibiting an interaction between MUC1 and an HSF (e.g., HSF1), which method includes the steps of: delivering to a subject a compound that inhibits the interaction between MUC1 and an HSF (e.g., HSF1). The method can optionally include the step of identifying a subject as one having, or suspected of having, or at risk of developing, a cancer containing one or more cells expressing MUC1. The method can also optionally include the step of identifying a subject as one having, suspected of having, or at risk of developing, an inflammatory condition mediated by one or more inflammatory cells expressing MUC1 (see below). The method can also include the step of determining whether inhibition of the interaction between MUC1 and an HSF has occurred. In some embodiments, the method can include the steps of determining whether one or more cancer cells of the subject's cancer, if present, express MUC1. In some embodiments, the method can include the step of determining whether one or more inflammatory cells mediating the inflammatory condition, if present, express MUC1. The compound can be or contain the MUC1-CD, for example, the human MUC1-CD as depicted in SEQ ID NO:2.

As used herein, a subject "at risk of developing a cancer" is a subject that has a predisposition to develop a cancer, i.e., a genetic predisposition to develop cancer such as a mutation in a tumor suppressor gene (e.g., mutation in BRCA1, p53, RB, or APC) or has been exposed to conditions that can result in cancer. Thus, a subject can also be one "at risk of developing a cancer" when the subject has been exposed to mutagenic or carcinogenic levels of certain compounds (e.g., carcinogenic compounds in cigarette smoke such as Acrolein, 4-Aminobiphenyl, Aromatic Amines, Aromatic Nitrohydrocarbons, Arsenic, Benzene, Benz{a}anthracene, Benzo{a}pyrene, Benzo {b}fluoranthene, Benzo {c}phenanthrene, Benzo {e}pyrene, Benzo {j}fluoranthene, Cadmium, Chromium, Chrysene, Dibenz {a,j}acridine, Dibenz {a,c}anthracene, Dibenz {a,h}acridine, Dibenzo {a,h}pyrene, Dibenzo {a,i}pyrene, Dibenzo {c,g}carbazole, Dichlorostilbene, 4-Ethycatechol, Formaldehyde, Hydrazine, Indeno {1,2,3-cd}pyrene, Methylchrysene, Methylfluoranthene, Methylnaphtalenes, 1-Methylindoles, 3-Methylcatechol, 4-Methylcatechol, 4-Methylcatechol, 4(methylnitrosamino)-1-(3-pyridyl)-butanone, 2-Naphthylamine, Nickel, Nitropropane, Nitrosodimethylamine, Nitrosoethymethylamine, Nitrosodiethylamine, Nitrosodi-n-propylamine, Nitrosodi-n-butylamine, Nitrosopyrrolidine, Nitrosopiperidine, Nitrosomorpholine, N'-Nitrosonornicotine, N'-Nitrosoanabasine, N'-Nitrosoanatabine, Polonium-210 (Radon), Urethane, or Vinyl Chloride). Moreover, the subject can be "at risk of developing a cancer" when the subject has been exposed to, e.g., large doses of ultraviolet light or X-irradiation, or exposed (e.g., infected) to a tumor-causing/associated virus such as papillomavirus, Epstein-Barr virus, hepatitis B virus, or human T-cell leukemia-lymphoma virus. From the above it will be clear that subjects "at risk of developing a cancer" are not all the subjects within a species of interest.

A subject "suspected of having a cancer" is one having one or more symptoms of a cancer. Symptoms of cancer are well-known to those of skill in the art and include, without limitation, breast lumps, nipple changes, breast cysts, breast pain, death, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreas metastases, difficulty swallowing, and the like. Types of cancers can include, e.g., is lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, and bladder cancer.

A subject "at risk of developing an inflammatory condition" refers to a subject with a family history of one or more inflammatory conditions (e.g., a genetic predisposition to one or more inflammatory conditions) or one exposed to one or more inflammation-inducing conditions. For example, a subject can have been exposed to a viral or bacterial superantigen such as, but not limited to, staphylococcal enterotoxins (SEs), a *streptococcus pyogenes* exotoxin (SPE), a *staphylococcus aureus* toxic shock-syndrome toxin (TSST-1), a streptococcal mitogenic exotoxin (SME) and a streptococcal superantigen (SSA). From the above it will be clear that subjects "at risk of developing an inflammatory condition" are not all the subjects within a species of interest.

A subject "suspected of having an inflammatory condition" is one who presents one or more symptoms of an inflammatory condition. Symptoms of inflammatory conditions are well known in the art and can include, but are not limited to, redness, swelling (e.g., swollen joints), joints that are warm to the touch, joint pain, stiffness, loss of joint function, fever, chills, fatigue, loss of energy, headaches, loss of appetite, muscle stiffness, insomnia, itchiness, stuffy nose, sneezing, coughing, one or more neurologic symptoms such as dizziness, seizures, or pain. An "inflammatory condition," as used herein, refers to a process in which one or more substances (e.g., substances not naturally occurring in the subject), via the action of white blood cells (e.g., B cells, T cells, macrophages, monocytes, or dendritic cells) inappropriately trigger a pathological response, e.g., a pathological immune response. Accordingly, such cells involved in the inflammatory response are referred to as "inflammatory cells." The inappropriately triggered inflammatory response can be one where no foreign substance (e.g., an antigen, a virus, a bacterium, a fungus) is present in or on the subject. The inappropriately triggered response can be one where a self-component (e.g., a self-antigen) is targeted (e.g., an autoimmune disorder such as multiple sclerosis). The inappropriately triggered response can also be an response that is inappropriate in magnitude or duration, e.g., anaphylaxis. Thus, the inappropriately targeted response can be due to the presence of a microbial infection (e.g., viral, bacterial, or fungal). Types of inflammatory conditions (e.g., autoimmune diseasease) can include, but are not limited to, osteoarthritis, Rheumatoid arthritis (RA), spondyloarhropathies, POEMS syndrome, Crohn's disease, multicentric Castleman's disease, systemic lupus erythematosus (SLE), multiple sclerosis (MS), muscular dystrophy (MD), insulin-dependent diabetes mellitus (IDDM), dermatomyositis, polymyositis, inflammatory neuropathies such as Guillain Barre syndrome, vasculitis such as Wegener's granulomatosus, polyarteritis nodosa, polymyalgia rheumatica, temporal arteritis, Sjogren's syndrome, Bechet's disease, Churg-Strauss syndrome, or Takayasu's arteritis. Also included in inflammatory conditions are certain types of allergies such as rhinitis, sinusitis, urticaria, hives, angioedema, atopic dermatitis, food allergies (e.g., a nut allergy), drug allergies (e.g., penicillin), insect allergies (e.g., allergy to a bee sting), or mastocytosis. Inflammatory conditions can also include ulcerative colitis and asthma.

The invention also provides an in vivo method of inhibiting an interaction between MUC1 and STAT3, which method includes the steps of: delivering to a subject a compound that inhibits the interaction between MUC1 and STAT3. The method can optionally include the step of identifying a subject as one having, or suspected of having, or at risk of developing, a cancer containing one or more cells expressing MUC1. The method can also optionally include the step of identifying a subject as one having, suspected of having, or at risk of developing, an inflammatory condition mediated by one or more inflammatory cells expressing MUC1 (see below). The method can also include the step of determining whether inhibition of the interaction between MUC1 and STAT3 has occurred. In some embodiments, the method can include the steps of determining whether one or more cancer cells of the subject's cancer, if present, express MUC1. In some embodiments, the method can include the step of determining whether one or more inflammatory cells mediating the inflammatory condition, if present, express MUC1. The compound can be or contain the MUC1-CD, for example, the human MUC1-CD as depicted in SEQ ID NO:2.

Also provided is an in vivo method of inhibiting an interaction between an HSF (e.g., HSF1) and the MUC1 promoter, which includes the steps of: delivering to a subject a compound that inhibits the interaction between an HSF and the MUC1 promoter. The method can optionally include the step of identifying a subject as one having, suspected of having, or at risk of developing, a cancer containing one or more cells expressing MUC1. In some embodiments, the method can include the step of determining whether one or more cancer cells of the subject's cancer, if present, express MUC1. The method can also include the step of determining if inhibition of the interaction between an HSF and the MUC1 promoter has occurred. The subject can be any described herein. The cancer can be any of those described herein. The method can also optionally include the step of identifying a subject as one having, suspected of having, or at risk of developing, an inflammatory condition mediated by one or more inflammatory cells expressing MUC1. In some embodiments, the method can include the step of determining whether one or more inflammatory cells mediating the inflammatory condition, if present, express MUC1. The inflammatory condition can be any of those described herein. The compound can be an aptamer.

Herein is featured an in vivo method of inhibiting an interaction between STAT3 and the MUC1 promoter that includes the steps of: delivering to a subject a compound that inhibits the interaction between STAT3 and the MUC1 promoter. The method can optionally include the step of identifying a subject as one having, suspected of having, or at risk of developing, a cancer containing one or more cells expressing MUC1. The subject can be any described herein. The cancer can be any of those described herein. The method can also optionally include the step of identifying a subject as one having, suspected of having, or at risk of developing, an inflammatory condition mediated by one or more inflammatory cells expressing MUC1. The inflammatory condition can be any of those described herein. In some embodiments, the method can also include the step of determining whether inhibition of the interaction between STAT3 and the MUC1 promoter has occurred. In some embodiments, the method can include the steps of determining whether one or more cancer cells of the subject's cancer, if present, express MUC1. In some embodiments, the method can include the step of determining whether one or more inflammatory cells mediating the inflammatory condition, if present, express MUC1. The compound can be an aptamer.

Also provided is an in vivo method of inhibiting MUC1 expression (or a method of inhibiting the growth of a cell, e.g., a cancer cell), which method contains the steps of: optionally identifying a subject as one having, or suspected of having, a cancer comprising one or more cells expressing MUC1; and delivering to the subject a compound that inhibits a human epidermal growth factor receptor, wherein inhibition of the human epidermal growth factor receptor inhibits MUC1 expression. The subject can be any described herein (e.g., a human patient). The cancer can be any of those described herein. The method can also include the step of determining whether inhibition of MUC1 expression has occurred and/or whether inhibition of a human epidermal growth factor receptor has occurred. In some embodiments, the method can include the steps of determining whether one or more cancer cells of the subject's cancer, if present, express MUC1. The human epidermal growth factor receptor can be or contain HER1, HER2, HER3, or HER4. Inhibition of a human epidermal growth factor receptor can be inhibition of the expression (e.g., mRNA or protein expression) of a human epidermal growth factor receptor, inhibition of the kinase activity of an epidermal growth factor receptor, inhibition of cell growth (cell proliferation), inhibition of viability, or inhibition of one or more downstream functions of an epidermal growth factor receptor such promoting the expression (e.g., mRNA or protein expression) of MUC1 or another signaling target of a human epidermal growth factor, or promoting the src-dependent phosphorylation of MUC1 (e.g., the phosphorylation of the MUC1-CD on tyrosine-46).

Also featured is an in vivo method of inhibiting MUC1 expression (or a method of inhibiting the growth of a cell, e.g., a cancer cell). The method includes the steps of: optionally identifying a subject as one having, or suspected of having, a cancer comprising one or more cells expressing MUC1; and delivering to the subject a compound that inhibits the binding of a heregulin with a human epidermal growth factor receptor, wherein inhibition of binding of the heregulin to the human epidermal growth factor receptor inhibits MUC1 expression. The subject can be any described herein (e.g., a human patient). The cancer can be any of those described herein. The method can also include the step of determining whether inhibition of the binding of a heregulin with a human epidermal growth factor receptor and/or MUC1 expression has occurred. In some embodiments, the method can include the steps of determining whether one or more cancer cells of the subject's cancer, if present, express MUC1. The human epidermal growth factor receptor can be or contain HER1, HER2, HER3 or HER4. The compound can be or contain a soluble human epidermal growth factor receptor, e.g., an extracellular domain of a human epidermal growth factor receptor such as HER1, HER2, HER3 or HER4.

The invention also provides an in vivo method of inhibiting MUC1 expression (or a method of inhibiting the growth of a cell, e.g., a cancer cell or an inflammatory cell (e.g., an immune cell involved in an inflammatory response), the method containing the steps of: optionally identifying a subject as one having, or suspected of having, a cancer comprising one or more cells expressing MUC1; and delivering to the subject a compound that inhibits IL-6 receptor, wherein inhibition of the IL-6 inhibits MUC1 expression. The subject can be any described herein (e.g., a human patient). The cancer can be any of those described herein. The method can also optionally include the step of identifying a subject as one having, suspected of having, or at risk of developing, an inflammatory condition mediated by one or more inflammatory cells expressing MUC1. The method can also include the step of determining whether inhibition of IL-6 receptor and/or MUC1 expression has occurred. In some embodiments, the method can include the steps of determining whether one or more cancer cells of the subject's cancer, if present, express MUC1. In some embodiments, the method can include the step of determining whether one or more inflammatory cells mediating the inflammatory condition, if present, express MUC1. The inflammatory condition can be any of those described herein. Inhibition of IL-6R can be inhibition of the expression (e.g., mRNA or protein expression) of IL-6R, inhibition of the kinase activity of IL-6R, or inhibition of one or more downstream functions of an epidermal growth factor receptor such promoting the expression (e.g., mRNA or protein expression) of MUC1 or another signaling target of IL-6R.

Also provided herein is an in vivo method of inhibiting MUC1 expression (or a method of inhibiting the growth of a cell, e.g., a cancer cell or an immune cell), the method comprising: identifying a subject as one having, or suspected of having, an inflammatory condition mediated by one or more inflammatory cells expressing MUC1; and delivering to the subject a compound that inhibits IL-6 receptor, wherein inhibition of the IL-6 inhibits MUC1 expression. The method can also include the step of determining whether inhibition of IL-6 receptor and/or MUC1 expression has occurred. The method can also include the step of determining whether the one or more cells mediating the inflammatory condition, if present, express MUC1. The inflammatory condition can be any of those described herein. The subject can be any subject described herein, e.g., a human patient. The inflammatory condition can be any of those described herein. Inhibition of IL-6R can be inhibition of the expression (e.g., mRNA or protein expression) of IL-6R, inhibition of the kinase activity of IL-6R, or inhibition of one or more downstream functions of an epidermal growth factor receptor such promoting the expression (e.g., mRNA or protein expression) of MUC1 or another signaling target of IL-6R (e.g., JAK or STAT proteins such as STAT3).

Also featured is an in vivo method of inhibiting MUC1 expression (or a method of inhibiting the growth of a cell, e.g., a cancer cell or an immune cell), which includes the steps of: optionally identifying a subject as one having, or suspected of having, a cancer comprising one or more cells expressing MUC1; and delivering to the subject a compound that inhibits the binding of IL-6 to IL-6 receptor, wherein inhibition of the binding of IL-6 to IL-6 receptor inhibits MUC1 expression. The method can also include the step of determining whether inhibition of binding of IL-6 to IL-6 receptor and/or MUC1 expression has occurred. The method can also include the step of determining if one or more cancer cells of the subject's cancer, if present, express MUC1. The subject can be any subject described herein, e.g., a human patient. The compound can be or contain a soluble IL-6R, e.g., an extracellular domain of IL-6R.

The invention also features an in vivo method of inhibiting MUC1 expression (or a method of inhibiting the growth of a cell, e.g., a cancer cell or an immune cell). The method includes the steps of: optionally identifying a subject as one having, or suspected of having, an inflammatory condition mediated by one or more inflammatory cells expressing MUC1, and delivering to the subject a compound that inhibits the binding of IL-6 to IL-6 receptor, wherein inhibition of the binding of IL-6 to IL-6 receptor inhibits MUC1 expression. In some embodiments, the method can include the step of determining whether one or more inflammatory cells mediating the inflammatory condition, if present, express MUC1. In some embodiments, the method can also include the steps of determining whether inhibition of the binding of IL-6 to IL-6R has occurred. The compound can be or contain a soluble IL-6R, e.g., an extracellular domain of IL-6R.

In some embodiments of any of the in vivo methods described herein, the methods can also further include the step of: administering to the subject one or more additional therapeutic agents. The one or more additional therapeutic agents can be one or more chemotherapeutic agents, one or more forms of immunotherapy, one or more forms of ionizing radiation, one or more forms of a hormonal therapy, or a hyperthermotherapy. The one or more forms of ionizing radiation can be, for example, gamma-irradiation, X-irradiation, or beta-irradiation. The one or more chemotherapeutic agents can be, for example, cisplatin, carboplatin, procarbazine, mechlorethamine, cyclophosphamide, camptothecin, adriamycin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, tamoxifen, taxol, transplatinum, 5-fluorouracil, vincristin, vinblastin, methotrexate, or an analogue of any of the aforementioned. The one or more additional therapeutic agents can be inhibitors of human epidermal growth factor receptor 2 (HER2, ErbB2, or neu; hereinafter referred to as HER2) such as Herceptin, Iressa, Tarceva, Erbitux, Lapatinib, Sutent (sunitinib malate), or an analogue of any of the aforementioned. Where the condition to be treated is an inflammatory condition, the one or more therapeutic agents can be a non-steroidal anti-inflammatory drug (NSAID) such as a COX-2 inhibitor (e.g., aspirin, indomethacin, ibuprofen, naprozen, piroxican, nabumentone), a disease-modifying anti-rheumatic drug (DMARDS) (e.g., gold, hydroxychloroquine, penicillamine, sulfasalazine), a biological response modifier (e.g., an anti-TNF therapy such a soluble TNF receptor or an antibody that specifically binds to and inhibits TNF such as Humira (D2E7), Remicade (infliximab), or Enbrel (etanercept)), or a corticosteroid (e.g., Cortisone, Decadron, Delta-cortef, Deltasone, Dexamethasone, Hydrocortisone, Kenacort, Medrol, Methylprednisolone, Orasone, Prednisolone, Prednisone, Triamcinolone, Aristocort, Celestone, Cinalone, Depo-medrol, Hydeltrasol, Hydeltra TBA, Kenalog).

In any of the in vivo methods described herein, the compound can be any of the compounds described herein. The compound can be a small molecule, an antibody, an antibody fragment, a polypeptide, or a peptidomimetic.

In some embodiments of any of the in vivo methods, the delivery can involve administering to a subject one or more of any of the compounds described herein, e.g., a compound of the invention.

In some embodiments of any of the in vivo methods, where the compound is a polypeptide, the methods can involve administering to the subject a nucleic acid comprising a nucleotide sequence encoding the polypeptide, the nucleotide sequence being operably-linked to a transcriptional regulatory sequence. The nucleic acid can be in a recombinant cell transfected with the nucleic acid and secreting the polypeptide. The recombinant cell can be a transfected cell, or the progeny of a transfected cell, made by transfecting a cell derived from the subject. The cell that is transfected can be obtained directly from the subject or can be the progeny of a cell obtained from the subject.

"Polypeptide" and "protein" are used interchangeably and mean any peptide-linked chain of amino acids, regardless of length or post-translational modification.

The MUC1, HSF (e.g., HSF1, HSF2, HSF3, or HSF4), STAT3, heregulin (HRG) (e.g., heregulin alpha or heregulin beta), human epidermal growth factor receptor (HER) (e.g., HER1, HER2 (ErbB2/Neu), HER3, or HER4), IL-6, and IL-6 receptor (IL-6R) "reagents" used in any of the methods of the invention can contain, or be, wild-type, full-length, mature proteins or fragments (e.g., functional fragments) of such proteins. The reagents can also be variants of full-length, mature, wild-type proteins or fragments of the proteins having additions, deletions, or substitutions. Reagents with substitutions will generally have not more than 50 (e.g., not more than one, two, three, four, five, six, seven, eight, nine, ten, 12, 15, 20, 25, 30, 35, 40, or 50) conservative amino acid substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids.

Additions (addition variants) include full-length, wild-type, mature polypeptides or fragments with internal or terminal (C or N) irrelevant or heterologous amino acid sequences (i.e., sequences derived from other proteins or synthetic sequences not corresponding to any naturally occurring protein). The sequences can be, for example, an antigenic tag (e.g., FLAG, polyhistidine, hemagluttanin (HA), glutathione-S-transferase (GST), or maltose-binding protein (MBP)). Heterologous sequences can also be proteins useful as diagnostic or detectable markers, for example, luciferase, green fluorescent protein (GFP), or chloramphenicol acetyl transferase (CAT). Heterologous sequences can be of varying length and in some cases can be a larger sequences than the full-length, wild-type mature polypeptides of fragments (functional fragments) thereof.

A "fragment," as used herein, refers to a segment of the polypeptide that is shorter than a full-length, immature polypeptide. A "functional fragment" of a polypeptide has at least 25% (e.g., at least 25%, at least 30%, at least 35%, at least 40%, at least 50%, at least 55%, at least 60%, at least 70%, at least 80%, at least 90%, at least 95%, at least 98%, at least 99%, at least 99.5%, or 100% or more) of the activity of the mature, polypeptide (see above). Fragments of a polypeptide include terminal as well internal deletion variants of a polypeptide. The polypeptides, fragments, or their variants can be of any species expressing relevant forms of the wild-type, human proteins, such as e.g., nematode, insect, plant, bird, reptile, or mammal (e.g., a mouse, rat, dog, cat, goat, pig, cow, horse, whale, or monkey). All that is required is that such variants have at least 25% (e.g., at least: 30%; 40%; 50%; 60%; 70%; 75%; 80%; 85%; 90%; 95%; 97%; 98%; 99%; 99.5%, or 100% or even greater) of the activity of the wild-type, full-length, mature protein.

In the case of MUC1, the relevant activity is the ability to bind (interact) with an HSF (e.g., HSF1, HSF2, HSF3, or HSF4). This activity is also sometimes referred to as HSF (e.g., HSF1)-binding activity.

In the case of an HSF (e.g., HSF1), the relevant activity is the ability to bind (interact) with MUC1 (or the MUC1-CD). This activity is thus sometimes referred to as MUC1-binding activity. In some embodiments, the relevant HSF activity is the ability to bind to the MUC1 promoter (e.g., the MUC1 promoter sequence of SEQ ID NO:3 or SEQ ID NO:4). This HSF activity is sometimes referred to as MUC1-promoter binding activity.

In the case of STAT3, the relevant activity is the ability to bind to the MUC1 promoter (e.g., the MUC1 promoter sequence of SEQ ID NO:3 or SEQ ID NO:5). This STAT3 activity is sometimes referred to as MUC1-promoter-binding activity. In some embodiments, the relevant STAT3 activity is the ability to bind to MUC1. This STAT3 activity is sometimes referred to as MUC1-binding activity.

In the case of heregulin (e.g., heregulin alpha or heregulin beta), the relevant activity is the ability to bind to a human epidermal growth factor receptor (e.g., HER1, HER3, or HER4). This activity is also sometimes referred to as HER (HER1, HER3, or HER4)-binding activity. In some embodiments, the relevant heregulin activity is the ability to activate a HER. This heregulin activity is thus sometimes referred to as HER-activation activity.

In the case of a HER (e.g., HER1, HER2, HER3, or HER4), the relevant activity is one or more downstream activities or functions of a HER (see above). This activity is also sometimes referred to as HER-activity.

In the case of IL-6, the relevant activity is the ability to bind to IL-6 receptor (IL-6R). This activity is also sometimes referred to as IL-6R-binding activity. In some embodiments, the relevant IL-6 activity is the ability to activate IL-6R. This heregulin activity is thus sometimes referred to as HER-activation activity.

In the case of IL-6R, the relevant activity is one or more downstream activities or functions of IL-6R (see above). This activity is also sometimes referred to as IL-6R-activity.

As used herein, "MUC1 cytoplasmic domain" or "MUC1-CD" refers to a 72 amino acid portion of the full-length MUC1 (SEQ ID NO:1) and is depicted in SEQ ID NO:2.

It is understood that the terms "HSF" and "STAT3" refer to all forms (e.g., splice variants) of the proteins that bind to MUC1 (e.g., the MUC1-CD) and/or that bind to a MUC1 promoter. Methods of testing for an interaction between MUC1 and a BH3-containing protein are known in the art and described in the Examples below. Similarly, the term "MUC1 promoter" refers to all forms (e.g., allelic variants) of the MUC1 promoter that bind to STAT3 and/or to an HSF (e.g., HSF1).

As used herein, a "MUC1 promoter reagent" or "MUC1 promoter reagent" contains, or is, (a) a full-length, native MUC1 promoter nucleic acid sequence (e.g., the MUC1 promoter nucleic acid sequence depicted in SEQ ID NO:3), (b) a functional fragment of (a), or a homologous or complementary sequence variant of (a) or (b) (see below). As further described below, the MUC1 promoter can be from any species (e.g., nematode, insect, plant, bird, reptile, or mammal (e.g., a mouse, rat, dog, cat, goat, pig, cow, horse, whale, or monkey) that expresses a MUC1 protein from a MUC1 promoter sequence. "Functional fragments" of a MUC1 promoter or MUC1 promoter reagent, as used herein, refer to any MUC1 promoter fragments that substantially retain at least 25% (e.g., at least 25%, at least 30%, at least 35%, at least 40%, at least 50%, at least 55%, at least 60%, at least 70%, at least 80%, at least 90%, at least 95%, at least 98%, at least 99%, at least 99.5%, or 100% or more) of the ability of a full-length promoter region (e.g., the human MUC1 promoter sequence of SEQ ID NO:3) to be bound by (or to bind to) a relevant transcription factor (e.g., human HSF1 of SEQ ID NO:14 or human STAT3 of SEQ ID NO:15). In some embodiments, "functional fragments" of a MUC1 promoter or MUC1 promoter reagent are any MUC1 promoter fragments that retain at least 25% (see above) of the ability of a full-length MUC1 promoter sequence (e.g., the human MUC1 promoter sequence of SEQ ID NO:3) to be bound by an HSF (e.g., the human HSF1 protein of SEQ ID NO:14). In this case, suitable functional fragments of a MUC1 promoter can contain, or be, the HSF binding element (HSE) (SEQ ID NO:4) of the human MUC1 promoter (SEQ ID NO:3). In some embodiments, "functional fragments" of a MUC1 promoter or MUC1 promoter reagent are any MUC1 promoter fragments that retain at least 25% of the ability of the full-length, native promoter (e.g., human MUC1 promoter of SEQ ID NO:3) to be bound by STAT3 (e.g., human STAT3 of SEQ ID NO:15). In this case, functional fragments of a MUC1 promoter can contain, or be, the human STAT3-binding element depicted in SEQ ID NO:5.

In some embodiments, functional fragments of the MUC1 promoter include both an HSE and STAT3-binding element of a MUC1 promoter, e.g., both SEQ ID NO:4 and SEQ ID NO:5.

In some embodiments, the functional fragments of a MUC1 promoter include the human MUC1 promoter nucleic acid sequence depicted in SEQ ID NO:3.

The MUC1 promoter can be from any species that expresses MUC1 (e.g., any of the MUC1-expressing species described above).

Variants of a MUC1 promoter can also have a sequence that is homologous, e.g., a sequence bearing at least about 70% (e.g., at least about 75%, at least about 80%, at least about 85%, at least about 90%, at least about 95%, or at least about 99%) homology to a native MUC1 promoter sequence. A "native" nucleic acid sequence is one that is derived from nature (e.g., a human MUC1 promoter sequence). Such native sequences can be isolated from nature or can be produced by recombinant or synthetic methods. Thus a native sequence nucleic acid can have the nucleic acid sequence of naturally occurring human nucleic acid sequences, monkey nucleic acid sequences, murine nucleic acid sequences, or any other species that expresses a MUC1 polypeptide from a MUC1 promoter. As used herein, a "homologous" or "homologous nucleic acid sequence" or similar term, refers to sequences characterized by homology at the nucleotide level of at least a specified percentage and is used interchangeably with sequence identity. As described above, homologous nucleic acid sequences, or homologous MUC1 promoter reagent sequences, can include sequences from any species that expresses MUC1 from a MUC1 promoter.

Percent homology or identity can be determined by, for example, the Gap program (Wisconsin Sequence Analysis Package, Version 8 for UNIX, Genetics Computer Group, University Research Park, Madison, Wis.), using default settings, which uses the algorithm of Smith and Waterman ((1981) Adv. Appl. Math. 2:482-489). In some embodiments, homology between a probe and target (see below) is between about 50% to about 60%. In some embodiments, homology between a probe and target nucleic acid is between about 55% to 65%, between about 65% to 75%, between about 70% to 80%, between about 75% and 85%, between about 80% and 90%, between about 85% and 95%, or between about 90% and 100%.

The term "probe," as used herein, refers to nucleic acid sequences of variable length. In some embodiments, probes comprise at least 10 and as many as 6,000 nucleotides. In some embodiments probes comprise at least 12, at lease 14, at least 16, at least 18, at least 20, at least 25, at least 50 or at least 75 or 100 contiguous nucleotides. Longer length probes are usually obtained from natural or recombinant sources (as opposed to direct, chemical synthesis), are highly specific to the target sequence, and are much slower to hybridize to the target than longer oligomers. Probes can be single or double stranded nucleic acid molecules.

In some embodiments, the MUC1 promoter reagent can have a sequence comprising one or both strands with partial complementary (e.g., at least 50%, at least 60%, at least 70%, at least 80%, at least 90%, at least 95%, at least 96%, at least 97%, at least 98%, at least 99% complementary) to a region, portion, domain, or segment of the human MUC1 promoter (SEQ ID NO:3, SEQ ID NO:4, or SEQ ID NO:5). In some embodiments, the MUC1 promoter reagent can have a sequence comprising one or both strands with full complementary (i.e., 100% complementary) to a region, portion, domain, or segment of the human MUC1 promoter (SEQ ID NO:3, SEQ ID NO:4, or SEQ ID NO:5). Sequence "complementarity" refers to the chemical affinity between specific nitrogenous bases as a result of their hydrogen bonding properties (i.e., the property of two nucleic acid chains having base sequences such that an antiparallel duplex can form where the adenines and uracils (or thymine, in the case of DNA or modified RNA) are apposed to each other, and the guanines and cytosines are apposed to each other). Fully complementary sequences, thus, would be two sequences that have complete one-to-one correspondence (i.e., adenine to uracil and guanine to cytosine) of the base sequences when the nucleotide sequences form an antiparallel duplex.

As used herein, a "promoter" refers to a DNA sequence that enables a gene to be transcribed. The promoter is recognized by RNA polymerase, which then initiates transcription. Thus, a promoter contains a DNA sequence that is either bound directly by, or is involved in the recruitment, of RNA polymerase. A promoter sequence can also include "enhancer regions," which are one or more regions of DNA that can be bound with proteins (namely, the trans-acting factors, much like a set of transcription factors) to enhance transcription levels of genes (hence the name) in a gene-cluster. The enhancer, while typically at the 5' end of a coding region, can also be within an intronic region of a gene, or 3' to the coding region.

As used herein, "operably linked" means incorporated into a genetic construct so that expression control sequences effectively control expression of a coding sequence of interest.

Unless otherwise defined, all technical and scientific terms used herein have the same meaning as commonly understood by one of ordinary skill in the art to which this invention pertains. Preferred methods and materials are describe below, although methods and materials similar or equivalent to those described herein can be used in the practice or testing of the present invention. All publications, patent applications, patents, and other references mentioned herein are incorporated by reference in their entirety. The materials, methods, and examples disclosed herein are illustrative only and not intended to be limiting.

Other features and advantages of the invention, e.g., methods for identifying a compound that inhibits the binding of MUC1 to HSF1, will be apparent from the following description, from the drawings and from the claims.

BRIEF DESCRIPTION OF THE DRAWINGS

FIG. 1B is a depiction of an exemplary nucleotide sequence for the human MUC1 promoter (SEQ ID NO:3)

FIG. 4A is a diagram depicting the domain structure of the human HSF1 protein. The numbers above the diagram indicate the amino acid position and denote the relative boundaries of each respective domain within the protein. "DBD" refers to the DNA binding domain of HSF1. "HR-A/B" refers to the hydrophobic repeat ("HR") regions (HR-A/B/C). "RD" refers to the regulatory domain of human HSF1 protein. "AD" refers to the activation domain of human HSF1 protein. "–C" refers to the helix region C of human HSF1 protein.

FIG. 4B is a diagram depicting the domain structure of the human MUC1 cytoplasmic domain (MUC1-CD; SEQ ID NO:2). The numbers above the diagram indicate the amino acid positions (1-72). Two smaller fragments of MUC1-CD are indicated below the MUC1-CD sequence. These fragments correspond to amino acids 1-40 and 46-72 of the MUC1-CD.

FIG. 4C is a depiction of an exemplary amino acid sequence for human HSF1 (SEQ ID NO:14).

FIG. 4D is a depiction of an exemplary amino acid sequence for human STAT3 (SEQ ID NO:15).

FIG. 4E is a depiction of an exemplary amino acid sequence for heregulin (HRG1) (SEQ ID NO:16).

DESCRIPTION OF THE ILLUSTRATIVE EMBODIMENTS

Figure 1A:
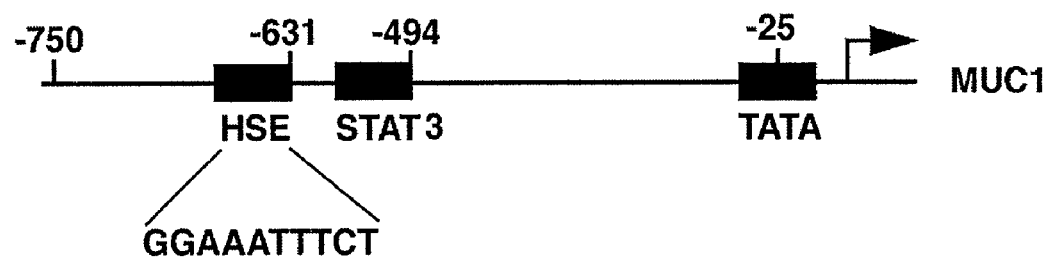
FIG. 1A is a diagram depicting the human MUC1 promoter. The reverse numbering starting at −750 (extreme left) indicates the nucleotide position relative to the (ATG) start codon, which is indicated by the arrow. "HSE" refers to the heat shock responsive element from positions −653 to −631. The nucleotide sequence for the HSE (SEQ ID NO:4) is also set forth in the diagram. "STAT3" indicates the STAT3-binding element of the MUC1 promoter from nucleotide positions −515 to −494. "TATA" refers to the so-called TATA box, a highly conserved DNA binding motif recognized by the TATA-binding protein (TBP).

A. Methods of Screening for Inhibitory Compounds

1. The MUC1-HSF1 Interaction

The present invention provides in vitro methods (e.g, "screening methods") for identifying compounds (e.g., small molecules or macromolecules) that inhibit binding of an HSF (e.g., HSF1, HSF2, HSF3, HSF4, or a functional fragment of an HSF) to MUC1, and in particular, the MUC1-CD.

These methods can be performed using: (a) isolated MUC1 reagents and one or more isolated HSF reagents; or (b) cells expressing a MUC1 reagent and one or more HSF reagents.

The term "isolated" as applied to any of the polypeptide reagents described herein refers to a polypeptide, or a peptide fragment thereof, which either has no naturally-occurring counterpart or has been separated or purified from components which naturally accompany it, e.g., in tissues such as pancreas, liver, spleen, ovary, testis, muscle, joint tissue, neural tissue, gastrointestinal tissue or tumor tissue (e.g., breast cancer or colon cancer tissue), or body fluids such as blood, serum, or urine. Typically, the polypeptide or peptide fragment is considered "isolated" when it is at least 70%, by dry weight, free from the proteins and other naturally-occurring organic molecules with which it is naturally associated. Preferably, a preparation of a reagent is at least 80%, more preferably at least 90%, and most preferably at least 99%, by dry weight, the reagent. Since a polypeptide that is chemically synthesized is, by its nature, separated from the components that naturally accompany it, a synthetic polypeptide reagent is "isolated."

An isolated polypeptide reagent can be obtained, for example, by extraction from a natural source (e.g., from tissues); by expression of a recombinant nucleic acid encoding the polypeptide; or by chemical synthesis. A polypeptide reagent that is produced in a cellular system different from the source from which it naturally originates is "isolated," because it will necessarily be free of components which naturally accompany it. The degree of isolation or purity can be measured by any appropriate method, e.g., column chromatography, polyacrylamide gel electrophoresis, or HPLC analysis.

Prior to testing, any of the reagents described herein can undergo modification, e.g., phosphorylation or glycosylation, by methods known in the art.

In methods of screening for compounds that inhibit binding of an isolated MUC1 reagent to an isolated HSF reagent, a MUC1 reagent is contacted with an HSF reagent in the presence of one or more concentrations of a test compound and binding between the two reagents in the presence and absence of the test compound is detected, tested for, and/or measured. In such assays neither of the reagents need be detectably labeled. For example, by exploiting the phenomenon of surface plasmon resonance, the MUC1 reagent can be bound to a suitable solid substrate and an HSF reagent exposed to the substrate-bound MUC1 reagent in the presence and absence of the compound of interest. Binding of the HSF reagent to the MUC1 reagent on the solid substrate results in a change in the intensity of surface plasmon resonance that can be detected qualitatively or quantitatively by an appropriate instrument, e.g., a Biacore apparatus (Biacore International AB, Rapsgatan, Sweden). It will be appreciated that the experiment can be performed in reverse, i.e., with the HSF reagent bound to the solid substrate and the MUC1 reagent added to it in the presence of the test compound.

Moreover, assays to test for inhibition (or in some cases enhancement) of binding to MUC1 can involve the use, for example, of: (a) a single MUC1-specific "detection" antibody that is detectably labeled; (b) an unlabeled MUC1-specific antibody and a detectably labeled secondary antibody; or (c) a biotinylated MUC1-specific antibody and detectably labeled avidin. In addition, combinations of these approaches (including "multi-layer" assays) familiar to those in the art can be used to enhance the sensitivity of assays. In these assays, the HSF (e.g., HSF1, HSF2, HSF3, or HSF4) reagent can be immobilized on a solid substrate such as a nylon or nitrocellulose membrane by, for example, "spotting" an aliquot of a sample containing the reagent onto a membrane or by blotting onto a membrane an electrophoretic gel on which the sample or an aliquot of the sample has been subjected to electrophoretic separation. Alternatively, the HSF reagent can be bound to a plastic substrate (e.g., the plastic bottom of an ELISA (enzyme-linked immunosorbent assay) plate well) using methods known in the art. The substrate-bound reagent is then exposed to the MUC1 reagent in the presence and absence of the test compound. After incubating the resulting mixture for a period of time and at temperature optimized for the system of interest, the presence and/or amount of MUC1 reagent bound to the HSF test on the solid substrate is then assayed using a detection antibody that binds to the MUC1 reagent and, where required, appropriate detectably labeled secondary antibodies or avidin. It will be appreciated that instead of binding the HSF reagent to the solid substrate, the MUC1 reagent can be bound to it. In this case binding of the HSF reagent to the substrate-bound MUC1 is tested by obvious adaptations of the method described above for substrate-bound HSF reagent.

The invention also features "sandwich" assays. In these sandwich assays, instead of immobilizing reagents on solid substrates by the methods described above, an appropriate reagent can be immobilized on the solid substrate by, prior to exposing the solid substrate to the reagent, conjugating a "capture" reagent-specific antibody (polyclonal or mAb) to the solid substrate by any of a variety of methods known in the art. The reagent is then bound to the solid substrate by virtue of its binding to the capture antibody conjugated to the solid substrate. The procedure is carried out in essentially the same manner described above for methods in which the appropriate reagent is bound to the solid substrate by techniques not involving the use of a capture antibody. It is understood that in these sandwich assays, the capture antibody should not bind to the same epitope (or range of epitopes in the case of a polyclonal antibody) as the detection antibody. Thus, if a mAb is used as a capture antibody, the detection antibody can be either: (a) another mAb that binds to an epitope that is either completely physically separated from or only partially overlaps with the epitope to which the capture mAb binds; or (b) a polyclonal antibody that binds to epitopes other than or in addition to that to which the capture mAb binds. On the other hand, if a polyclonal antibody is used as a capture antibody, the detection antibody can be either (a) a mAb that binds to an epitope that is either completely physically separated from or partially overlaps with any of the epitopes to which the capture polyclonal antibody binds; or (b) a polyclonal antibody that binds to epitopes other than or in addition to that to which the capture polyclonal antibody binds. Assays which involve the use of a capture and a detection antibody include sandwich ELISA assays, sandwich Western blotting assays, and sandwich immunomagnetic detection assays.

Suitable solid substrates to which the capture antibody can be bound include, without limitation, the plastic bottoms and sides of wells of microtiter plates, membranes such as nylon or nitrocellulose membranes, polymeric (e.g., without limitation, agarose, cellulose, or polyacrylamide) beads or particles.

Methods of detecting and/or for quantifying a detectable label depend on the nature of the label and are known in the art. Appropriate labels include, without limitation, radionuclides (e.g., $^{125}I$, $^{131}I$, $^{35}S$, $^{3}H$, $^{32}P$, or $^{14}C$), fluorescent reagents (e.g., fluorescein, rhodamine, or phycoerythrin), luminescent reagents (e.g., Qdot™ nanoparticles supplied by the Quantum Dot Corporation, Palo Alto, Calif.), compounds that absorb light of a defined wavelength, or enzymes (e.g., alkaline phosphatase or horseradish peroxidase). The products of reactions catalyzed by appropriate enzymes can be, without limitation, fluorescent, luminescent, or radioactive or they may absorb visible or ultraviolet light. Examples of detectors include, without limitation, x-ray film, radioactivity counters, scintillation counters, spectrophotometers, colorimeters, fluorometers, luminometers, and densitometers.

Candidate compounds can also be tested for their ability to inhibit binding of MUC1 to an HSF in cells. The cells can either naturally express an appropriate MUC1 reagent and/or an HSF reagent of interest (i.e., the cells encode an endogenous MUC1 and/or HSF gene which can be expressed to yield a MUC1 and/or HSF polypeptide or their functional fragments) or they can recombinantly express either or both reagents. The cells can be normal or malignant and of any histological type, e.g., without limitation, epithelial cells, fibroblasts, lymphoid cells, macrophages/monocytes, granulocytes, keratinocytes, neuronal cells, or muscle cells. Suitable cell lines include those recited in the examples, e.g., breast cancer or colon cancer cell lines. The test compound can be added to the solution (e.g., culture medium) containing the cells or, where the compound is a protein, the cells can recombinantly express it. The cells can optionally also be exposed to a stimulus of interest (e.g., IL-6, heat shock, a heregulin (HRG)) prior to or after exposure of the cells to the compound. Following incubation of cells expressing the reagents of interest in the absence or presence (optionally at various concentrations), physical association between the reagents can be determined microscopically using appropriately labeled antibodies specific for both reagents, e.g., by confocal microscopy. Alternatively, the cells can be lysed under non-dissociating conditions and the lysates tested for the presence of physically associated reagents. Such methods include adaptions of those described using isolated reagents. For example, an antibody specific for one of the two reagents (reagent 1) can be bound to a solid substrate (e.g., the bottom and sides of the well of a microtiter plate or a nylon membrane). After washing away unbound antibody, the solid substrate with bound antibody is contacted with the cell lysate. Any reagent 1 in the lysate, bound or not bound to the second reagent (reagent 2), will bind to the antibody specific for reagent 1 on the solid substrate. After washing away unbound lysate components, the presence of reagent 2 (bound via reagent 1 and the antibody specific for reagent 1 to the solid substrate) is tested for using a detectably labeled antibody (see above) specific for reagent 2. Alternatively, reagent 1 can be immunoprecipitated with an antibody specific for reagent 1 and the immunoprecipitated material can be subjected to electrophoretic separation (e.g., by polyacrylamide gel electrophoresis performed under non-dissociating conditions). The electrophoretic gel can then be blotted onto a membrane (e.g., a nylon or a nitrocellulose membrane) and any reagent 2 on the membrane detected and/or measured with a detectably labeled antibody (see above) specific for reagent 2 by any of the above-described methods. It is understood that in the above-described assays, reagent 1 can be either the MUC1 reagent or the HSF reagent or vice versa. The test compounds can bind to one or both of the MUC1 and HSF reagents.

Exemplary MUC1 reagents for use in the methods described above can include MUC1 reagents that contain the MUC1-cytoplasmic domain (CD), e.g., the human MUC1-CD depicted by SEQ ID NO:2 (or a functional fragment of the MUC1-CD, see FIG. 4B).

2. Inhibition of HSF-MUC1 Promoter Interactions

The present invention provides in vitro methods (e.g, "screening methods") for identifying compounds (e.g., small molecules or macromolecules) that inhibit binding of an HSF (e.g., HSF1, HSF2, HSF3, HSF4, or a functional fragment of an HSF) to a MUC1 promoter (e.g., the HSE of a MUC1 promoter).

These methods can be performed using: (a) isolated HSF reagents and one or more isolated MUC1 promoter reagents; or (b) cells expressing an HSF reagent and one or more MUC1 promoter reagents. The methods can also be performed in cell-free or cell-based systems using the aforementioned components and one or more isolated MUC1 reagents. For example, MUC1 can serve to enhance the interaction between an HSF and the MUC1 promoter. Thus, in tests to identify a compound capable of inhibiting the interaction between an HSF (e.g., HSF1, HSF2, HSF3, or HSF4 or functional fragment of any of these HSF polypeptides) and a MUC1 promoter, a MUC1 reagent (at one or more concentrations) can be included. The MUC1 reagent can be contacted with the HSF and MUC1 promoter reagents simultaneously, or the MUC1 reagent can be contacted first with the HSF reagent (e.g., to form a molecular complex containing both the HSF and MUC1) and then contacted with the MUC1 promoter reagent. It is understood that the invention embraces any other possible combination or order of addition that would be appropriate for a given test (e.g., contacting HSF1 and MUC1 promoter reagents first, followed by contacting with the MUC1 reagent). Exemplary MUC1 reagents to be used in such methods can include the MUC1-CD. Exemplary MUC1 promoter reagents include the human MUC1 promoter (e.g., the human MUC1 promoter region in SEQ ID NO:3) or an HSE of a MUC1 promoter (e.g., the HSE of the human MUC1 promoter of SEQ ID NO:4).

In methods of screening for compounds that inhibit binding of an isolated HSF reagent to an isolated MUC1 promoter reagent, an HSF reagent is contacted with a MUC1 promoter reagent in the presence of one or more concentrations of a test compound and binding between the two reagents in the presence and absence of the test compound is detected, tested for, and/or measured. As discussed above, the HSF1 reagent and MUC1 promoter reagent can be also be contacted in the presence of a MUC1 reagent. In such assays neither of the reagents need be detectably labeled. For example, by exploiting the phenomenon of surface plasmon resonance, the MUC1 promoter reagent can be bound to a suitable solid substrate (e.g., agarose or sepharose beads, plastic screening assay plate or well, or other solid-phase substrates such as nitrocellulose) and an HSF reagent exposed to the substrate-bound MUC1 promoter reagent in the presence and absence of the compound of interest. Binding of the HSF reagent to the MUC1 promoter reagent on the solid substrate results in a change in the intensity of surface plasmon resonance that can be detected qualitatively or quantitatively by an appropriate instrument, e.g., a Biacore apparatus. It will be appreciated that the experiment can be performed in reverse, i.e., with the HSF reagent bound to the solid substrate and the MUC1 promoter reagent added to it in the presence of the test compound.

Moreover, assays to test for inhibition (or in some cases enhancement) of HSF binding to a MUC1 promoter can involve the use, for example, of: (a) a single HSF-specific "detection" antibody that is detectably labeled; (b) an unlabeled HSF-specific antibody and a detectably labeled secondary antibody; or (c) a biotinylated HSF-specific antibody and detectably labeled avidin. In addition, combinations of these approaches (including "multi-layer" assays) familiar to those in the art can be used to enhance the sensitivity of assays. In these assays, the MUC1 promoter reagent (e.g., the heat shock element (HSE) of a MUC1 promoter such as the HSE of the human MUC1 promoter of SEQ ID NO:4) can be immobilized on a solid substrate such as a nylon or nitrocellulose membrane by, for example, "spotting" an aliquot of a sample containing the reagent onto a membrane or by blotting onto a membrane an electrophoretic gel on which the sample or an aliquot of the sample has been subjected to electrophoretic separation. Alternatively, the MUC1 promoter reagent can be bound to a plastic substrate (e.g., the plastic surface of an assay plate well such as a Costar 96-well assay plate (Corning Life Sciences Acton, Mass.)) using methods known in the art. The substrate-bound reagent is then exposed to the HSF reagent in the presence and absence of the test compound (also optionally with a MUC1 reagent). After incubating the resulting mixture for a period of time and at temperature optimized for the system of interest, the presence and/or amount of the HSF reagent bound to the MUC1 promoter test on the solid substrate is then assayed using a detection antibody that binds to the HSF reagent and, where required, appropriate detectably labeled secondary antibodies or avidin.

It will be appreciated that instead of binding the MUC1 promoter reagent to the solid substrate, the HSF (e.g., HSF1) reagent can be bound to the solid-phase substrate. In this case, binding of the MUC1 promoter reagent to the substrate-bound HSF (e.g., HSF1) reagent is tested by adaptations of the method described above for substrate-bound MUC1 promoter reagent. The MUC1 promoter reagent can itself be detectably labeled, for example, with a fluorescent, luminescent, or radioactive label such as $^{32}P$, $^{33}P$, $^{35}S$, $^{125}I$, or $^{3}H$. Suitable methods for labeling (e.g., end-labeling) nucleic acids with radioactive labels are well known in the art and are described in, e.g., Sambrook et al. (1989) *Molecular Cloning: A Laboratory Manual*. Second edition, Cold Spring Harbor Laboratory Press, Cold Spring Harbor, N.Y. Suitable methods and devices for detecting/measuring the detectable label are set forth above. By this approach, an observed reduction in the amount of detectable label associated with the substrate-bound HSF reagent in the presence of a compound as compared to in the absence of the compound indicates that the compound inhibits the interaction between HSF and the MUC1 promoter.

Gel-shift assays are also useful in detecting interactions between DNA-binding proteins and nucleic acids. Thus, such assays can be useful to determine whether a compound inhibits the interaction between HSF and MUC1 promoter. These assays can involve, for example, incubating a detectably-labeled MUC1 promoter reagent and the HSF reagent in the presence and absence of a candidate compound for a predetermined period of time (e.g., at least 15 minutes, at least 20 minutes, at least 25 minutes, at least 30 minutes, at least 35 minutes, at least 40 minutes, at least 45 minutes, at least 60 minutes, at least 60 minutes or more) and then subjecting the molecular complex to a cross-linking agent (e.g., by treatment with DMS and/or formaldehyde). Cross-linked DNA-protein complexes (e.g., complexes comprising the MUC1 promoter reagent and the HSF reagent) are then subjected to SDS-PAGE to resolve complexes by size. Protein-DNA complexes are generally retarded in the gel whereas unbound nucleic acid migrates more quickly in the gel, and thus can be differentially detected based on location. These methods are well known in the art and are described in, e.g., Giardana et al (1995) Mol. Cell. Biol. 15(5):2737-2744; Bevilacqua et al. (1997) Nucleic Acids Res. 25(7):1333-1338; and Alfieri et al. (1996) Biochem. J. 319:601-606. Where a lower amount of DNA-protein complexes (complexes comprising an HSF reagent and a MUC1 promoter reagent) occur in the presence of a candidate compound versus without the candidate compound, this indicates that the candidate compound is a compound that inhibits the interaction between HSF and the MUC1 promoter. As above, the nucleic acid (e.g., the MUC1 promoter reagent) can be detectably labeled (e.g., radionuclide, fluorescent or luminescent marker) or in some instances, the proteinaceous reagent (e.g., the HSF reagent) can be detectably labeled or itself otherwise detected by western blotting for the HSF protein (e.g., using an antibody specific for HSF protein).

3. Inhibition of STAT3-MUC1 Promoter Interactions

The present invention also provides in vitro methods (e.g., "screening methods") for identifying compounds (e.g., small molecules) that inhibit binding of STAT3 to a MUC1 promoter (e.g., the STAT3 of a MUC1 promoter).

These methods can be performed using: (a) isolated STAT3 reagents and one or more isolated MUC1 promoter reagents; or (b) cells expressing an STAT3 reagent and one or more MUC1 promoter reagents. The methods can also be performed in cell-free or cell-based systems using the aforementioned components and one or more isolated MUC1 reagents. For example, where the MUC1 can serve to enhance the interaction between the STAT3 and the MUC1 promoter, it can be useful to identify a compound capable of inhibiting the interaction between an STAT3 reagent and a MUC1 promoter reagent in the presence of a MUC1 reagent such as one comprising the MUC1-CD. The MUC1 reagent can be contacted with the STAT3 reagent and MUC1 promoter reagent simultaneously, or the MUC1 reagent can be contacted first with the STAT3 reagent (e.g., to form a molecular complex containing both the STAT3 and MUC1) and then contacted with the MUC1 promoter reagent. While not limited by any particular theory or mechanism, where cooperativity exists, or is likely to or suspected to exist, between the binding of more than one different transcription factors to MUC1 promoter elements, the additional transcription factors can also be contacted with the reagents of the assay in the presence and absence of a candidate compound. For example, the STAT3 and MUC1 promoter reagents can be contacted with an HSF reagent (e.g., HSF1 or a functional fragment thereof) in the presence or absence of a candidate compound. Optionally, a MUC1 reagent can also be contacted with the aforementioned proteins. It is understood that the invention embraces any other possible combination or order of addition that would be appropriate for a given test (e.g., contacting STAT3 and MUC1 promoter reagents first, followed by contacting with the MUC1 reagent; contacting the MUC1, STAT3, and HSF reagents first, followed by contacting the triprotein complex with the MUC1 promoter reagent). Exemplary MUC1 reagents to be used in such methods include the MUC1-CD or a functional fragment thereof (e.g., any of MUC1-CD reagents described herein). Exemplary MUC1 promoter reagents include the STAT3-binding element of a MUC1 promoter (e.g., the STAT3-binding element of the human MUC1 promoter of SEQ ID NO:5) or any of the exemplary MUC1 promoter reagents described above. Where two or more transcription factor reagents (e.g., HSF and STAT3) are used, it can be preferable to have a MUC1 promoter reagent that comprises both of the cognate binding sequences for the transcription factors (e.g., an HSE and STAT3-binding element).

Suitable methods of screening for compounds that inhibit an interaction between STAT3 and the MUC1 promoter can include any of the methods described above under "Inhibition of HSF-MUC1 promoter Interactions."

B. Methods of Designing and Producing Inhibitory Compounds

1. Compounds that Inhibit MUC1-HSF Interaction

The invention also relates to using MUC1 reagents and/or HSF (e.g., HSF1, HSF2, HSF3, or HSF4) reagents to predict or design compounds that can physically interact with MUC1 and/or an HSF (e.g., HSF1) and potentially thereby inhibit the interaction between these two polypeptides. Such compounds would be useful to inhibit the ability of MUC1 to promote cell survival (e.g., through inhibition of MUC1 effects on HSF activity). One of skill in the art would know how to use standard molecular modeling or other techniques to identify small molecules that would bind to "appropriate sites" on MUC1 and/or an HSF (e.g., HSF1). One such example is provided in Broughton (1997) Curr. Opin. Chem. Biol. 1, 392-398. Generally, an "appropriate site" on a MUC1 or an HSF (e.g., HSF1) is a site directly involved in the physical interaction between the two molecule types. However, an "appropriate site" can also be an allosteric site, i.e., a region of the molecule not directly involved in a physical interaction with another molecule (and possibly even remote from such a "physical interaction" site) but to which binding of a compound results (e.g., by the induction of a conformational change in the molecule) in inhibition of the binding of the molecule to another molecule.

By "molecular modeling" is meant quantitative and/or qualitative analysis of the structure and function of protein-protein physical interaction based on three-dimensional structural information and protein-protein interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods.

Methods of designing compounds that bind specifically (e.g., with high affinity) to the region of MUC1 that interacts with an HSF (i.e., the cytoplasmic domain of MUC1) or the region of an HSF that binds to MUC1 typically are also computer-based, and involve the use of a computer having a program capable of generating an atomic model. Computer programs that use X-ray crystallography data are particularly useful for designing such compounds. Programs such as Ras-Mol, for example, can be used to generate a three dimensional model of, e.g., the region of MUC1 that interacts with an HSF (e.g., HSF1) or the region of an HSF (e.g., HSF1) that binds to MUC1 and/or determine the structures involved in MUC1-HSF binding. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures. Compounds can be designed using, for example, computer hardware or software, or a combination of both. However, designing is preferably implemented in one or more computer programs executing on one or more programmable computers, each containing a processor and at least one input device. The computer(s) preferably also contain(s) a data storage system (including volatile and non-volatile memory and/or storage elements) and at least one output device. Program code is applied to input data to perform the functions described above and generate output information. The output information is applied to one or more output devices in a known fashion. The computer can be, for example, a personal computer, microcomputer, or work station of conventional design.

Each program is preferably implemented in a high level procedural or object oriented programming language to communicate with a computer system. However, the programs can be implemented in assembly or machine language, if desired. In any case, the language can be a compiled or interpreted language.

Each computer program is preferably stored on a storage media or device (e.g., ROM or magnetic diskette) readable by a general or special purpose programmable computer. The computer program serves to configure and operate the computer to perform the procedures described herein when the program is read by the computer. The method of the invention can also be implemented by means of a computer-readable storage medium, configured with a computer program, where the storage medium so configured causes a computer to operate in a specific and predefined manner to perform the functions described herein.

For example, the computer-requiring steps in a method of designing a compound can involve:

(a) inputting into an input device, e.g., through a keyboard, a diskette, or a tape, data (e.g. atomic coordinates) that define the three-dimensional (3-D) structure of a first molecule (e.g., MUC1 or a part of MUC1 such as the MUC1-CD) that is known, or predicted, to bind to a second molecule (e.g., an HSF (e.g., HSF1) or a part thereof) or a molecular complex (e.g., MUC1, or a part thereof, predicted to bind to an HSF (e.g., HSF1), or a part thereof, or MUC1 bound to a macromolecular HSF complex), e.g., a region of MUC1 that interacts with an HSF (i.e., the cytoplasmic domain of MUC1), the region of an HSF that binds to MUC1, or all or a part (e.g., the cytoplasmic domain) of MUC1 bound to all or a part of an HSF (e.g., HSF1); and (b) determining, using a processor, the 3-D structure (e.g., an atomic model) of: (i) the site on the first molecule involved, or predicted to be involved, in binding to the second molecule; or (ii) one or more sites on the molecular components of molecular complex of interaction between molecular components of the molecular complex.

From the information obtained in this way, one skilled in the art will be able to design and make inhibitory compounds (e.g., peptides, non-peptide small molecules, aptamers (e.g., nucleic acid aptamers) with the appropriate 3-D structure (see "Methods of Making Inhibitory Compounds and Proteins Useful for the Invention" below).

Moreover, if computer-usable 3-D data (e.g., x-ray crystallographic or nuclear magnetic resonance (NMR) data) for a candidate compound are available, the following computer-based steps can be performed in conjunction with computer-based steps (a) and (b) described above: (c) inputting into an input device, e.g., through a keyboard, a diskette, or a tape, data (e.g. atomic coordinates) that define the three-dimensional (3-D) structure of a candidate compound; (d) determining, using a processor, the 3-D structure (e.g., an atomic model) of the candidate compound; (e) determining, using the processor, whether the candidate compound binds to the site on the first molecule or the one or more sites on the molecular components of the molecular complex; and (f) identifying the candidate compound as compound that inhibits the interaction between the first and second molecule or the between the molecular components of the molecular complex.

The method can involve the additional step of outputting to an output device a model of the 3-D structure of the compound. In addition, the 3-D data of candidate compounds can be compared to a computer database of, for example, 3-D structures (e.g., of MUC1, the cytoplasmic domain of MUC1, HSF (e.g., HSF1), or a MUC1-binding fragment of an HSF) stored in a data storage system.

Compounds useful for the invention also may be interactively designed from structural information of the compounds described herein using other structure-based design/modeling techniques (see, e.g., Jackson (1997) *Seminars in Oncology* 24:L164-172; and Jones et al. (1996) *J. Med. Chem.* 39:904-917). Compounds and polypeptides of the invention also can be identified by, for example, identifying candidate compounds by computer modeling as fitting spatially and preferentially (i.e., with high affinity) into the appropriate acceptor sites on MUC1 or an HSF (e.g., HSF1).

Candidate compounds identified as described above can then be tested in standard cellular or cell-free binding or binding inhibition assays familiar to those skilled in the art. Exemplary assays are described herein.

A candidate compound whose presence requires at least 2-fold (e.g., 4-fold, 6-fold, 10-fold, 100-fold, 1000-fold, 10,000 fold, or 100,000-fold) more of a given MUC1 reagent to achieve a defined arbitrary level of binding to a fixed amount of an HSF reagent than is achieved in the absence of the compound can be useful for inhibiting the interaction between MUC1 and the relevant HSF, and thus can be useful as a cancer therapeutic or prophylactic agent. Alternatively, a candidate compound whose presence requires at least 2-fold (e.g., 2-fold, 4-fold, 6-fold, 10-fold, 100-fold, 1000-fold, 10,000 fold, or 100,000-fold) more of a given HSF reagent to achieve a defined arbitrary level of binding to a fixed amount of a MUC1 reagent than is achieved in the absence of the compound can be useful for inhibiting the interaction between MUC1 and the relevant HSF, and thus can be useful as a cancer therapeutic or prophylactic agent.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., International Patent Application No. PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSSTER (Modeling Of New Structures from Secondary and Tertiary Restraints) (see, e.g., International Application No. PCT/US99/11913, the disclosure of which is incorporated herein by reference in its entirety). Other molecular modeling techniques may also be employed in accordance with this invention [e.g., Cohen et al. (1990) J. Med. Chem. 33: 883-894; Navia et al (1992) Current Opinions in Structural Biology, 2, pp. 202-210, the disclosures of which are incorporated herein by reference in its entirety]. All these methods produce data that are amenable to computer analysis. Other spectroscopic methods that can also be useful in the method of the invention, but that do not currently provide atomic level structural detail about biomolecules, include circular dichroism and fluorescence and ultraviolet/visible light absorbance spectroscopy. A preferred method of analysis is x-ray crystallography. Descriptions of this procedure and of NMR spectroscopy are provided below.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., International Patent Application No. PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSSTER (Modeling Of New Structures from Secondary and Tertiary Restraints) (see, e.g., International Application No. PCT/US99/11913, the disclosure of which is incorporated herein by reference in its entirety). Other molecular modeling techniques may also be employed in accordance with this invention [e.g., Cohen et al. (1990) J. Med. Chem. 33: 883-894; Navia et al (1992) Current Opinions in Structural Biology, 2, pp. 202-210, the disclosures of which are incorporated herein by reference in its entirety]. All these methods produce data that are amenable to computer analysis. Other spectroscopic methods that can also be useful in the method of the invention, but that do not currently provide atomic level structural detail about biomolecules, include circular dichroism and fluorescence and ultraviolet/visible light absorbance spectroscopy. A preferred method of analysis is x-ray crystallography. Descriptions of this procedure and of NMR spectroscopy are provided below.

2. Compounds that Inhibit MUC1-STAT3 Interaction

The invention also relates to using MUC1 reagents and/or STAT3 (e.g., human STAT3) reagents to predict or design compounds that can physically interact with MUC1 and/or STAT3 and potentially thereby inhibit the interaction between these two polypeptides. Such compounds would be useful to inhibit the ability of MUC1 to promote cell survival (e.g., through inhibition of MUC1 effects on STAT3 activity). It is understood that methods similar to those described above under "Compounds that Inhibit MUC1-HSF Interaction" can be used to design and generate compounds that inhibit an interaction between MUC1 and STAT3.

3. Compounds that Inhibit HSF-MUC1 Promoter Interaction

The invention also relates to using HSF (e.g., HSF1, HSF2, HSF3, or HSF4) reagents and/or MUC1 promoter reagents to predict or design compounds that can interact with an HSF (e.g., HSF1) and/or a MUC1 promoter (e.g., the HSE of a MUC1 promoter) and potentially thereby inhibit the interaction between these two polypeptides. The methods can also involve using additional reagents such as MUC1 reagents to predict or design compounds that interact with an HSF or MUC1 promoter. Such compounds would be useful to inhibit the ability of MUC1 to promote cell survival (e.g., through inhibition HSF-mediated upregulation of MUC1 following heat shock or HRG treatment). One of skill in the art would know how to use standard molecular modeling or other techniques (e.g., obvious adaptations of methods described above) to identify small molecules that would bind to "appropriate sites" on HSF (e.g., HSF1) or a MUC1 promoter (e.g., an HSE element of a MUC1 promoter). Example structures of an HSF (e.g., homologous HSF proteins from bacteria and yeast) useful in the methods are set forth in, e.g., Harrison et al. (1994) Science 263(5144):224-227 and Littlefield et al. (2000) Nat. Struct. Biol. 7(4):261-262. Generally, an "appropriate site" on an HSF (e.g., HSF1) and/or a MUC1 promoter is a site directly involved in the physical interaction between the two molecule types. As pointed out above, an "appropriate site" can also be an allosteric site, i.e., a region of the molecule not directly involved in a physical interaction with another molecule.

Methods of designing compounds that bind specifically (e.g., with high affinity) to the region of an HSF (e.g., HSF1) that interacts with a MUC1 promoter (i.e., DNA-binding domain of an HSF) or the region of a MUC1 promoter (e.g., the HSE of a MUC1 promoter) that is bound by an HSF (e.g., HSF1) typically are also computer-based, and can involve the use of a computer as described above. Compounds can be designed using, for example, computer hardware or software, or a combination of both, as described above.

Compounds useful for the invention also can be interactively designed from structural information of the compounds described herein using other structure-based design/modeling techniques as above. For example, compounds and polypeptides of the invention also can be identified by identifying candidate compounds by computer modeling as fitting spatially and preferentially (i.e., with high affinity) into the appropriate acceptor sites on an HSF (e.g., HSF1) or a MUC1 promoter (e.g., an HSE of a MUC1 promoter).

Candidate compounds identified as described above can then be tested in standard cellular or cell-free binding or binding inhibition assays familiar to those skilled in the art as described above.

4. Compounds that Inhibit STAT3-MUC1 Promoter Interaction

The invention also relates to using STAT3 and/or MUC1 promoter reagents to predict or design compounds that can interact with a STAT3 and/or a MUC1 promoter (e.g., the STAT3-binding element of a MUC1 promoter) and potentially thereby inhibit the interaction between these two polypeptides. The methods can further include using additional reagents such as MUC1 reagents and/or HSF1 reagents to predict or design compounds that interact with a STAT3 or MUC1 promoter. Such compounds would be useful to inhibit the ability of MUC1 to promote cell survival (e.g., through inhibition of STAT3-mediated upregulation of MUC1 following IL-6 treatment). One of skill in the art would know how to use standard molecular modeling or other techniques (e.g., an obvious adapatation of methods described above) to identify small molecules that would bind to "appropriate sites" on STAT3 or a MUC1 promoter (e.g., a STAT3-binding element of a MUC1 promoter). Example structures of a STAT3 (e.g., STAT3 bound to DNA) useful in the methods are set forth in, e.g., Becker et al. (1998) Nature 394(6689):145-151. Generally, an "appropriate site" on STAT3 and/or a MUC1 promoter (e.g., the STAT3-binding element of a MUC1 promoter) is a site directly involved in the physical interaction between the two molecule types. As pointed out above, an "appropriate site" can also be an allosteric site, i.e., a region of the molecule not directly involved in a physical interaction with another molecule.

Methods of designing compounds that bind specifically (e.g., with high affinity) to the region of STAT3 that interacts with the MUC1 promoter (i.e., the DNA-binding domain of STAT3) or the region of the MUC1 promoter (e.g., the STAT3-binding domain of STAT3) that is bound by STAT3 typically are also computer-based, and can involve the use of a computer as described above. Compounds can be designed using, for example, computer hardware or software, or a combination of both, as described above.

Compounds useful for the invention also can be interactively designed from structural information of the compounds described herein using other structure-based design/modeling techniques as above. For example, compounds and polypeptides of the invention also can be identified by identifying candidate compounds by computer modeling as fitting spatially and preferentially (i.e., with high affinity) into the appropriate acceptor sites on STAT3 or a MUC1 promoter (e.g., a STAT3-binding element of a MUC1 promoter).

Candidate compounds identified as described above can then be tested for their ability to, e.g., inhibit the binding of STAT3 to a MUC1 promoter in standard cellular or cell-free binding or binding inhibition assays familiar to those skilled in the art as described herein (see below).

5. X-Ray Crystallography

X-ray crystallography is based on the diffraction of x-radiation of a characteristic wavelength by electron clouds surrounding the atomic nuclei in a crystal of a molecule or molecular complex of interest. The technique uses crystals of purified biological macromolecules or molecular complexes (but these frequently include solvent components, co-factors, substrates, or other ligands) to determine near atomic resolution of the atoms making up the particular biological macromolecule. A prerequisite for solving 3-D structure by x-ray crystallography is a well-ordered crystal that will diffract x-rays strongly. The method directs a beam of x-rays onto a regular, repeating array of many identical molecules so that the x-rays are diffracted from the array in a pattern from which the structure of an individual molecule can be retrieved. Well-ordered crystals of, for example, globular protein molecules are large, spherical or ellipsoidal objects with irregular surfaces. The crystals contain large channels between the individual molecules. These channels, which normally occupy more than one half the volume of the crystal, are filled with disordered solvent molecules, and the protein molecules are in contact with each other at only a few small regions. This is one reason why structures of proteins in crystals are generally the same as those of proteins in solution.

Methods of obtaining the proteins of interest are described below. The formation of crystals is dependent on a number of different parameters, including pH, temperature, the concentration of the biological macromolecule, the nature of the solvent and precipitant, as well as the presence of added ions or ligands of the protein. Many routine crystallization experiments may be needed to screen all these parameters for the combinations that give a crystal suitable for x-ray diffraction analysis. Crystallization robots can automate and speed up work of reproducibly setting up a large number of crystallization experiments (see, e.g., U.S. Pat. No. 5,790,421, the disclosure of which is incorporated herein by reference in its entirety). Polypeptide crystallization occurs in solutions in which the polypeptide concentration exceeds it's solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Crystallizations are generally carried out between 4° C. and 20° C. Substances known as "precipitants" are often used to decrease the solubility of the polypeptide in a concentrated solution by forming an energetically unfavorable precipitating depleted layer around the polypeptide molecules [Weber (1991) Advances in Protein Chemistry, 41:1-36]. In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2-4 pentanediol, and many of the polyglycols, such as polyethylene glycol (PEG). The precipitating solutions can include, for example, 13-24% PEG 4000, 5-41% ammonium sulfate, and 1.0-1.5 M sodium chloride, and a pH ranging from 5-7.5. Other additives can include 0.1 M HEPES, 2-4% butanol, 0.1 M or 20 mM sodium acetate, 50-70 mM citric acid, 120-130 mM sodium phosphate, 1 mM ethylene diamine tetraacetic acid (EDTA), and 1 mM dithiothreitol (DTT). These agents are prepared in buffers and are added dropwise in various combinations to the crystallization buffer.

Commonly used polypeptide crystallization methods include the following techniques: batch, hanging drop, seed initiation, and dialysis. In each of these methods, it is important to promote continued crystallization after nucleation by maintaining a supersaturated solution. In the batch method, polypeptide is mixed with precipitants to achieve supersaturation, and the vessel is sealed and set aside until crystals appear. In the dialysis method, polypeptide is retained in a sealed dialysis membrane that is placed into a solution containing precipitant. Equilibration across the membrane increases the polypeptide and precipitant concentrations, thereby causing the polypeptide to reach supersaturation levels.

In the preferred hanging drop technique [McPherson (1976) J. Biol. Chem., 251:6300-6306], an initial polypeptide mixture is created by adding a precipitant to a concentrated polypeptide solution. The concentrations of the polypeptide and precipitants are such that, in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the second solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide may form.

Another method of crystallization introduces a nucleation site into a concentrated polypeptide solution. Generally, a concentrated polypeptide solution is prepared and a seed crystal of the polypeptide is introduced into this solution. If the concentrations of the polypeptide and any precipitants are correct, the seed crystal will provide a nucleation site around which a larger crystal forms.

Yet another method of crystallization is an electrocrystallization method in which use is made of the dipole moments of protein macromolecules that self-align in the Helmholtz layer adjacent to an electrode (see, e.g., U.S. Pat. No. 5,597,457, the disclosure of which is incorporated herein by reference in its entirety).

Some proteins may be recalcitrant to crystallization. However, several techniques are available to the skilled artisan to induce crystallization. For example, the removal of flexible polypeptide segments at the amino or carboxyl terminal end of the protein may facilitate production of crystalline protein samples. Removal of such segments can be done using molecular biology techniques or treatment of the protein with proteases such as trypsin, chymotrypsin, or subtilisin.

In diffraction experiments, a narrow and parallel beam of x-rays is taken from the x-ray source and directed onto the crystal to produce diffracted beams. The incident primary beams cause damage to both the macromolecule and solvent molecules. The crystal is, therefore, cooled (e.g., to −220° C. to −50° C.) to prolong its lifetime. The primary beam must strike the crystal from many directions to produce all possible diffraction spots, so the crystal is rotated in the beam during the experiment. The diffracted spots are recorded on a film or by an electronic detector. Exposed film has to be digitized and quantified in a scanning device, whereas the electronic detectors feed the signals they detect directly into a computer. Electronic area detectors significantly reduce the time required to collect and measure diffraction data. Each diffraction beam, which is recorded as a spot on film, is defined by three properties: the amplitude, which is measured from the intensity of the spot; the wavelength, which is set by the x-ray source; and the phase, which is lost in x-ray experiments. All three properties are needed for all of the diffracted beams in order to determine the positions of the atoms giving rise to the diffracted beams. One way of determining the phases is called Multiple Isomorphous Replacement (MIR), which requires the introduction of exogenous x-ray scatterers (e.g., heavy atoms such metal atoms) into the unit cell of the crystal. For a more detailed description of MIR, see U.S. Pat. No. 6,093,573 (column 15) the disclosure of which is incorporated herein by reference in its entirety.

Atomic coordinates refer to Cartesian coordinates (x, y, and z positions) derived from mathematical equations involving Fourier synthesis of data derived from patterns obtained via diffraction of a monochromatic beam of x-rays by the atoms (scattering centers) of biological macromolecule of interest in crystal form. Diffraction data are used to calculate electron density maps of repeating units in the crystal (unit cell). Electron density maps are used to establish the positions (atomic coordinates) of individual atoms within a crystal's unit cell. The absolute values of atomic coordinates convey spatial relationships between atoms because the absolute values ascribed to atomic coordinates can be changed by rotational and/or translational movement along x, y, and/or z axes, together or separately, while maintaining the same relative spatial relationships among atoms. Thus, a biological macromolecule (e.g., a protein) whose set of absolute atomic coordinate values can be rotationally or translationally adjusted to coincide with a set of prior determined values from an analysis of another sample is considered to have the same atomic coordinates as those obtained from the other sample.

Further details on x-ray crystallography can be obtained from co-pending U.S. application Ser. No. 10/486,278, U.S. Pat. No. 6,093,573 and International Application Nos. PCT/US99/18441, PCT/US99/11913, and PCT/US00/03745. The disclosures of all these patent documents are incorporated herein by reference in their entirety.

6. NMR Spectroscopy

While x-ray crystallography requires single crystals of a macromolecule of interest, NMR measurements are carried out in solution under near physiological conditions. However, NMR-derived structures are not as detailed as crystal-derived structures.

While the use of NMR spectroscopy was until relatively recently limited to the elucidation of the 3-D structure of relatively small molecules (e.g., proteins of 100-150 amino acid residues), recent advances including isotopic labeling of the molecule of interest and transverse relaxation-optimized spectroscopy (TROSY) have allowed the methodology to be extended to the analysis of much larger molecules, e.g., proteins with a molecular weight of 110 kDa [Wider (2000) BioTechniques, 29:1278-1294].

NMR uses radio-frequency radiation to examine the environment of magnetic atomic nuclei in a homogeneous magnetic field pulsed with a specific radio frequency. The pulses perturb the nuclear magnetization of those atoms with nuclei of nonzero spin. Transient time domain signals are detected as the system returns to equilibrium. Fourier transformation of the transient signal into a frequency domain yields a one-dimensional NMR spectrum. Peaks in these spectra represent chemical shifts of the various active nuclei. The chemical shift of an atom is determined by its local electronic environment. Two-dimensional NMR experiments can provide information about the proximity of various atoms in the structure and in three dimensional space. Protein structures can be determined by performing a number of two- (and sometimes 3- or 4-) dimensional NMR experiments and using the resulting information as constraints in a series of protein folding simulations.

More information on NMR spectroscopy including detailed descriptions of how raw data obtained from an NMR experiment can be used to determine the 3-D structure of a macromolecule can be found in: Protein NMR Spectroscopy, Principles and Practice, J. Cavanagh et al., Academic Press, San Diego, 1996; Gronenbom et al. (1990) Anal. Chem. 62(1):2-15; and Wider (2000), supra., the disclosures of all of which are incorporated herein by reference in their entirety Any available method can be used to construct a 3-D model of a region of (i) MUC1 and/or an HSF (e.g., HSF1); (ii) MUC1 and/or STAT3; (iii) an HSF (e.g., HSF1) and/or a MUC1 promoter (e.g., an HSE of a MUC1 promoter); or (iv) STAT3 and/or a MUC1 promoter (e.g., the STAT3-binding element of a MUC1 promoter) of interest from the x-ray crystallographic and/or NMR data using a computer as described above. Such a model can be constructed from analytical data points inputted into the computer by an input device and by means of a processor using known software packages, e.g., HKL, MOSFILM, XDS, CCP4, SHARP, PHASES, HEAVY, XPLOR, TNT, NMRCOMPASS, NMRPIPE, DIANA, NMRDRAW, FELIX, VNMR, MADIGRAS, QUANTA, BUSTER, SOLVE, O, FRODO, or CHAIN. The model constructed from these data can be visualized via an output device of a computer, using available systems, e.g., Silicon Graphics, Evans and Sutherland, SUN, Hewlett Packard, Apple Macintosh, DEC, IBM, or Compaq.

C. Compounds

Compounds identified in any of the methods described herein, or any compound with appropriate activity useful in any of the methods described herein, include various chemical classes. Compounds can be biomolecules including, but not limited to, small molecules, peptides, polypeptides, peptidomimetics (e.g., peptoids), amino acids, aptamers, amino acid analogs, saccharides, fatty acids, steroids, purines, pyrimidines, derivatives or structural analogues thereof, polynucleotides, and polynucleotide analogs. Compounds can be both small or large molecule compounds.

Typically small molecule compounds are relatively small organic molecules having a molecular weight in the range of about 50 to 2,500 daltons. These compounds can comprise functional groups necessary for structural interaction with proteins (e.g., hydrogen bonding), and can include at least an amine, carbonyl, hydroxyl, or carboxyl group, and preferably at least two of the functional chemical groups. These compounds can often comprise cyclical carbon or heterocyclic structures and/or aromatic or polyaromatic structures (e.g., purine core) substituted with one or more of the above functional groups.

Also of interest as small molecule compounds in some of the methods described herein are nucleic acid aptamers, which are relatively short nucleic acid (DNA, RNA or a combination of both) sequences that bind with high avidity to a variety of proteins and inhibit the binding to such proteins of ligands, receptors, and other molecules. Aptamers are generally about 25-40 nucleotides in length and have molecular weights in the range of about 18-25 kDa. Aptamers with high specificity and affinity for targets can be obtained by an in vitro evolutionary process termed SELEX (systemic evolution of ligands by exponential enrichment) [see, for example, Zhang et al. (2004) Arch. Immunol. Ther. Exp. 52:307-315, the disclosure of which is incorporated herein by reference in its entirety]. For methods of enhancing the stability (by using nucleotide analogs, for example) and enhancing in vivo bioavailability (e.g., in vivo persistence in a subject's circulatory system) of nucleic acid aptamers see Zhang et al. (2004) and Brody et al. [(2000) Reviews in Molecular Biotechnology 74:5-13, the disclosure of which is incorporated herein by reference in its entirety].

Large molecule compounds can include large proteins such as antibodies (see below) or macromolecular complexes comprising two or more proteins.

Compounds can be identified from a number of potential sources, including: chemical libraries, natural product libraries, and combinatorial libraries comprised of random peptides, oligonucleotides, or organic molecules. Chemical libraries consist of random chemical structures, some of which are analogs of known compounds or analogs or compounds that have been identified as "hits" or "leads" in other drug discovery screens, while others are derived from natural products, and still others arise from non-directed synthetic organic chemistry. Natural product libraries are collections of microorganisms, animals, plants, or marine organisms which are used to create mixtures for screening by: (1) fermentation and extraction of broths from soil, plant or marine microorganisms, or (2) extraction of plants or marine organisms. Natural product libraries include polypeptides, non-ribosomal peptides, and variants (non-naturally occurring) thereof. For a review, see Science 282:63-68 (1998). Combinatorial libraries are composed of large numbers of peptides, oligonucleotides, or organic compounds as a mixture. These libraries are relatively easy to prepare by traditional automated synthesis methods, PCR, cloning, or proprietary synthetic methods. Of particular interest are non-peptide combinatorial libraries.

Still other libraries of interest include peptide, protein, peptidomimetic, multiparallel synthetic collection, recombinatorial, and polypeptide libraries. For a review of combinatorial chemistry and libraries created therefrom, see Myers, Curr. Opin. Bioechnol. 8:701-707 (1997).

Identification of test compounds through the use of the various libraries described herein permits subsequent modification of the test compound "hit" or "lead" to optimize the capacity of the "hit" or "lead" to inhibit the interaction between, e.g., an HSF1 and MUC1, an HSF1 and a MUC1 promoter, or STAT3 and a MUC1 promoter.

Inhibitory compounds can be large molecules such as antibodies, or antigen-binding antibody fragments, specific for, e.g., MUC1, an HSF, or STAT3. Such antibodies will generally bind to, or close to: (a) the region of MUC1 to which an HSF (e.g., HSF1) binds (e.g., MUC1-CD); (b) the region on an HSF to which MUC1 binds; (c) the region of MUC1 to which STAT3 binds; or (d) the region of STAT3 to which MUC1 binds. However, as indicated above, the compounds can also act allosterically and so they can also bind to the proteins at positions other than, and even remote from, the binding sites for MUC1 (on an HSF such as HSF1) and on an HSF (e.g., HSF1) (for MUC1 or a MUC1-CD). Antibodies could also, e.g., bind to the DNA binding domain of HSF or STAT3 and thus prevent the binding of these molecules to a MUC1 promoter. As used throughout the present application, the term "antibody" refers to a whole antibody (e.g., IgM, IgG, IgA, IgD, or IgE) molecule that is generated by any one of a variety of methods that are known in the art. The antibody can be made in or derived from any of a variety of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

The antibody can be a purified or a recombinant antibody. Also useful for the invention are antibody fragments and chimeric antibodies and humanized antibodies made from non-human (e.g., mouse, rat, gerbil, or hamster) antibodies. As used herein, the term "antibody fragment" refers to an antigen-binding fragment, e.g., Fab, F(ab')$_2$, Fv, and single chain Fv (scFv) fragments. An scFv fragment is a single polypeptide chain that includes both the heavy and light chain variable regions of the antibody from which the scFv is derived. In addition, diabodies [Poljak (1994) Structure 2(12):1121-1123; Hudson et al. (1999) J. Immunol. Methods 23(1-2):177-189, the disclosures of both of which are incorporated herein by reference in their entirety] and intrabodies [Huston et al. (2001) Hum. Antibodies 10(3-4):127-142; Wheeler et al. (2003) Mol. Ther. 8(3):355-366; Stocks (2004) Drug Discov. Today 9(22): 960-966, the disclosures of all of which are incorporated herein by reference in their entirety] can be used in the methods of the invention.

Antibody fragments that contain the binding domain of the molecule can be generated by known techniques. For example: F(ab')$_2$ fragments can be produced by pepsin digestion of antibody molecules; and Fab fragments can be generated by reducing the disulfide bridges of F(ab')$_2$ fragments or by treating antibody molecules with papain and a reducing agent. See, e.g., National Institutes of Health, *Current Protocols In Immunology*, Coligan et al., ed. 2.8, 2.10 (Wiley Interscience, 1991) the disclosure of which is incorporated herein by reference in their entirety. scFv fragments can be produced, for example, as described in U.S. Pat. No. 4,642,334, the disclosure of which is incorporated herein by reference in its entirety.

Chimeric and humanized monoclonal antibodies can be produced by recombinant DNA techniques known in the art, for example, using methods described in Robinson et al., International Patent Publication PCT/US86/02269; Akira et al., European Patent Application 184,187; Taniguchi, European Patent Application 171,496; Morrison et al., European Patent Application 173,494; Neuberger et al., PCT Application WO 86/01533; Cabilly et al., U.S. Pat. No. 4,816,567; Cabilly et al., European Patent Application 125,023; Better et al. (1988) Science 240, 1041-43; Liu et al. (1987) J. Immunol. 139, 3521-26; Sun et al. (1987) PNAS 84, 214-18; Nishimura et al. (1987) Canc. Res. 47, 999-1005; Wood et al. (1985) Nature 314, 446-49; Shaw et al. (1988) J. Natl. Cancer Inst. 80, 1553-59; Morrison, (1985) Science 229, 1202-07; Oi et al (1986) BioTechniques 4, 214; Winter, U.S. Pat. No. 5,225, 539; Jones et al. (1986) Nature 321, 552-25; Veroeyan et al. (1988) Science 239, 1534; and Beidler et al. (1988) J. Immunol. 141, 4053-60. The disclosures of all these articles and patent documents are incorporated herein by reference in their entirety.

The compounds identified above can be synthesized by any chemical or biological method. The compounds identified above can also be pure, or can be in a formuation (e.g., a pharmaceutical composition) with one or more additional non-active ingredients (e.g., additional compounds or constituents which do not bind to or inhibit the interaction between an HSF (e.g., HSF1) and MUC1 (e.g., MUC1-CD); MUC1 and STAT3, an HSF and a MUC1 promoter; or STAT3 and a MUC1 promoter), and can be prepared in an assay-, physiologic-, or pharmaceutically-acceptable diluent or carrier (see Pharmaceutical Compositions and Methods of Treatment below). A composition can also contain one or more additional therapeutic agents (see below).

D. Pharmaceutical Compositions and Methods of Treatment

The present invention also provides for pharmaceutical compositions comprising one or more therapeutically effective amounts of a compound, or a pharmaceutically acceptable salt thereof, together with a pharmaceutically acceptable carrier, diluent, or excipient therefor. A compound that has the ability to, for example, (a) inhibit the interaction between MUC1 and an HSF (e.g., HSF1), (b) inhibit the interaction between MUC1 and STAT3, (c) inhibit the interaction of an HSF (e.g., HSF1) with a MUC1 promoter, (d) inhibit the interaction between STAT3 and a MUC1 promoter, (e) inhibit MUC1 expression, (f) inhibit the growth of a cell (e.g., a colon cancer cell, a breast cancer cell, a prostate cancer cell, a lung cancer cell, a lymphoma, or an immune cell such as a proliferating B- or T-cell), (g) inhibit the interaction between a heregulin and a human epidermal growth factor receptor, (h) inhibit a HER, (i) inhibit the interaction between IL-6 and IL-6R, or (j) inhibit IL-6R can be considered a compound. Such compounds can be, but are not necessarily, those identified by any of the screening methods described herein.

Any of the compounds described herein can be incorporated into pharmaceutical compositions. Such compositions typically include the compound and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. A compound of the present invention can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc. Supplementary active compounds can also be incorporated into the compositions.

A pharmaceutical composition is formulated to be compatible with its intended route of administration. Examples of routes of administration include oral, rectal, and parenteral, e.g., intravenous, intramuscular, intradermal, subcutaneous, inhalation, transdermal, or transmucosal. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The compositions can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL3 (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be desirable to include isotonic agents, for example, sugars, polyalcohols such as manitol, sorbitol, sodium chloride in the composition. Prolonged absorption of the injectable compositions can be facilitated by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the methods of preparation can include vacuum drying or freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The powders and tablets contain from 1% to 95% (w/w) of the active compound. In certain embodiments, the active compound ranges from 5% to 70% (w/w). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811 (hereby specifically incorporated by reference).

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. Dosage units can also be accompanied by instructions for use.

The dose administered to a subject, in the context of the present invention should be sufficient to affect a beneficial therapeutic response in the subject over time. The term "subject" refers to a member of the class Mammalia. Examples of mammals include, without limitation, humans (e.g., a human patient), non-human primates (e.g., chimpanzees, baboons, or monkeys), mice, rats, rabbits, guinea pigs, gerbils, hamsters, horses, livestock (e.g., cows, pigs, sheep, or goats), dogs, cats, or whales.

The dose will be determined by the efficacy of the particular compound employed and the condition of the subject, as well as the body weight or surface area of the subject to be treated. The size of the dose also will be determined by the existence, nature, and extent of any adverse side effects that accompany the administration of a particular compound in a particular subject. In determining the effective amount of the compound to be administered in the treatment or prophylaxis of the disease being treated, the physician can evaluate factors such as the circulating plasma levels of the compound, compound toxicities, and/or the progression of the disease, etc. In general, the dose equivalent of a compound is from about 1 µg/kg to 100 mg/kg for a typical subject. Many different administration methods are known to those of skill in the art.

For administration, compounds of the present invention can be administered at a rate determined by factors that can include, but are not limited to, the pharmacokinetic profile of the compound, contraindicated drugs, and the side effects of the compound at various concentrations, as applied to the mass and overall health of the subject. Administration can be accomplished via single or divided doses.

Toxicity and therapeutic efficacy of such compounds can be determined by known pharmaceutical procedures in, for example, cell cultures or experimental animals (animal models of cancer, e.g., colon, breast, prostate, or lung cancer models). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in to minimize potential damage to normal cells (e.g., non-cancerous cells) and, thereby, reduce side effects.

The data obtained from the cell culture assays and animal studies can be used in formulating a range of dosage for use in humans. The dosage of such compounds lies generally within a range of circulating concentrations that include the $ED_{50}$ with little or no toxicity. The dosage may vary within this range depending upon the dosage form employed and the route of administration utilized. For a compound used as described herein (e.g., for treating cancer or an inflammatory condition in a subject), the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. Compounds that inhibit the growth of a cell, (i.e., a mammalian cell, a human cancer cell) can be any of the compounds described herein.

As defined herein, a therapeutically effective amount of a compound (i.e., an effective dosage) includes milligram or microgram amounts of the compound per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a compound depend upon the potency of the compound with respect to the inhibition of the cell growth (i.e., inhibition of the growth of a cancer cell). When one or more of these compounds is to be administered to an animal (e.g., a human) to treat an infection or a cancer, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated. One in the art will also appreciate that certain additional factors may influence the dosage and timing required to effectively treat a subject, including but not limited to the severity of the disease or disorder, previous treatments, and other diseases present. Moreover, treatment of a subject with a therapeutically effective amount of a protein, polypeptide, or antibody can include a single treatment or can include a series of treatments.

A compound or pharmaceutical composition thereof described herein can be administered to a subject as a combination therapy with another treatment, e.g., a treatment for a cancer, viral infection, or inflammation. For example, the combination therapy can include administering to the subject (e.g., a human patient) one or more additional agents that provide a therapeutic benefit to the subject who has, or is at risk of developing, (or suspected of having) a cancer. Thus, the compound or pharmaceutical composition and the one or more additional agents are administered at the same time. Alternatively, the compound can be administered first in time and the one or more additional agents administered second in time. The one or more additional agents can be administered first in time and the compound administered second in time. The compound can replace or augment a previously or currently administered therapy. For example, upon treating with a compound of the invention, administration of the one or more additional agents can cease or diminish, e.g.; be administered at lower levels. Administration of the previous therapy can also be maintained. In some instances, a previous therapy can be maintained until the level of the compound (e.g., the dosage or schedule) reaches a level sufficient to provide a therapeutic effect. The two therapies can be administered in combination.

It will be appreciated that in instances where a previous therapy is particularly toxic (e.g., a treatment for cancer or inflammation with significant side-effect profiles), administration of the compound can be used to offset and/or lessen the amount of the previously therapy to a level sufficient to give the same or improved therapeutic benefit, but without the toxicity.

In some instances, when the subject is administered a compound or pharmaceutical composition of the invention the first therapy is halted. The subject can be monitored for a first pre-selected result, e.g., an improvement in one or more symptoms of a cancer or an inflammatory condition such as any of those described herein (e.g., see above). In some cases, where the first pre-selected result is observed, treatment with the compound is decreased or halted. The subject can then be monitored for a second pre-selected result after treatment with the compound is halted, e.g., a worsening of a symptom of a cancer. When the second pre-selected result is observed, administration of the compound to the subject can be reinstated or increased, or administration of the first therapy is reinstated, or the subject is administered both a compound and first therapy, or an increased amount of the compound and the first therapeutic regimen.

The compound can also be administered with a treatment for one or more symptoms of a disease (e.g., a cancer, viral infection, or inflammatory condition). For example, the compound can be co-administered (e.g., at the same time or by any combination regimen described above) with, e.g., a pain medication or a treatment for anemia (e.g., Erythropoietin (EPO)).

The pharmaceutical compositions can be included in a container, pack, or dispenser together with instructions for administration.

E. Methods of Inhibiting an Interaction Between MUC1 and an HSF

Provided herein are in vitro, in vivo, and ex vivo methods of inhibiting an interaction between MUC1 and an HSF. While the invention is not limited by any particular theory or mechanism of action, it seems that binding of MUC1 to an HSF stimulates the HSF-mediated upregulation of MUC1 (e.g., in response to heat shock) and promote the development or viability of a dividing cell (e.g., a human cancer cell or a proliferating immune cell such as proliferating B- or T-cell). Thus, inhibition of this interaction can have general applicability in inhibiting the growth or viability of a cancer or immune cell. Inhibition of cell growth can be a reversible inhibition of cell growth, or more preferably can be an irreversible inhibition of cell growth (i.e., causing the death of the cell). Where the methods are in vivo or ex vivo, such methods can also be useful in the treatment of cancers or inflammatory conditions, which conditions include any of the autoimmune diseases disclosed herein.

Inhibition of the interaction between MUC1 and an HSF can include inhibition of an interaction between MUC1 and any HSF protein (e.g., HSF1, HSF2, HSF3, or HSF4) described herein. Similarly, MUC1, as referred to in the method, can include full-length, wild-type, mature MUC1 polypeptide (SEQ ID NO:1), the MUC1-cytoplasmic domain (MUC1-CD) (SEQ ID NO:2), or a functional or HSF-binding fragment of a MUC1 polypeptide. The cells can include both prokaryotic (e.g., bacterial cells) and eukaryotic cells. Eukaryotic cells can include, for example, yeast, insect, plant, fish, reptile, and mammalian cells (e.g., mouse, rat, rabbit, guinea pig, dog, cat, pig, horse, goat, cow, whale, monkey, or human). The cells can be normal, transformed, or malignant and of any histological type, e.g., without limitation, epithelial cells, fibroblasts, lymphoid cells, macrophages/monocytes, granulocytes, keratinocytes, or muscle cells. Cancer cells useful in the method can include cancer cells from cancers such as, but not limited to, lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, and bladder cancer. Suitable cell lines include those recited in the examples, e.g., breast cancer or colon cancer cell lines.

Where the methods are in vitro cell-based methods or in vivo, the methods of inhibiting an interaction between MUC1 and an HSF can optionally include a step of identifying a cell as one expressing MUC1. Such identification can include, for example, identifying (or detecting) whether a cell expresses MUC1 mRNA or MUC1 protein. Suitable methods of identifying (or detecting) the expression of MUC1 protein or MUC1 mRNA are well known to those of skill in the art, and are described herein. These methods can include, for example, SDS-polyacrylamide gel electrophoresis/western blotting techniques using antibodies specific for MUC1 (for detection of protein), or RT-PCR or northern blotting techniques for detection of mRNA expression. The cell can be any cell that expresses MUC1, e.g., a cell that expresses an endogenous or a recombinant or exogenous MUC1 mRNA or polypeptide.

The cell can also, optionally, be identified as one expressing the appropriate HSF (e.g., HSF1, HSF2, HSF3, or HSF4). Suitable detection methods for mRNA and protein include those described above. The cell can be any cell expressing the appropriate HSF, including cells that express endogenous, recombinant, or otherwise exogenous HSF mRNA or protein.

Compounds useful in the methods of inhibiting an interaction between MUC1 and an HSF can include any of the compounds described herein, or any other compounds with the appropriate inhibitory activity. Suitable compounds can include compounds, antibodies, an antibody fragments, polypeptides, or a peptidomimetics. Compounds can also include nucleic acids, for example, nucleic acids that inhibit the mRNA or protein expression of MUC1 or an HSF (e.g., siRNA or anti-sense nucleic acids; see "Methods of Inhibiting MUC1 Expression: Inhibiting Human Epidermal Growth Factor Receptor (HER)"). Other exemplary compounds for use in the methods include MUC1 or HSF polypeptides or their functional fragments. Examples of potential functional fragments of MUC1 include, for example, the MUC1-CD (SEQ ID NO:2), or fragments of the MUC1-CD containing amino acids 1-45, amino acids 2-71, amino acids 5-70, amino acids 10-70, amino acids 10-65, amino acids 15-70, amino acids 20-70, amino acids 25-70, amino acids 30-70, amino acids 35-70, amino acids 40-70, amino acids 45-70, amino acids 46-72, amino acids 50-70, or amino acids 55-70.

As indicated above, the binding of MUC1 to HSF1 appears to promote the HSF1-mediated upregulation of MUC1 expression in response to, for example, heat shock of a cell. Since MUC1 also binds to heat shock proteins, and heat shock proteins are known to inhibit the activity of HSF proteins, MUC1 could also work by preventing HSP-HSF inhibition. HSF-mediated upregulation of MUC1 could thus contribute to cancer cell viability or proliferation (e.g., in a noxious challenge such as heat shock). Thus, co-culturing a cell in the presence of, or further administering to a subject (e.g., a human patient), an inhibitor of an interaction between MUC1 and an HSF (e.g., HSF1) and one or more additional therapeutic agents can increase the efficacy of the one or more therapeutic agents (e.g., one or more therapeutic agents for the treatment of cancer). In some embodiments of the methods of inhibiting the interaction between MUC1 and an HSF (e.g., HSF1), the cells or subjects can be further treated with one or more additional therapeutic agents. Such therapeutic agents can include, but are not limited to, one or more chemotherapeutic agents, one or more forms of ionizing radiation, or hyperthermotherapy, such as any of those described herein.

1. In Vitro Methods of Inhibiting an Interaction Between MUC1 and an HSF

Provided herein is an in vitro method of inhibiting an interaction between a MUC1 reagent and an HSF (e.g., HSF1, HSF2, HSF3, or HSF4) reagent. The method can be useful, for example, in scientific studies to investigate the role of MUC1 in HSF-mediated transcriptional control, or any other scientific studies in which inhibiting the interaction between MUC1 and an HSF (e.g., HSF1) can be beneficial. Where the method is a cell-based method, it can also be useful as a further screening step, in e.g., a drug screening cascade, following the biochemical (e.g., a cell-free method of identifying a compound that inhibits the binding of an HSF to MUC1 described above) identification of a compound that inhibits the binding of an HSF to MUC1. Moreover, it can also serve as a "positive control" in assays to identify compounds with the same activity.

The method can include the steps of: contacting (i) a MUC1 reagent; (ii) an HSF1 reagent; or (iii) a molecular complex comprising (i) and (ii) with a compound that inhibits the interaction between MUC1 and HSF1. The method can be cell-based, and utilize any of the cells described herein (e.g., see above). The method can also, optionally, include the step of identifying a cell as one expressing MUC1. Methods for identifying or detecting a cell as expressing MUC1 mRNA or protein are well known to those in the art and are described above. Suitable concentrations of the inhibitory compound can be elucidated through routine experimentation and such optimization is well known to one of skill in the art. As described above, the cell may be co-cultured with one or more additional therapeutic agents.

It should be understood that where the cell is identified as one expressing a MUC1, the expressed MUC1 is the MUC1 reagent of the method. For example, a cell identified as one expressing a full-length, wild-type, mature MUC1 protein would thus have a MUC1 reagent that is full-length, wild-type, mature MUC1 protein.

Methods of determining or detecting the inhibition of an interaction between a MUC1 reagent and an HSF (e.g., HSF1, HSF2, HSF3, or HSF4) reagent are known in the art, and include, for example, in vitro and in situ methods (as described above). One method of determining inhibition of the interaction between MUC1 and HSF is an immunoprecipitation method and is set forth in the Examples below. Briefly, cells cultured in the presence of an inhibitory compound can be washed and harvested from the culture vessel. The cells can then be lysed using non-denaturing buffers that preserve protein-protein interactions, for example, buffers containing Nonidet-40 (NP-40) or Triton X-100 detergents. The lysates can then be clarified using, for example, centrifugation to remove insoluble debris. Clarified lysates can then be subjected to immunoprecipitation by adding to the lysate an antibody specific for either an HSF (e.g., HSF-1) or MUC1 for a time sufficient to allow for the binding of the antibody to its cognate antigen. Antibody-protein complexes are isolated from the lysate solution by coupling the complexes to solid support matrices. Examples of such solid support matrices include insoluble beads conjugated to anti-IgG antibodies or other antibody-binding reagents, for example, bacterial Protein-A or Protein-G. Isolated immunocomplexes can then be solubilized in Laemmli buffer (optionally containing reducing agent) and subjected to SDS-polyacrylamide gel electrophoresis (SDS-PAGE). Immunoblotting of the samples using antibodies specific for one or both of MUC1 and an HSF can then be used to determine whether a compound has inhibited the interaction between MUC1 and an HSF. For example, a reduced amount of HSF protein in anti-MUC1 antibody immunoprecipitates from cells treated with a compound as compared to the amount of HSF in MUC1 immunoprecipitates from cells not treated with the compound indicates that the compound has inhibited the interaction of the two proteins. Similarly, a reduced amount of MUC1 protein in anti-HSF antibody immunoprecipitates from cells treated with a compound as compared to the amount of MUC1 in HSF immunoprecipitates from cells not treated with the compound indicates that the compound has inhibited the interaction of the two proteins.

Another method of determining inhibition of an interaction between MUC1 and an HSF is an in situ staining method. Immunostaining methods are well known to those of skill in the art and include embodiments where the cells are still viable (e.g., confocal microscopy of live cells) or are fixed cells (e.g., immunohistochemistry). Examples of such methods are set forth in the Examples below. Antibodies specific for MUC1 and HSF polypeptides are applied (e.g., administered, delivered, contacted) to cells. The antibodies are independently labeled with a different detectable label (e.g., a different colored fluorophore (e.g., rhodamine, texas red, FITC, Green fluorescent protein, Cy3, Cy5) such that they can be readily and easily distinguished from one another. Use of an appropriate microscope (e.g., a confocal microscope) with the appropriate optical filters can identify the position of the labeled antibodies in a given cell. When each of the positions of the two proteins are determined (i.e., the location of their respective detectable label within the cell as determined by antibody binding), if they are found to occupy the same space, the two proteins are said to co-localize. Thus, when two proteins co-localize in the absence of a compound but do not co-localize in the presence of a compound, this can indicate that the compound has inhibited the interaction between the two proteins. Optionally the cells can be fixed, for example, using paraformaldehyde or formaldehyde, and permeabilized using a detergent (e.g., Triton-X100).

It is understood that co-localization of two proteins (e.g., MUC1 and an HSF such as HSF1) can be due to a direct, physical interaction of two proteins or it can be due to the localization of two proteins to a given, defined site in a cell (e.g., the nucleus, the cell membrane, the endoplasmic reticulum, the mitochondria), not necessarily involving a physical association between the two proteins. For example, MUC1 and HSF can co-localize in the cytoplasm of a cell, but in the absence of an interaction (e.g., in the presence of an inhibitor of their interaction) between them they can relocalize to distinct regions (e.g., the nucleus). In this regard, to define the particular localizations or organelles where localization occurs, it can be useful to use antibodies or other dyes that specifically detect the particular organelles or cellular regions of interest.

Since it appears that the binding of MUC1 to HSF may modulate the activity of the HSF transcription factor to promote gene expression (e.g., of MUC1), inhibiting the interaction between MUC1 and an HSF can also be determined by detecting the expression of a surrogate gene, i.e., a gene that is regulated by an HSF such as HSP70, HSP90, or MUC1. Thus, where MUC1 binding to an HSF stimulates the activity of the HSF (e.g., HSF1), inhibiting the MUC1-HSF interaction could result in a decrease in the expression of HSF-regulated genes. Methods of assessing HSF transactivation activity are also well known to those of skill in the art. Cell-based methods can involve monitoring the expression of HSF (e.g., HSF1) target genes (for example, heat shock proteins or MUC1). Assessing the inhibition of target gene expression, at the level of mRNA or protein, can be done using a variety of in situ or in vitro techniques, including, but not limited to, methods described above (e.g., immunofluorescence and western blot (for measuring protein) or RT-PCR and northern blotting techniques (for RNA)). Alternatively, detecting an inhibition of HSF activity can be done using an HSF-responsive promoter driven reporter system. By this method, nucleic acid vectors are designed which contain a coding sequence for a reporter gene (e.g., luciferase, chloramphenicol acetyltransferase (CAT), or green fluorescent protein(GFP)) operably linked to an HSF responsive enhancer element (heat shock responsive elements, HSE) (see, for example, Chen et al. (1997) J. Biol. Chem. 272(43):26803-26806). The vector can be introduced into a cell by any suitable transfection method. Ideally, a reduction in the expression of a reporter gene in the presence of a compound as compared to in the absence of the compound indicates that the compound inhibits HSF activity (e.g., inhibits the interaction between HSF and the MUC1 promoter). In related aspects, a stimulus, such as heat shock, could be co-administered to the cells, i.e., to increase the basal expression of the reporter gene from the reporter vector. In either case, inhibition of HSF-driven reporter expression (i.e., inhibition of an HSF) in the presence of a compound as compared to in the absence of a compound, corresponding to a reduction in the expression of a reporter gene from the reporter vector, indicates that the compound inhibits HSF activity. Methods of detecting an inhibition of HSF—driven reporter gene expression can also include RT-PCR or western blotting as described above. Preferably, the reporter gene encodes a polypeptide which is capable of giving a easily detectable signal, for example, fluorescence from a GFP reagent, or a detectable enzymatic activity, e.g., chloramphenicol acetyltransferase, alkaline phosphatase, luciferin/luciferase, or horseradish peroxidase.

Detection can also include lysis of the cells expressing the reporter gene for in vitro tests (e.g., in a test tube) for expression of the reporter gene.

Since it appears that HSF protects cells from programmed cell death in response to heat shock, another method of determining the inhibition of an interaction between MUC1 and HSF is detecting increased apoptosis of a cell in the presence following heat shock. For example, cells are plated on solid support matrix (e.g., a plastic tissue culture plate, or a multi-well (96 or 386-well) tissue culture plate) and grown in appropriate medium. Cells are then co-cultured in the absence or presence of an appropriate inhibitory compound and the exposed to elevated temperatures (e.g., heat shock) for a predetermined amount of time. Often, a control compound (e.g., a known inhibitor of known concentration) is also added to a sample of cells as an internal standard. In addition, a sample of cells is grown in the presence of a carrier, buffer, or solvent, in which the compound is delivered. Methods of detecting (e.g., determining or measuring) increased heat-shock-induced apoptosis in the presence of an inhibitor of MUC1-HSF interaction are myriad and well known to those of ordinary skill in the art. These methods can include, for example, counting the number of viable cells remaining in the well after the period of treatment with the compound. In this method, cells can be trypsinized from the plate, washed, stained with a dye (e.g., typan blue), and counted using a microscope or mechanical cell counter (Beckman-Coulter Z1™ Series COULTER COUNTER® Cell and Particle Counter). Since dyes like trypan blue are only taken up by dead or dying cells, this method allows for discrimination (i.e., blue or white cell) between viable and non-viable cells in a population. Another method for determining increased heat-shock-induced apoptosis in the presence of an inhibitory compound (e.g., any one of the compositions described herein) is monitoring cell death. Such methods are well known to those of skill in the art, and include propidium iodide staining of genomic DNA, or commercially available kits, such as, In situ Cell Death Detection ELISA Kit (Roche, Indianapolis, Ind.); and APO-Direct, APO-BRDU, or Annexin-FITC Apoptosis Kit (BD-Pharmingen, San Diego, Calif.). Such methods and kits for determining programmed cell death can optionally be used in conjunction with fluorescence flow cytometry (FFC) analysis. Examples of the methods and machines (instruments) useful for such methods are further described in "Methods of Inhibiting MUC1 Expression by Inhibiting a Human Epidermal Growth Factor Receptor (HER)."

Any of the in vitro methods for detecting inhibition of the interaction between MUC1 and an HSF (in vivo or in vitro, or any screening methods described herein) can be performed in any format that allows for rapid preparation, processing, and analysis of multiple reactions. This can be, for example, in multi-well assay plates (e.g., 96 wells or 386 wells). Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting the signal generated from the assay. Examples of such detectors include, but are not limited to, spectrophotometers, luminometers, fluorimeters, and devices that measure radioisotope decay.

2. In Vivo Methods of Inhibiting an Interaction Between MUC1 and an HSF

The invention features a method of inhibiting an interaction between MUC1 and an HSF, which includes the steps of: optionally identifying a subject as having, or at risk of developing, (or suspected to have) a cancer comprising one or more cancer cells expressing MUC1; and delivering to the subject a compound that inhibits the interaction between MUC1 and an HSF. The method can also, optionally, include the step of determining whether inhibition of an interaction between MUC1 and an HSF has occurred and/or determining if the one or more cancer cells of the subject express MUC1.

In one in vivo approach, a compound that inhibits binding of MUC1 to an HSF is administered to a subject. The subject can be any mammal, e.g., a human (e.g., a human patient) or a primate (e.g., chimpanzee, baboon, or monkey), mouse, rat, rabbit, guinea pig, gerbil, hamster, horse, a type of livestock (e.g., cow, pig, sheep, or goat), a dog, cat, or a whale. Generally, the compounds of the invention will be suspended in a pharmaceutically-acceptable carrier (e.g., physiological saline) and administered orally or parenterally, e.g., injected intravenously, subcutaneously, intramuscularly, intrathecally, intraperitoneally, intrarectally, intravaginally, intranasally, intragastrically, intratracheally, or intrapulmonarily. They can also be delivered directly to tumor cells, e.g., to a tumor or a tumor bed following surgical excision of the tumor, in order to kill any remaining tumor cells. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001 mg/kg-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more fold). Encapsulation of the polypeptide in a suitable delivery vehicle (e.g., polymeric microparticles or implantable devices) may increase the efficiency of delivery, particularly for oral delivery.

Alternatively, where an inhibitory compound is a polypeptide, a polynucleotide containing a nucleic acid sequence encoding the polypeptide can be delivered to appropriate cells in a mammal. Expression of the coding sequence can be directed to any cell in the body of the subject. However, expression will preferably be directed to cells in the vicinity of the tumor cells whose proliferation it is desired to inhibit. Expression of the coding sequence can be directed to the tumor cells themselves. This can be achieved by, for example, the use of polymeric, biodegradable microparticle or microcapsule delivery devices known in the art. Another way to achieve uptake of the nucleic acid is using liposomes, prepared by standard methods. The vectors can be incorporated alone into these delivery vehicles or co-incorporated with tissue-specific or tumor-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano et al. (1995), J. Mol. Med. 73:479, the disclosure of which is incorporated herein by reference in its entirety). Alternatively, tissue specific targeting can be achieved by the use of tissue-specific transcriptional regulatory elements (TRE) which are known in the art. Delivery of "naked DNA" (i.e., without a delivery vehicle) to an intramuscular, intradermal, or subcutaneous site is another means to achieve in vivo expression.

In the relevant polynucleotides (e.g., expression vectors), the nucleic acid sequence encoding the polypeptide of interest with an initiator methionine and optionally a targeting sequence is operatively linked to a promoter or enhancer-promoter combination. Short amino acid sequences can act as signals to direct proteins to specific intracellular compartments. Such signal sequences are described in detail in U.S. Pat. No. 5,827,516, the disclosure of which is incorporated herein by reference in its entirety.

Enhancers provide expression specificity in terms of time, location, and level. Unlike a promoter, an enhancer can function when located at variable distances from the transcription initiation site, provided a promoter is present. An enhancer can also be located downstream of the transcription initiation site. To bring a coding sequence under the control of a promoter, it is necessary to position the translation initiation site of the translational reading frame of the peptide or polypeptide between one and about fifty nucleotides downstream (3') of the promoter. Promoters of interest include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3 phosphoglycerate kinase, the promoters of acid phosphatase, and the promoters of the yeast α mating factors, the adenoviral E1b minimal promoter, or the thymidine kinase minimal promoter. The DF3 enhancer can be particularly useful for expression of an inhibitory compound in cells that naturally express MUC1, for example, normal epithelial cells or malignant epithelial cells (carcinoma cells), e.g., breast cancer cells (see U.S. Pat. Nos. 5,565,334 and 5,874,415, the disclosures of which are incorporated herein by reference in their entirety). The coding sequence of the expression vector is operatively linked to a transcription terminating region.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles that are suitable for administration to a human, e.g., physiological saline or liposomes. A therapeutically effective amount is an amount of the polynucleotide that is capable of producing a medically desirable result (e.g., decreased proliferation of cancer cells) in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to approximately $10^{12}$ copies of the polynucleotide molecule. This dose can be repeatedly administered, as needed. Schedules and co-administration can be any of those described herein (see, for example, "Pharmaceutical compositions and Methods of Treatment"). Routes of administration can be any of those listed above.

3. Ex Vivo Methods of Inhibiting an Interaction Between MUC1 and an HSF

An ex vivo strategy can involve transfecting or transducing cells obtained from the subject to be treated (or another subject) with a polynucleotide encoding a polypeptide that inhibits an interaction between MUC1 and an HSF. The transfected or transduced cells are then administered to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells. Such cells act as a source of the inhibitory polypeptide for as long as they survive in the subject. Alternatively, tumor cells or immune cells, preferably obtained from the subject (autologous) but potentially from a subject of the same species other than the subject (allogeneic), can be transfected or transformed by a vector encoding the inhibitory polypeptide. The tumor cells, preferably treated with an agent (e.g., ionizing irradiation) that ablates their proliferative capacity, are then introduced into the subject, where they secrete the polypeptide.

The ex vivo methods include the steps of harvesting cells from a subject, culturing the cells, transducing them with an expression vector, and maintaining the cells under conditions suitable for expression of the polypeptide that inhibits binding of MUC1 to an HSF. These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced can be selected, for example, for expression of the coding sequence or of a drug resistance gene. The cells may then be lethally irradiated (if desired) and injected or implanted into the same or another subject.

F. Methods of Inhibiting an Interaction Between MUC1 and STAT3

Provided herein are in vitro, in vivo, and ex vivo methods of inhibiting an interaction between MUC1 and STAT3. While the invention is not limited by any particular theory or mechanism of action, it seems that binding of MUC1 to STAT3 could stimulate STAT3 activity and/or STAT3-mediated upregulation of MUC1 (e.g., in response to IL-6) and promote the development or viability of a dividing cell (e.g., a human cancer cell or a proliferating immune cell such as proliferating B- or T-cell). Thus, inhibition of this interaction can have general applicability in inhibiting the growth or viability of a cancer or immune cell. Inhibition of cell growth can be a reversible inhibition of cell growth, or more preferably can be an irreversible inhibition of cell growth (i.e., causing the death of the cell). Where the methods are in vivo or ex vivo, such methods can also be useful in the treatment of cancers or inflammatory conditions, which conditions include any of the autoimmune diseases disclosed herein.

Inhibition of the interaction between MUC1 and STAT3 can include inhibition of an interaction between MUC1 and a STAT3 protein from any species expressing a homolog of human HSF1 described herein. Similarly, MUC1, as referred to in the method, can include full-length, wild-type, mature MUC1 polypeptide (SEQ ID NO:1), the MUC1-cytoplasmic domain (MUC1-CD) (SEQ ID NO:2), or a functional or STAT3-binding fragment of a MUC1 polypeptide. The cells can include any of those described above under "Methods of Inhibiting an Interaction Between MUC1 and an HSF."

Where the methods are in vitro cell-based methods or in vivo, the methods of inhibiting an interaction between MUC1 and STAT3 can optionally include a step of identifying a cell as one expressing MUC1 or STAT3. Such identification can include, for example, identifying (or detecting) whether a cell expresses MUC1 or STAT3 mRNA or protein. Suitable methods of detecting protein and/or mRNA are well known to those of skill in the art, and are described herein. These methods can include, for example, SDS-polyacrylamide gel electrophoresis/western blotting techniques using antibodies specific for MUC1 (for detection of protein), or RT-PCR or northern blotting techniques for detection of mRNA expression. The cell can be any cell that expresses MUC1 or STAT3, e.g., a cell that expresses an endogenous or a recombinant or exogenous MUC1 mRNA or polypeptide.

Compounds useful in the methods of inhibiting an interaction between MUC1 and an STAT3 include any of the compounds described herein (e.g., see "Methods of Inhibiting an Interaction Between MUC1 and an HSF.

1. In Vitro Methods of Inhibiting an Interaction Between MUC1 and STAT3

Provided herein is an in vitro method of inhibiting an interaction between a MUC1 reagent and a STAT3 reagent. The method can be useful, for example, in scientific studies to investigate the role of MUC1 in STAT3-mediated transcriptional control, or any other scientific studies in which inhibiting the interaction between MUC1 and STAT3 can be beneficial. Where the method is a cell-based method, it can also be useful as a further screening step, in e.g., a drug screening cascade, following the biochemical (e.g., a cell-free method of identifying a compound that inhibits the binding of STAT3 to MUC1 described above) identification of a compound that inhibits the binding of STAT3 to MUC1. Moreover, it can also serve as a "positive control" in assays to identify compounds with the same activity.

The method can include the steps of: contacting (i) a MUC1 reagent; (ii) a STAT3 reagent; or (iii) a molecular complex comprising (i) and (ii) with a compound that inhibits the interaction between MUC1 and STAT3. The method can be cell-based, and utilize any of the cells described herein (e.g., see above). The method can also, optionally, include the step of identifying a cell as one expressing MUC1. Methods for identifying or detecting a cell as expressing MUC1 mRNA or protein are well known to those in the art and are described above. Suitable concentrations of the inhibitory compound can be elucidated through routine experimentation and such optimization is well known to one of skill in the art. As described above, the cell may be co-cultured with one or more additional therapeutic agents.

It should be understood that where the cell is identified as one expressing a MUC1, the expressed MUC1 can be the MUC1 reagent of the method. For example, a cell identified as one expressing a full-length, wild-type, mature MUC1 protein would thus have a MUC1 reagent that is full-length, wild-type, mature MUC1 protein.

Methods of determining or detecting the inhibition of an interaction between a MUC1 reagent and a STAT3 reagent are known in the art, and include, for example, in vitro (e.g., immunoprecipitation) and in situ (immunohistochemistry) methods (as described above under "In vitro Methods of Inhibiting an Interaction Between MUC1 and an HSF).

Since it appears that the binding of MUC1 to STAT3 can modulate the activity of the STAT3 transcription factor to promote gene expression (e.g., of MUC1), inhibiting the interaction between MUC1 and STAT3 can also be determined by detecting the expression of a surrogate gene, i.e., a gene that is regulated by STAT3 such as MUC1. Methods of assessing the inhibition of STAT3 target gene expression, at the level of mRNA or protein, are described above (e.g., immunofluorescence and western blot (for measuring protein) or RT-PCR and northern blotting techniques (for RNA)). Alternatively, detecting an inhibition of STAT3 activity can be done using an STAT3-responsive promoter driven reporter system (see above under "In vitro Methods of Inhibiting an Interaction between MUC1 and an HSF").

2. In Vivo Methods of Inhibiting an Interaction Between MUC1 and STAT3

The invention features an in vivo method of inhibiting an interaction between MUC1 and STAT3, which includes the steps of: optionally identifying a subject as having, or at risk of developing, (or suspected of having) a cancer comprising one or more cancer cells expressing MUC1; and delivering to the subject a compound that inhibits the interaction between MUC1 and an HSF. The method can also, optionally, include the step of determining whether inhibition of an interaction between MUC1 and STAT3 has occurred and/or determining if the one or more cancer cells of the subject's cancer express MUC1.

The invention features an in vivo method of inhibiting an interaction between MUC1 and STAT3, which includes the steps of: optionally identifying a subject as having, or at risk of developing, (or suspected of having) an inflammatory disorder mediated by one or more inflammatory cells expressing MUC1; and delivering to the subject a compound that inhibits the interaction between MUC1 and an HSF. The method can also, optionally, include the step of determining whether inhibition of an interaction between MUC1 and STAT3 has occurred and/or determining if the one or more inflammatory cells of the subject express MUC1.

Suitable in vivo methods are described under "In vivo Methods of Inhibiting an Interaction Between MUC1 and an HSF."

3. Ex Vivo Methods of Inhibiting an Interaction Between MUC1 and STAT3

An ex vivo strategy can involve transfecting or transducing cells obtained from the subject to be treated (or another subject) with a polynucleotide encoding a polypeptide that inhibits an interaction between MUC1 and STAT3. The transfected or transduced cells are then administered to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells. Such cells act as a source of the inhibitory polypeptide for as long as they survive in the subject. Alternatively, tumor cells or immune cells, preferably obtained from the subject (autologous) but potentially from a subject of the same species other than the subject (allogeneic), can be transfected or transformed by a vector encoding the inhibitory polypeptide. The tumor cells, preferably treated with an agent (e.g., ionizing irradiation) that ablates their proliferative capacity, are then introduced into the subject, where they secrete the polypeptide.

The ex vivo methods include the steps of harvesting cells from a subject, culturing the cells, transducing them with an expression vector, and maintaining the cells under conditions suitable for expression of the polypeptide that inhibits binding of MUC1 to STAT3. These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced can be selected, for example, for expression of the coding sequence or of a drug resistance gene. The cells may then be lethally irradiated (if desired) and injected or implanted into the same or another subject.

G. Methods of Inhibiting an Interaction Between an HSF and a MUC1 Promoter

Provided herein are in vitro, in vivo, and ex vivo methods of inhibiting an interaction between an HSF (e.g., HSF1, HSF2, HSF3, or HSF4) and a MUC1 promoter (e.g., the HSE of a MUC1 promoter). While not limited by any particular theory or mechanism of action, the binding of an HSF to a MUC1 promoter stimulates MUC1 expression and can thereby promote the development or viability of, e.g., a cancer cell (e.g., in a human tumor). Thus, inhibition of this interaction can have general applicability in inhibiting the growth or viability of a cancer cell. Inhibition of cell growth can be a reversible inhibition of cell growth, or irreversible inhibition of cell growth (i.e., causing the death of the cell). As above, where the methods are in vivo or ex vivo, such methods can also be useful in the treatment of cancers or inflammatory conditions. Moreover, it can also serve as a "positive control" in assays to identify compounds with the same activity.

Inhibition of the interaction between an HSF and the MUC1 promoter can include inhibition of an interaction between any HSF protein (e.g., HSF1, HSF2, HSF3, or HSF4 or functional fragment thereof such as the DNA binding domain of an HSF) and/or MUC1 promoter described herein. The MUC1 promoter, as referred to in the method, can include a human MUC1 promoter (e.g., the human MUC1 promoter with SEQ ID NO:3) or a functional or HSE-containing fragment of a MUC1 promoter such as the HSE of the human MUC1 promoter depicted in SEQ ID NO:4. Cells useful in the methods described herein are described above.

The methods of inhibiting an interaction between an HSF (e.g., HSF1) and a MUC1 promoter (e.g., an HSE of the human MUC1 promoter) can optionally include a step of identifying a cell as one expressing HSF1. Such identification can include, for example, identifying (or detecting) whether a cell expresses HSF mRNA or HSF protein. Suitable methods of identifying (or detecting) the expression of HSF protein or HSF mRNA are well known to those of skill in the art, and include those described herein. The cell can be any cell that expresses HSF, including any cells that express an endogenous or a recombinant or exogenous HSF mRNA or polypeptide.

In some cases, the cell actually expresses MUC1 mRNA or protein. Thus, the method can, optionally, include the step of identifying a cell as one expressing MUC1 by any of the above-mentioned methodologies. However, it should be understood that any cell having a MUC1 promoter can be useful for the method and need not per se express MUC1 mRNA or protein.

Compounds useful in the methods of inhibiting an interaction between an HSF and a MUC1 promoter can include any of the compounds described herein, or any other compounds with the appropriate inhibitory activity. Suitable compounds include any of those described above, e.g., aptamers. Other exemplary compounds for use in the methods include HSF polypeptides or their functional fragments. Furthermore, exemplary compounds also include fragments of a MUC1 promoter, e.g., fragments that contain an HSE that is recognized and bound by an HSF. Examples of potential functional fragments of a MUC1 promoter include, for example, fragments comprising the HSE of human MUC1 (SEQ ID NO:4). Exemplary compounds also include aptamers (see above) such as those described in Zhao et al. (2006) 34(13): 3755-3761.

While the invention is not limited by any particular mechanism of action, the binding of HSF1 to the MUC1 promoter was shown to promote the expression of MUC1 in response to stress, for example, heat shock of a cell. Thus, co-culturing a cell in the presence of, or further administering to a subject (e.g., a human patient), an inhibitor of an interaction between an HSF (e.g., HSF1) and a MUC1 promoter and one or more additional therapeutic agents can increase the efficacy of the one or more therapeutic agents (e.g., one or more therapeutic agents for the treatment of cancer) as described above.

1. In Vitro Methods of Inhibiting an Interaction Between an HSF and a MUC1 Promoter Provided herein is an in vitro method of inhibiting an interaction between an HSF (e.g., HSF1, HSF2, HSF3, or HSF4) reagent and a MUC1 promoter reagent. The method can be useful, for example, in scientific studies investigating the role of HSF in the control of MUC1 expression, the molecular mechanisms of HSF-mediated transcriptional response to heat shock, or any other scientific studies in which inhibiting the interaction between an HSF (e.g., HSF1) and a MUC1 promoter can be beneficial. Where the method is a cell-based method, it can also be useful as a further screening step, in e.g., a drug screening cascade, following the biochemical (e.g., a cell-free method of identifying a compound that inhibits the binding of an HSF to a MUC1 promoter described above) identification of a compound that inhibits the binding of an HSF to a MUC1 promoter. Moreover, it can also serve as a "positive control" in assays to identify compounds with the same activity.

Suitable methods of determining or detecting the inhibition of an interaction between a transcription factor (e.g., an HSF (e.g., HSF1, HSF2, HSF3, or HSF4)) and a nucleic acid (e.g., a MUC1 promoter or a fragment of the promoter containing an HSE) are known in the art, and include, for example, in vitro and in situ methods. Examples of such methods are described in detail above (see "Methods of Screening for Inhibitory Compounds, Inhibition of HSF-MUC1 Promoter Interactions" above).

While the invention is not limited by any particular theory or mechanism of action, since it appears that the binding of HSF1 to a MUC1 promoter induces MUC1 expression, inhibiting the interaction between an HSF and the MUC1 promoter can also be determined by detecting the expression of MUC1 in the presence as compared to the absence of a compound. Methods of detecting or determining MUC1 mRNA and MUC1 protein levels are set forth above. Assessing the inhibition of HSF binding to a MUC1 promoter can also be done using a reporter vector system driven by a MUC1 promoter. For example, a nucleic acid vector can be designed and constructed that encodes a coding sequence for a reporter gene (e.g., luciferase, chloramphenicol acetyltransferase (CAT), or green fluorescent protein(GFP)) operably linked to a MUC1 promoter (e.g., the human MUC1 promoter sequence SEQ ID NO:3). The vector can be introduced into a cell by any suitable transfection method. Ideally, inhibition of the expression of a reporter gene in the presence of a test compound as compared to in the absence of the compound indicates that the compound inhibits HSF activity (e.g., inhibits the interaction between the HSF and the MUC1 promoter). In related aspects, a stimulus, such as heat shock, could be co-administered to the cells to stimulate the activity of an HSF (e.g., HSF1), e.g., where basal expression of the reporter gene is low. Inhibition of HSF-driven reporter gene expression (i.e., inhibition of the binding of an HSF to a MUC1 promoter) in the presence of a compound as compared to in the absence of a compound indicates that the compound inhibits HSF activity (i.e., the binding of the HSF to the MUC1 promoter). Methods of detecting expression of, and also an inhibition of, HSF-driven reporter gene expression can also include RT-PCR or western blotting as described above.

Since it appears that HSF protects cells from programmed cell death in response to heat shock, another method of determining the inhibition of an interaction between MUC1 and HSF is detecting increased apoptosis of a cell in the presence following heat shock as described herein.

2. In Vivo Methods of Inhibiting an Interaction Between an HSF and a MUC1 Promoter The invention features an in vivo method of inhibiting the interaction between an HSF (e.g., HSF1) and a MUC1 promoter, which includes the steps of: optionally identifying a subject as having, or at risk of developing, (or suspected of having) a cancer comprising one or more cancer cells expressing MUC1; and delivering to the subject a compound that inhibits the interaction between an HSF and a MUC1 promoter. The method can include, optionally, the steps of: determining if one or more cancer cells of the subject's cancer express MUC1 and/or determining whether inhibition of the HSF and a MUC1 promoter has occurred (suitable methods for which are described above).

The invention features an in vivo method of inhibiting the interaction between an HSF (e.g., HSF1) and a MUC1 promoter, which includes the steps of: optionally identifying a subject as having, or at risk of developing, (or suspected of having) an inflammatory condition mediate by one or more cells expressing MUC1; and delivering to the subject a compound that inhibits the interaction between an HSF and a MUC1 promoter. The method can include, optionally, the steps of: determining if one or more inflammatory cells express MUC1 and/or determining whether inhibition of the HSF and a MUC1 promoter has occurred (suitable methods for which are described above).

In one in vivo approach, a compound that inhibits binding of an HSF to a MUC1 promoter is administered to a subject (e.g., any of the subjects described herein). The compounds of the invention will, generally, be suspended in a pharmaceutically-acceptable carrier (e.g., physiological saline) and administered by any of the methods described herein. Required dosage and administration schedules depends on a variety of factors set forth in the preceding sections.

Where an inhibitory compound is a polypeptide, a polynucleotide containing a nucleic acid sequence encoding the polypeptide can be delivered to appropriate cells in a mammal as described in detail above.

3. Ex Vivo Methods of Inhibiting an Interaction Between an HSF and a MUC1 Promoter An ex vivo strategy can involve transfecting or transducing cells obtained from the subject (or from another subject) with a polynucleotide encoding a polypeptide that inhibits an interaction between an HSF (e.g., HSF1) and a MUC1 promoter. The transfected or transduced cells are then administered to the subject. The cells can be any of a wide range of types including, without limitation, any of the cells described above. Such cells act as a source of the inhibitory polypeptide for as long as they survive in the subject. Alternatively, tumor cells or immune cells, preferably obtained from the subject (autologous) but potentially from a subject of the same species other than the subject (allogeneic), can be transfected or transformed by a vector encoding the inhibitory polypeptide. The tumor cells, preferably treated with an agent (e.g., ionizing irradiation) that ablates their proliferative capacity, are then introduced into the subject, where they secrete the polypeptide.

The ex vivo methods include the steps of harvesting cells from a subject, culturing the cells, transducing them with an expression vector, and maintaining the cells under conditions suitable for expression of the polypeptide that inhibits binding of an HSF (e.g., HSF1) to a MUC1 promoter (e.g., an HSE of a MUC1 promoter). These methods are known in the art of molecular biology and suitable methods are described above.

H. Methods of Inhibiting an Interaction Between STAT3 and a MUC1 Promoter

Provided herein are in vitro, in vivo, and ex vivo methods of inhibiting an interaction between STAT3 and a MUC1 promoter (e.g., the STAT3-binding element of a MUC1 promoter). While the invention is not limited by any particular theory or mechanism of action, it appears that binding of STAT3 to a MUC1 promoter stimulates MUC1 expression and thereby promotes the development or viability of a cancer cell (e.g., in a human tumor). Thus, inhibition of this interaction can have general applicability in inhibiting the growth or viability of a cancer cell. STAT3 is also part of the IL-6/IL-6R pathway, which has herein been shown by the inventors to stimulate the expression of MUC1. Since MUC1 and STAT3 have been shown to play a role in inflammation, inhibition of STAT3-MUC1 promoter interactions can also be useful for inhibiting the growth of cells (e.g., immune cells involved in any of the inflammatory conditions described herein). Inhibition of cell growth can be a reversible inhibition of cell growth, or irreversible inhibition of cell growth (i.e., causing the death of the cell). As above, where the methods are in vivo or ex vivo, such methods can also be useful in the treatment of cancers or inflammatory conditions, such as any of those described herein.

Inhibition of the interaction between STAT3 and the MUC1 promoter can include inhibition of an interaction between any STAT3 protein (e.g., full length STAT3 or functional fragment thereof such as the STAT3 DNA-binding domain) and/or MUC1 promoter described herein. The MUC1 promoter, as referred to in the method, can include a human MUC1 promoter (e.g., the human MUC1 promoter with SEQ ID NO:3) or a functional or STAT3-binding element containing fragment of a MUC1 promoter such as the STAT3-binding element of the human MUC1 promoter depicted in SEQ ID NO:5. Cells useful in the methods described herein are described above.

The methods of inhibiting an interaction between STAT3 and a MUC1 promoter (e.g., a STAT3-binding element of a MUC1 promoter) can optionally include a step of identifying a cell as one expressing MUC1 or having a MUC1 promoter. Such identification can include, for example, identifying (or detecting) whether a cell expresses STAT3 mRNA or STAT3 protein. Suitable methods of identifying (or detecting) the expression of STAT3 protein or STAT3 mRNA are well known to those of skill in the art, and include those described herein. The cell can be any cell that expresses STAT3, including any cell described above and any cell that expresses an endogenous STAT3 or a cell that expresses a recombinant or exogenous STAT3 mRNA or polypeptide.

In some cases it can be useful to treat a cell that expresses MUC1. Thus, the method can, optionally, include the step of identifying a cell as one expressing MUC1 by any of the above-mentioned methodologies. However, as above, it should be understood that any cell having a MUC1 promoter can be useful for the method and need not per se express MUC1 mRNA or protein.

Compounds useful in the methods of inhibiting an interaction between STAT3 and a MUC1 promoter can include any of the compounds described herein, or any other compounds with the appropriate inhibitory activity. Suitable compounds include any of those described above, e.g., aptamers. Other exemplary compounds for use in the methods include STAT3 polypeptides or their functional fragments. Furthermore, exemplary compounds also include fragments of a MUC1 promoter, e.g., fragments that contain a STAT3-binding element that is recognized and bound by STAT3. Examples of potential functional fragments of a MUC1 promoter include, for example, fragments comprising the STAT3-binding element of human MUC1 (SEQ ID NO:5).

While the invention is not limited by any particular mechanism of action, it appears that binding of STAT3 to the MUC1 promoter drives the expression of MUC1 in response to, for example, IL-6 or HRG treatment of a cell. Thus, co-culturing a cell in the presence of, or further administering to a subject (e.g., a human patient), an inhibitor of an interaction between STAT3 and a MUC1 promoter and one or more additional therapeutic agents can increase the efficacy of the one or more therapeutic agents (e.g., one or more therapeutic agents for the treatment of cancer) as described above.

1. In Vitro Methods of Inhibiting an Interaction Between STAT3 and a MUC1 Promoter Provided herein is an in vitro method of inhibiting an interaction between a STAT3 reagent and a MUC1 promoter reagent. The method can be useful, for example, in scientific studies investigating the role of STAT3 in the control of MUC1 expression, STAT3-mediated transcriptional response to IL-6, or any other scientific studies in which inhibiting the interaction between STAT3 and a MUC1 promoter can be beneficial. Where the method is a cell-based method, it can also be useful as a further screening step, in, e.g., a drug screening cascade, following the biochemical (e.g., a cell-free method of identifying a compound that inhibits the binding of STAT3 to a MUC1 promoter described above) identification of a compound that inhibits the binding of STAT3 to a MUC1 promoter. Moreover, it can also serve as a "positive control" in assays to identify compounds with the same activity.

Suitable methods of determining or detecting the inhibition of an interaction between a transcription factor (e.g., STAT3) and a nucleic acid (e.g., a MUC1 promoter or a fragment of the promoter containing a STAT3-binding element) are known in the art, and include, for example, in vitro and in situ methods. Examples of such methods are described in detail above (see "Methods of Screening for Inhibitory Compounds, Inhibition of HSF-MUC1 Promoter Interactions").

While the invention is not limited by any particular theory or mechanism of action, since it appears that the binding of STAT3 to a MUC1 promoter induces MUC1 expression, inhibiting the interaction between STAT3 and the MUC1 promoter can also be determined by detecting the STAT3-dependent expression of MUC1 in the presence as compared to the absence of a compound. Methods of detecting or determining MUC1 mRNA and MUC1 protein levels are set forth above. Assessing the inhibition of STAT3 binding to a MUC1 promoter can also be done using a reporter vector system driven by a MUC1 promoter using obvious variations of the methods described above (see, e.g., Methods of Screening for Inhibitory Compounds, Inhibition of HSF-MUC1 Promoter Interactions"). Ideally, inhibition of the expression of a reporter gene in the presence of a compound as compared to in the absence of the compound indicates that the compound has inhibited STAT3 activity (as reflected by the binding of STAT3 to the MUC1 promoter). In related aspects, a stimulus, such as IL-6, could be co-administered to the cells to stimulate the activity of STAT3. Inhibition of STAT3-driven reporter gene expression (i.e., inhibition of the binding of STAT3 to a MUC1 promoter) in the presence of a compound as compared to in the absence of the compound indicates that the compound inhibits STAT3 activity (i.e., inhibits the binding of STAT3 to the MUC1 promoter). Methods of detecting expression of, and also an inhibition of, STAT3-driven reporter gene expression can also include RT-PCR or western blotting as described above.

2. In Vivo Methods of Inhibiting an Interaction Between STAT3 and a MUC1 Promoter The invention features an in vivo method of inhibiting the interaction between STAT3 and a MUC1 promoter. The method includes the steps of: optionally identifying a subject as having, or at risk of developing, a cancer comprising one or more cancer cells expressing MUC1; and delivering to the subject a compound that inhibits the interaction between STAT3 and a MUC1 promoter. The method can also, optionally, include the steps of: determining whether one or more cancer cells of the subject's cancer express MUC1 mRNA or protein and/or determining whether inhibition of the interaction between STAT3 and the MUC1 promoter has occurred.

The invention features an in vivo method of inhibiting the interaction between STAT3 and a MUC1 promoter. The method includes the steps of: optionally identifying a subject as having, or at risk of developing, an inflammatory condition mediated by one or more inflammatory cells expressing MUC1; and delivering to the subject a compound that inhibits the interaction between STAT3 and a MUC1 promoter. The method can also, optionally, include the steps of: determining whether one or more inflammatory cells express MUC1 mRNA or protein and/or determining whether inhibition of the interaction between STAT3 and the MUC1 promoter has occurred.

In one in vivo approach, a compound that inhibits binding of STAT3 to a MUC1 promoter is administered to a subject (e.g., any of the subjects described herein). The compounds of the invention will, generally, be suspended in a pharmaceutically-acceptable carrier (e.g., physiological saline) and administered by any of the methods described herein. Required dosage and administration schedules depend on a variety of factors set forth in the preceding sections.

Where an inhibitory compound is a polypeptide, a polynucleotide containing a nucleic acid sequence encoding the polypeptide can be delivered to appropriate cells in a mammal as described in detail above.

3. Ex Vivo Methods of Inhibiting an Interaction Between STAT3 and a MUC1 Promoter An ex vivo strategy can involve transfecting or transducing cells obtained from the subject or another subject with a polynucleotide encoding a polypeptide that inhibits an interaction between STAT3 and a MUC1 promoter. The transfected or transduced cells are then administered to the subject (e.g., a human patient). The cells can be any of a wide range of types including, without limitation, any of the cells described above. Such cells act as a source of the inhibitory polypeptide for as long as they survive in the subject. Alternatively, tumor cells or immune cells, preferably obtained from the subject (autologous) but potentially from a subject of the same species other than the subject (allogeneic), can be transfected or transformed by a vector encoding the inhibitory polypeptide. The tumor cells, preferably treated with an agent (e.g., ionizing irradiation) that ablates their proliferative capacity, are then introduced into the subject, where they secrete the polypeptide.

The ex vivo methods include the steps of harvesting cells from a subject, culturing the cells, transducing them with an expression vector, and maintaining the cells under conditions suitable for expression of the polypeptide that inhibits binding of STAT3 to a MUC1 promoter (e.g., a STAT3 binding element of a MUC1 promoter). These methods are known in the art of molecular biology and suitable methods are described above.

I. Methods of Inhibiting MUC1 Expression by Inhibiting Human Epidermal Growth Factor Receptors (HERs)

Provided herein are in vitro, in vivo, and ex vivo methods of inhibiting MUC1 expression by inhibiting a human epidermal growth factor receptor (e.g., HER2) or a homolog of such a receptor. While the invention is not limited by any particular theory or mechanism of action, heregulin, through ErbB2-dependent signaling, induces MUC1 expression and thereby promotes the development or viability of a cancer cell (e.g., in a human tumor). Thus, inhibition of a HER such as ErbB-2 (i.e., ErbB2/HER2/neu) can have general applicability in inhibiting the growth or viability of a cancer cell through its effect on MUC1 expression. As above, where the methods are in vivo or ex vivo, such methods can also be useful in the treatment of cancers (e.g., any of the cancer types described herein) or inflammatory diseases.

Inhibition of a HER is inhibition of the expression of HER (e.g., mRNA or protein expression of a HER), the kinase activity of the HER, or inhibition of one or more downstream effects of HER. Expression of a HER can include both expression of mRNA and protein. Inhibition of kinase activity can include inhibition of the autophosphorylation activity of a HER or the phosphorylation of one or more substrates of a HER. Cells useful in the methods include any of those described herein.

Where the methods include the step of identifying a cell (e.g., a cancer cell) as one expressing a HER (e.g. ErbB-2), such identification can include, for example, identifying (or detecting) whether a cell expresses HER mRNA or HER protein. Suitable methods of identifying (or detecting) the expression of a HER protein or mRNA are well known in the skill and are described herein. It is understood that the same types of detection methods (e.g., for mRNA or protein) apply where the methods include the step of identifying a cell (e.g., a cancer cell) as one expressing MUC1.

Compounds useful in the methods of inhibiting a HER include any of the compounds described herein, or any other compounds with the appropriate inhibitory activity. Suitable compounds can include small molecules, antibodies, an antibody fragments, polypeptides, or a peptidomimetics.

In some instances, inhibition of a HER is inhibition of the kinase activity of the HER. Several exemplary compounds for inhibiting the kinase activity of a HER (e.g., HER2) are well known to those in the art and include, for example, Gleevec (imatinib mesylate, also known as ST1571; Peggs et al (2004) Clin Exp Med. 4(1):1-9; Drucker et al (2004) Adv Cancer Res. 91:1-30), AMN107 (Weisberg et al. (2006) Br. J. Cancer 94(12):1765-9); and dasatinib (2006) N Engl. J. Med. 354 (24):2531-41), Iressa, Tarceva, Erbitux, Herceptin, Sutent (sunitinib malate), and Lapatinib.

Useful compounds also include nucleic acids, for example, nucleic acids that inhibit the mRNA or protein expression of a HER (e.g., ErbB-2), for example, an antisense oligonucleotide that hybridizes to a HER mRNA transcript, or a HER-specific small interference RNA (siRNA) (e.g., an ErbB-2-specific siRNA). Antisense oligonucleotides hybridize to HER transcripts and have the effect in the cell of inhibiting expression of a HER (e.g., ErbB-2).

Antisense compounds are generally used to interfere with protein expression either by, for example, interfering directly with translation of a target mRNA molecule, by RNAse-H-mediated degradation of the target mRNA, by interference with 5' capping of mRNA, by prevention of translation factor binding to the target mRNA by masking of the 5' cap, or by inhibiting of mRNA polyadenylation. The interference with protein expression arises from the hybridization of the antisense compound with its target mRNA. A specific targeting site on a target mRNA of interest for interaction with a antisense compound is chosen. Thus, for example, for modulation of polyadenylation a preferred target site on an mRNA target is a polyadenylation signal or a polyadenylation site. For diminishing mRNA stability or degradation, destabilizing sequences are preferred target sites. Once one or more target sites have been identified, oligonucleotides are chosen which are sufficiently complementary to the target site (i.e., hybridize sufficiently well under physiological conditions and with sufficient specificity) to give the desired effect.

With respect to this invention, the term "oligonucleotide" refers to an oligomer or polymer of RNA, DNA, a combination of the two, or a mimetic of either. The term includes oligonucleotides composed of naturally-occurring nucleobases, sugars, and covalent internucleoside (backbone) linkages. The normal linkage or backbone of RNA and DNA is a 3' to 5' phosphodiester bond. The term also refers however to oligonucleotides composed entirely of, or having portions containing, non-naturally occurring components which function in a similar manner to the oligonucleotides containing only naturally-occurring components. Such modified substituted oligonucleotides are often preferred over native forms because of desirable properties such as, for example, enhanced cellular uptake, enhanced affinity for target sequence, and increased stability in the presence of nucleases.

In the mimetics, the core base (pyrimidine or purine) structure is generally preserved but (1) the sugars are either modified or replaced with other components and/or (2) the inter-nucleobase linkages are modified. One class of nucleic acid mimetic that has proven to be very useful is referred to as protein nucleic acid (PNA). In PNA molecules the sugar backbone is replaced with an amide-containing backbone, in particular an aminoethylglycine backbone. The bases are retained and are bound directly to the aza nitrogen atoms of the amide portion of the backbone. PNA and other mimetics useful in the instant invention are described in detail in U.S. Pat. No. 6,210,289, the disclosure of which is incorporated herein by reference in its entirety.

The antisense oligomers to be used in the methods of the invention generally comprise about 8 to about 100 (e.g., about 14 to about 80 or about 14 to about 35) nucleobases (or nucleosides where the nucleobases are naturally occurring).

The antisense oligonucleotides can themselves be introduced into a cell or an expression vector containing a nucleic sequence (operably linked to a TRE) encoding the antisense oligonucleotide can be introduced into the cell. In the latter case, the oligonucleotide produced by the expression vector is an RNA oligonucleotide and the RNA oligonucleotide will be composed entirely of naturally occurring components.

Also useful in the method of inhibiting the expression of a HER (e.g., HER2/ErbB2) are double-stranded small interference RNA (siRNA) homologous to HER (e.g., HER2/ErbB2) DNA, which can be used to reduce expression of a HER in a cell. See, e.g., Fire et al. (1998) Nature 391:806-811; Romano and Masino (1992) Mol. Microbiol. 6:3343-3353; Cogoni et al. (1996) EMBO J. 15:3153-3163; Cogoni and Masino (1999) Nature 399:166-169; Misquitta and Paterson (1999) Proc. Natl. Acad. Sci. USA 96:1451-1456; and Kennerdell and Carthew (1998) Cell 95:1017-1026. The disclosures of all these articles are incorporated herein by reference in their entirety.

The sense and anti-sense RNA strands of siRNA can be individually constructed using chemical synthesis and enzymatic ligation reactions using procedures known in the art. For example, each strand can be chemically synthesized using naturally occurring nucleotides or variously modified nucleotides designed to increase the biological stability of the molecule or to increase the physical stability of the duplex formed between the sense and anti-sense strands, e.g., phosphorothioate derivatives and acridine substituted nucleotides. Some of the nucleotides (e.g., the terminal (either terminus) one, two, three, or four nucleotides) can also be deoxyribonucleotides. The sense or anti-sense strand can also be produced biologically using an expression vector into which a target HER sequence (full-length or a fragment) has been subcloned in a sense or anti-sense orientation. The sense and anti-sense RNA strands can be annealed in vitro before delivery of the dsRNA to cells. Alternatively, annealing can occur in vivo after the sense and anti-sense strands are sequentially delivered to cells.

The subjects can be further treated with (e.g., be exposed to, have delivered, or have administered) one or more additional therapeutic (e.g., chemotherapeutic agents) as described above. Such therapeutic or chemotherapeutic agents can include any of the therapeutic or chemotherapeutic agents described herein. Subjects can also be further treated with one or more kinase inhibitors (e.g., antibodies that inhibit receptor tyrosine kinases (e.g., Herceptin), or small molecules that inhibit tyrosine kinases (e.g., Iressa, Tarceva, Gleevec, Sutent (sunitinib malate), or Lapatinib).

1. In Vitro Methods of Inhibiting MUC1 Expression by Inhibiting a Human Epidermal Growth Factor Receptor (HER)

The invention provides an in vitro method of inhibiting MUC1 expression by inhibiting a HER (e.g., HER2). The method includes the steps of: identifying a cell as expressing MUC1, and culturing a cell with a compound that inhibits a HER such as HER2. Such methods can have general applicability in scientific studies on the role of MUC1 in HER signal transduction pathways (e.g., the ErbB2 signal transduction pathway). These methods can also be useful in any studies where inhibition of a HER is advantageous. Furthermore, as above, such in vitro methods of inhibiting a HER can be used as secondary assays in screening cascades in the pursuit of inhibitors of the MUC1-HER regulatory axis. Moreover, it can also serve as a "positive control" in assays to identify compounds with the same activity.

Methods for identifying or detecting a cell as expressing MUC1 mRNA or protein are well known to those in the art and are described above. These same methods can also be used to detect inhibition of MUC1 mRNA or protein expression. Methods for culturing a cell with an inhibitor are widely known in the art and also described above. Suitable concentrations of the inhibitory compound can be elucidated through routine experimentation and such optimization is well known to one of skill in the art. As described above, the cell may be co-cultured with one or more additional therapeutic or chemotherapeutic agents (e.g., an anti-cancer therapy or anti-inflammatory).

Suitable methods of determining inhibition of HER expression, HER kinase activity, or one or more downstream effects of a HER such as inhibition of (i) cell growth (cell proliferation), (ii) cell viability, (iii) mRNA or protein expression of MUC1, or (iv) src-dependent phosphorylation of MUC1 (e.g., phosphorylation of the MUC1-CD of SEQ ID NO:2 at tyrosine-46; are described herein (see below).

Inhibition of MUC1 expression can be inhibition of MUC1 mRNA or MUC1 protein expression. It is also understood that inhibition of MUC1 expression also includes increased degradation of MUC1 mRNA and/or protein.

Exemplary, but certainly not exhaustive, methods of determining inhibition of HER expression, either mRNA or protein expression, are described above. Others are known in the art.

Methods of determining the inhibition of HER kinase activity are well known in the art. Inhibition of the kinase activity of a HER (e.g., HER2) can be measured by monitoring the phosphorylation state of the receptor itself (autophosphorylation), or one or more endogenous, natural substrates of a HER receptor (e.g., HER2) (e.g., substrates such as β-catenin, β4-integrin, Erbin). Sometimes, for example, where the basal amount of HER autophosphorylation or phosphorylation of its substrates is low, it can be preferable to also stimulate (e.g., activate) the receptor by treating the cells with an appropriate, cognate ligand (e.g., heregulin). The phosphorylation state of the HER receptor or one or more of HER substrates can be measured in intact cells using antibody-mediated immunofluorescence or immunohistochemical techniques. For example, cells can be fixed (e.g., with formaldehyde or paraformaldehyde), permeabilized (e.g., with a detergent such as Triton), and contacted with a primary antibody specific for a phosphorylated form of the HER receptor itself (an autophosphorylated form) or a phosphorylated form of one or more substrates of a HER (e.g., HER2), e.g., phospho-β-catinin. As described above, the primary antibody can be detectably labeled, or a secondary agent can be applied (e.g., a secondary antibody that recognizes the primary antibody) that is detectably labeled. Alternatively, the primary antibody can be, e.g., covalently conjugated to a first member of a binding pair (e.g., steptavidin or biotin) and the second member of the binding pair being coupled to a detectable label. It is understood that an decreased amount of detectable signal from the cell in the presence of a compound as compared to in the presence of the compound is an indication that less phosphorylation has occurred, and thus the compound has inhibited the HER (e.g., HER2). In some instances, the antibody can be a "pan-specific" antibody capable of recognizing any phosphorylated tyrosine (e.g., a pan-specific anti-phosphotyrosine substrate). In this way, the general phosphorylation state of a cell can be monitored in the presence and absence of a compound. Particularly when the cell has been pre-treated with a HER-specific ligand (e.g., heregulin), a lowered overall phosphorylation state of a cell in the presence of a compound as compared to the absence of a compound can be a strong indication that the compound has inhibited the HER (e.g., HER2).

It is understood that activation of HERs (e.g., HER2) by heregulin can promote the activation of downstream kinases such as src kinase. Thus, monitoring the inhibition of HER kinase activity can also be accomplished by monitoring for inhibition of one or more downstream kinases from a HER. For example, heregulin, through activation of a HER, activates src kinase, which in turn phosphorylates MUC1-CD (for example, the MUC1-CD of SEQ ID NO:2 at tyrosine-46). Both inhibition of phospho-src (activated src) and phospho-MUC1 can also be used as markers of inhibition of a HER (e.g., inhibition of HER2).

The phosphorylation state of a HER, one or more endogenous HER substrates, or one or more downstream signaling targets of a HER (e.g., src or MUC1) can alternatively be measured by solubilizing the cells in Laemmli buffer (e.g., with or with a reducing agent such as dithiothreitol or β-mercaptoethanol) and subjecting the solubilized extracts to SDS-PAGE, followed by western blotting with antibodies specific for phosphorylated residues in the HER substrate proteins (as above). Alternatively, antibodies that recognize non-phosphorylated HER substrates (e.g., non-phosphorylated MUC1 (MUC1-CD) or β-catenin) can be amenable for this assay as they can be used to detect changes in protein mobility (i.e., different mobility of a proteins through a polyacrylamide gel) consistent with protein modification (e.g., phosphorylation). For example, in some instances, phosphorylation of a protein can decrease the mobility of the protein through a matrix such as polyacrylamide, so the skilled artisan could compare the relative position of a given substrate protein in a sample treated with a compound versus a sample that was not treated with the compound.

Cell-based methods of determining inhibition of a HER can also include detecting inhibition of one or more downstream effects of a HER receptor (e.g., HER2). Such downstream effects can include, e.g., inhibition of cell proliferation. Downstream effects are also understood to include changes in expression of downstream targets of a HER receptor (e.g., targets of a the HER2).

Since activated HERs (e.g., HER2) promote cell proliferation and viability, inhibition of cell growth or apoptosis of a cell in the presence of compound can be an indication that the HER is inhibited. Methods of determining inhibition of cell proliferation are known in the art and described above. Cells can be co-cultured in the absence or presence of an appropriate inhibitory compound. In some instances, the cells can be co-cultured in the presence of a HER activator (e.g., an activator of HER2 such as heregulin). Often, a control compound (e.g., a known inhibitor of known concentration) is also added to a sample of cells as an internal standard. In addition, a sample of cells can be grown in the presence of a vehicle (e.g., carrier, buffer, or solvent) in which the compound is delivered (e.g., as a control for the effects of the vehicle). Methods of detecting (e.g., determining or measuring) cell growth inhibition by a compound are myriad and well known in the art. These methods can include, for example, counting the number of cells as described above. Another method for determining cell growth inhibition in the presence of an inhibitory compound (e.g., any one of the compositions described herein) following treatment is a metabolic assay, for example, an MTT-metabolic assay (Invitrogen, USA). MTT Diphenyltetrazolium Bromide, is a tetrazolium salt (yellowish) that is cleaved to formazan crystals by the succinate dehydrogenase system which belongs to the mitochondrial respiratory chain, and is only active in viable cells. The mitochondrial succinate dehydrogenase reduces the MTT crystals into purple formazan in the presence of an electron coupling reagent. Following the treatment of the cells with a compound, the cells are exposed to the MTT reagent and the more viable cells are present in a well, the more formazan dye is produced. Extent of formazan dye can be measured, for example, using a spectrophotometer. Other commonly used methods of detecting cell growth inhibition include the monitoring of DNA synthesis. Cells grown, for example, in the presence or absence of compound are also treated with a nucleotide anolog that can incorporate into the DNA of the cell upon cell division. Examples of such nucleotide analogs include, for example, BrdU or $^3$H-Thymidine. In each case, the amount of label incorporated into the cells (grown in the presence and absence of a given inhibitory agent) is quantified, and the amount of label incorporation is directly proportional to the amount of cell growth in the population of cells. In this context, cell proliferation (e.g., cancer cell proliferation) can be decreased by at least 10% (e.g., at least 15%, at least 20%, at least 25%, at least 30%, at least 35%, at least 40%, at least 50%, at least 55%, at least 60%, at least 65%, at least 70%, or at least 75% or more) relative to the cell proliferation in the absence of the inhibitor. It is understood that the methods described above can be used for detecting or measuring both cell proliferation and viability.

Since activation of HER2 by heregulin promotes the expression of MUC1, and MUC1 has been shown to inhibit apoptosis, another method of determining inhibition of a HER (e.g., HER2) can be detecting an increased amount of cell death. For example, cells could be cultured with a chemotherapeutic agent (e.g., carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide, podophyllotoxin, taxol, satraplatinum, 5-fluorouracil, vincristin, vinblastin, methotrexate, ara-C, taxotere, gencitabine, cisplatinum, adriamycin, or an analog of any of the aforementioned) and co-cultured in the presence and absence of a HER inhibitor (e.g., a compound of the invention or any other suitable HER inhibitors described herein). Optionally, the cells can also be cultured with, e.g., heregulin to further stimulate HER (e.g., HER2) signaling. An increased amount of cell death in the presence of a HER inhibitor indicates that the HER (e.g., HER2/ErbB2) has been inhibited.

Comparisons of apoptosis can be accomplished by measuring a host of indicators, for example, DNA fragmentation, caspase activity, loss of mitochondrial membrane potential, increased production of reactive oxygen species (ROS), intracellular acidification, chromatin condensation, phosphatidyl serine levels at the cell surface, or an increased cell permeability.

DNA fragmentation can be measured, e.g., by with the TUNEL assay (terminal deoxynucleotide transferase dUTP nick end labeling). Commercial versions of the assay are widely available, for example, APO-BrdU™ TUNEL Assay Kit (Invitrogen), APO-DIRECT™ Kit (BD-Biosciences-Pharmingen) and ApoAlert™ DNA fragmentation Assay Kit (Clontech).

Caspase activity can be measured via fluorogenic, chromogenic, and luminescent substrates specific for a given caspase (e.g., Caspase 3 or Caspase 9). Commercial kits are available for a variety of caspases such as caspase 3, caspase 7, caspase 8, and caspase 9 (see BD-Pharmingen or Invitrogen).

Loss of mitochondrial membrane potential can be measured with fluorescent dyes that selectively accumulate in various compartments of the mitochondria based on their integrity and functionality. One non-limiting example of such a dye is Mitotracker Red (Invitrogen).

Production of reactive oxygen species can be monitored with fluorescent dyes such as H2DCFDA.

Chromatin condensation can be measured with dyes such as Hoechst 33342 or propidium iodide.

Phosphotidyl serine (PS) levels can be measured at the cell surface. For example, Annexin V having a high affinity for PS, can be used to as a probe for PS on a cell surface. Numerous commercially available assay kits are suitable for such measurements (see BD-Biosciences Pharmingen).

2. In Vivo Methods of Inhibiting MUC1 Expression by Inhibiting a Human Epidermal Growth Factor Receptor (HER)

The invention features an in vivo method of inhibiting a HER, which includes the steps of: optionally identifying a subject as having, or at risk of developing, a cancer comprising one or more cancer cells expressing MUC1; and delivering to the subject a compound that inhibits a HER (e.g., ErbB2). The method can also include the steps of (i) determining whether the one or more cancer cells of the subject's cancer express MUC1 and/or (ii) determining whether inhibition of MUC1 expression and/or inhibition of a HER occurred.

In one in vivo approach, a compound that inhibits a HER (e.g., HER2) is administered to a subject (e.g., any of the subjects described herein). The compounds of the invention will, generally, be suspended in a pharmaceutically-acceptable carrier (e.g., physiological saline) and administered by any of the methods described herein. Required dosage and administration schedules depends on a variety of factors set forth in the preceding sections. The compound can be administered alone (as a monotherapy) or can be administered in conjunction (as a multi-therapy regimen) with one or more additional therapeutic agents (e.g., Iressa, Tarceva, Erbitux, Herceptin, Sutent (sunitinib malate), Lapatinib, or any other suitable therapies such as, but not limited to, those described herein.

Where an inhibitory compound is a polypeptide, a polynucleotide containing a nucleic acid sequence encoding the polypeptide can be delivered to appropriate cells in a mammal as described in detail above.

3. Ex Vivo Methods of Inhibiting MUC1 Expression by Inhibiting a Human Epidermal Growth Factor Receptor (HER)

An ex vivo strategy can involve transfecting or transducing cells obtained from the subject or another subject with a polynucleotide encoding a polypeptide that inhibits a HER (e.g., HER2). The transfected or transduced cells are then administered to the subject. The cells can be any of a wide range of types including, without limitation, any of the cells described above. Such cells act as a source of the inhibitory polypeptide for as long as they survive in the subject. Alternatively, tumor cells or immune cells, preferably obtained from the subject (autologous) but potentially from a subject of the same species other than the subject (allogeneic), can be transfected or transformed by a vector encoding the inhibitory polypeptide. The tumor cells, preferably treated with an agent (e.g., ionizing irradiation) that ablates their proliferative capacity, are then introduced into the subject, where they secrete the polypeptide.

The ex vivo methods include the steps of harvesting cells from a subject, culturing the cells, transducing them with an expression vector, and maintaining the cells under conditions suitable for expression of the polypeptide that inhibits a HER (e.g., HER2/ErbB2). These methods are known in the art of molecular biology and suitable methods are described above.

J. Methods of Inhibiting MUC1 Expression by Inhibiting an Interaction Between Heregulin and a HER Provided herein are in vitro, in vivo, and ex vivo methods of inhibiting MUC1 expression by inhibiting an interaction between heregulin and a HER (e.g., HER1, HER2, HER3, or HER4). While the invention is not limited by any particular theory or mechanism of action, heregulin (through its binding to a HER) promotes the expression of MUC1 and thus the development or viability of a cancer cell (e.g., in a human tumor). Therefore, inhibition of this interaction can have general applicability in inhibiting the growth or viability of a cancer cell. Inhibition of cell growth can be a static, reversible inhibition of cell growth as described above. Where the methods are in vivo or ex vivo, such methods can also be useful in the treatment of cancers or inflammatory diseases.

Inhibition of the interaction between heregulin and a HER can include inhibition of an interaction between heregulin (e.g., heregulin alpha or heregulin beta) and any HER protein (e.g., HER1, HER2, HER3, or HER4) described herein. Similarly, heregulin, as referred to in the method, can include full-length, wild-type, mature heregulin alpha or beta polypeptides, or a functional or HER-binding fragment of a heregulin polypeptide. Cells useful in the methods described herein include any cell (e.g., any mammalian cell) that expresses an appropriate HER receptor (e.g., HER1, HER2, HER3, or HER4).

The methods of inhibiting an interaction between heregulin and an HSF can optionally include a step of identifying a cell as one expressing MUC1 and or optionally identifying a cell as one expressing a HER (e.g., HER1, HER2, HER3, or HER4). Expression can be mRNA or MUC1 protein and suitable methods of identifying (or detecting) the expression of proteins or mRNAs are described herein.

Compounds useful in the methods of inhibiting an interaction between heregulin (e.g., heregulin alpha or heregulin beta) and a HER (e.g., HER1, HER2, HER3, or HER4) can include any of the compounds described herein, or any other compounds with the appropriate inhibitory activity. Suitable compounds can include small molecules, antibodies, an antibody fragments, polypeptides, or a peptidomimetics. Compounds can also include nucleic acids, for example, nucleic acids that inhibit the mRNA or protein expression of heregulin or more particularly the HER (e.g., HER1, HER2, HER3, or HER4) (e.g., siRNA or anti-sense nucleic acids; see "Methods of Inhibiting HER"). Other exemplary compounds for use in the methods include HER polypeptides or their functional fragments (e.g., decoy receptors capable of binding soluble heregulin and preventing the binding of heregulin to the cell surface). Examples of potential functional fragments of a HER include, for example, the extracellular domain of a HER (e.g., HER1, HER2, HER3, or HER4) or heregulin-binding fragments thereof.

While the invention is not limited by any particular mechanism of action, it appears that the binding of heregulin to a HER promotes MUC1 expression. Thus, co-culturing a cell in the presence of, or further administering to a subject (e.g., a human patient), an inhibitor of an interaction between heregulin and a HER (e.g., HER1, HER2, HER3, or HER4) (thereby reducing MUC1 expression) and one or more additional therapeutic agents can increase the efficacy of the one or more therapeutic agents (e.g., one or more therapeutic agents for the treatment of cancer). In some embodiments of the methods of inhibiting the interaction between heregulin and a HER (e.g., HER1, HER2, HER3, or HER4), the cells or subjects can be further treated with one or more additional therapeutic agents as above. Such therapeutic agents can include, but are not limited to, one or more chemotherapeutic agents, one or more forms of ionizing radiation, or hyperthermotherapy, such as any of those described herein.

1. In vitro Methods of Inhibiting MUC1 Expression by Inhibiting an Interaction Between Heregulin and a HER Provided herein is an in vitro method of inhibiting MUC1 expression by inhibiting an interaction between heregulin reagent and a HER (e.g., HER1, HER2, HER3, or HER4) reagent. The method can be useful, for example, in scientific studies investigating the role of heregulin or HERs in the control of MUC1 expression or cancer, or any other scientific studies in which inhibiting the interaction between heregulin and a HER (e.g., HER1, HER2, HER3, or HER4) can be beneficial. Where the method is a cell-based method, it can also be useful as a further screening step, in e.g., a drug screening cascade, following the biochemical (e.g., a cell-free method of identifying a compound that inhibits the binding of heregulin to a HER described above) identification of a compound that inhibits the binding of heregulin to a HER. Moreover, it can also serve as a "positive control" in assays to identify compounds with the same activity.

The method can include the steps of: identifying a cell as one expressing MUC1 (e.g., a cell expressing MUC1 protein or MUC1 mRNA), and culturing the cell with a compound that inhibits the interaction between heregulin (e.g., heregulin alpha or heregulin beta) and a HER (e.g., HER1, HER2, HER3, or HER4). The cell can be any of the cells described herein (e.g., see above). As described above, the cell may be co-cultured with one or more additional therapeutic agents.

Methods of determining or detecting the inhibition of an interaction between heregulin and a HER (e.g., HER1, HER2, HER3, or HER4) are known in the art, and include, for example, (i) in vitro or in situ methods of detecting inhibition of binding of heregulin to a HER or (ii) inhibition of the activation of a HER following binding of heregulin. Inhibition of the activation of a HER following binding of heregulin includes, for example, inhibition of HER autophosphorylation, inhibition of the phosphorylation of a substrate by a HER, or inhibition of one of the aforementioned downstream effects of HER activation (see above).

Methods of determining inhibition of the binding between heregulin and a HER can be cell-free methods. For example, HER polypeptide (e.g., a HER polypeptide capable of being heregulin such as HER1, HER2, HER3, or HER4) can be adhered to a solid phase matrix (e.g., a multi-well assay plate, see above). The HER polypeptide can be recombinant protein or endogenous protein (e.g., endogenous protein expressed by a cell). The HER polypeptide can be applied to the well as a pure solution (e.g., purified HER protein in a buffer such as phosphate buffered saline or Tris-HCl-buffered saline) or can be applied as a heterogenous mixture, e.g., as part of cell lysate prepared from cells expressing the HER. Non-bound HER can be removed by subsequent wash steps. In the presence or absence of an inhibitor (e.g., an inhibitor of the interaction between heregulin and a HER), a heregulin reagent (e.g., heregulin alpha or heregulin beta or a HER-binding fragment of either, see above) can be added to the bound HER. The heregulin can be itself conjugated to a detectable label (for example any of the detectable labels described herein). Where the heregulin reagent is not detectably labeled, a detectably labeled primary antibody specific for heregulin can be used to detect the bound heregulin. Alternatively, as above, the primary antibody can be unlabeled and a detectably-labeled secondary agent (e.g., a detectably labeled secondary antibody specific for the primary antibody) can be used to detect the binding of heregulin to the HER. In any of the above-mentioned methods, a decrease in the amount of detectable label detected in the presence of compound as compared to the absence of the compound is an indication that the compound has inhibited the interaction between heregulin and the HER. More detailed methods of ELISA-type assays are described above (see, e.g., "Methods of Screening for Inhibitory Compounds: The MUC1-HSF Interaction").

Co-immunoprecipitation experiments can also be used to determine the inhibition of an interaction between heregulin (e.g., heregulin alpha or heregulin beta) and a HER. For example, whole cell lysates can be prepared from cells expressing a HER receptor and incubated with a known amount of heregulin in the presence and absence of an inhibitor of the interaction between heregulin and the HER. Antibodies specific for either the HER or heregulin (e.g., an anti-heregulin alpha or an anti-HER3 antibody) can be contacted with the lysates and used to immunoprecipitate the protein to which the antibody is specific. Immunoprecipitates can be isolated, washed, and subjected to SDS-PAGE. The amount of the various proteins in the immunoprecipitates can be determined by western blot using antibodies specific for the proteins as described above. For example, the amount of heregulin bound to HER in a sample can be determined by immunoprecipitating either the heregulin or the HER molecule with antibodies specific for either heregulin or the HER molecule respectively. In this case, a reduction in the amount of heregulin in a HER immunoprecipitate or a reduction in the amount of HER in a heregulin immunoprecipitate is an indication that the compound inhibited the interaction between heregulin and the HER. Alternatively, purified, recombinant heregulin and purified recombinant HER polypeptides can be incubated together in the presence or absence of the compound and subsequently immunoprecipitated as described above.

Another method of determining inhibition of an interaction between heregulin (e.g., heregulin alpha or heregulin beta) is an in situ staining method. In situ immunostaining methods are well known in the art and include embodiments where the cells are still viable (e.g., confocal microscopy of live cells) or fixed cells (e.g., immunohistochemistry). Briefly, cells expressing an appropriate HER can be contacted with a heregulin in the presence or absence of an inhibitor of the interaction between heregulin and the HER. The heregulin itself can be detectably labeled or antibodies specific for heregulin can be applied (e.g., administered, delivered, contacted) to cells. The antibodies directly labeled with a detectable label (e.g., a different colored fluorophore (e.g., rhodamine, texas red, FITC, Green fluorescent protein, Cy3, Cy5) or a secondary agent (e.g., a secondary antibody specific for the primary antibody) can be detectably labeled. Use of an appropriate microscope (e.g., a confocal microscope) with the appropriate optical filters can identify (i.e., detect) the presence or amount of bound heregulin. A reduction in the amount of signal detected on the cell indicates that the compound inhibits the binding of heregulin to the HER.

Methods of detecting inhibition of the activation of a HER following binding of heregulin such as, but not limited to, inhibition of HER autophosphorylation, inhibition of the phosphorylation of a substrate by a HER, or inhibition of one of the aforementioned downstream effects of HER activation are described above in the section entitled "Methods of Inhibiting a Human Epidermal Growth Factor Receptor (HER)." While the invention is not limited by any particular mechanism of action, it is understood that while heregulin may not physically associate with the ErbB2 receptor, due to HER heterodimerization, heregulin can in fact activate and signal through ErbB2. Thus, inhibition of the activation of a HER can also include inhibition of the activation of ErbB2/HER2/neu.

2. In Vivo Methods of Inhibiting MUC1 Expression by Inhibiting an Interaction Between Heregulin and a HER The invention features an in vivo method of inhibiting MUC1 expression by inhibiting an interaction between heregulin and a HER (e.g., HER1, HER2, HER3, or HER4), which includes the steps of: optionally identifying a subject as having, or at risk of developing, (or suspected of having) a cancer comprising one or more cancer cells expressing MUC1; and delivering to the subject a compound that inhibits an interaction between heregulin and a HER (e.g., HER1, HER2, HER3, or HER4). The method can optionally include the steps of: (i) determining whether the one or more cancer cells of the subject's cancer express MUC1 and/or (ii) determining whether inhibition of MUC1 expression and/or an interaction between heregulin and a HER has occurred.

In one in vivo approach, a compound that inhibits an interaction between heregulin and a HER (e.g., HER1, HER2, HER3, or HER4) is administered to a subject (e.g., any of the subjects described herein). The compounds of the invention will, generally, be suspended in a pharmaceutically-acceptable carrier (e.g., physiological saline) and administered by any of the methods described herein. Required dosage and administration schedules depends on a variety of factors set forth in the preceding sections. The compound can be administered alone (as a monotherapy) or can be administered in conjunction (as a multi-therapy regimen) with one or more additional therapeutic agents (e.g., Iressa, Tarceva, Erbitux, Herceptin, Sutent (sunitinib malate), Lapatinib, or any other suitable therapies such as, but not limited to, those described herein), or one or more additional treatments such as a treatment for pain or anemia.

Where an inhibitory compound is a polypeptide, a polynucleotide containing a nucleic acid sequence encoding the polypeptide can be delivered to appropriate cells in a mammal as described in detail above.

3. Ex Vivo Methods of Inhibiting MUC1 Expression by Inhibiting an Interaction Between Heregulin and a HER (e.g., HER3 or HER4)

An ex vivo strategy can involve transfecting or transducing cells obtained from the subject or another subject with a polynucleotide encoding a polypeptide that inhibits an interaction between heregulin and a HER (e.g., HER1, HER2, HER3, or HER4). The transfected or transduced cells are then administered to the subject. The cells can be any of a wide range of types including, without limitation, any of the cells described above. Such cells act as a source of the inhibitory polypeptide for as long as they survive in the subject. Alternatively, tumor cells or immune cells, preferably obtained from the subject (autologous) but potentially from a subject of the same species other than the subject (allogeneic), can be transfected or transformed by a vector encoding the inhibitory polypeptide. The tumor cells, preferably treated with an agent (e.g., ionizing irradiation) that ablates their proliferative capacity, are then introduced into the subject, where they secrete the polypeptide.

The ex vivo methods include the steps of harvesting cells from a subject, culturing the cells, transducing them with an expression vector, and maintaining the cells under conditions suitable for expression of the polypeptide that inhibits an interaction between heregulin and a HER (e.g., HER3 or HER4). These methods are known in the art of molecular biology and suitable methods are described above.

K. Methods of Inhibiting MUC1 Expression by Inhibiting IL-6 Receptor (IL-6R)

Provided herein are in vitro, in vivo, and ex vivo methods of inhibiting MUC1 expression by inhibiting the human IL-6 receptor (IL-6R) or a homolog of the human IL-6R. While the invention is not limited by any particular theory or mechanism of action, it appears that IL-6, through IL-6R-dependent signaling, induces MUC1 expression and thereby promotes the development or viability of a cancer cell (e.g., in a human tumor) or an immune cell (e.g., an immune cell involved in inflammation). Thus, inhibition of IL-6R can have general applicability in inhibiting the growth or viability of a cancer cell or an immune cell (e.g., autoimmune cells) through its effect on MUC1 expression. As above, where the methods are in vivo or ex vivo, such methods can also be useful in the treatment of cancers (e.g., any of the cancer types described herein) or inflammatory conditions (e.g., rheumatoid arthritis or any of the inflammatory conditions described herein).

Inhibition of a IL-6R includes inhibition of the expression of IL-6R (e.g., mRNA or protein expression of a IL-6R), the kinase activity of IL-6R, or inhibition of one or more downstream effects of IL-6R. Expression of IL-6R can include both expression of mRNA and protein. Inhibition of kinase activity can include inhibition of the autophosphorylation activity of IL-6R or the phosphorylation of one or more substrates of IL-6R.

Where the methods include the optional step of identifying a cell as one expressing IL-6R, such identification can include, for example, identifying (or detecting) whether a cell expresses IL-6R mRNA or IL-6R protein. Suitable methods of identifying (or detecting) the expression of IL-6R protein or mRNA are well known in the skill and are described herein. It is understood that the same types of methods apply where the methods include the step of identifying a cell (e.g., a cancer cell or a immune cell) as one expressing MUC1.

Compounds useful in the methods of inhibiting IL-6R include any of the compounds described herein, or any other compounds with the appropriate inhibitory activity. Suitable compounds can include small molecules, antibodies, an antibody fragments, polypeptides, or a peptidomimetics.

In some instances, inhibition of IL-6R is inhibition of the kinase activity of IL-6R. Several exemplary compounds for inhibiting IL-6R are well known to those in the art and include, for example, Actermra® (tocilizumab), PT, MRA, and SANT-7 (see, for example, Smolen et al. (2006) Arthritis Res. & Ther. 8(Suppl. 2):S5; Nishimoto et al. (2005) Blood 106(8):2627-2632; Yang et al (2005) Mol. Immunol. 42(9): 1015-1021; and Honemann et al. (2001) Int. J. Cancer 93(5): 674-680).

Compounds can also include nucleic acids, for example, nucleic acids that inhibit the mRNA or protein expression of IL-6R, for example, an antisense oligonucleotide that hybridizes to IL-6R mRNA transcript, or a IL-6R-specific small interference RNA (siRNA) (e.g., an IL-6R-specific siRNA). Antisense oligonucleotides hybridize to IL-6R transcripts and have the effect in the cell of inhibiting expression of IL-6R.

The subjects can be further treated with (e.g., be exposed to, have delivered, or have administered) one or more additional therapeutic (e.g., chemotherapeutic agents) as described above. Such therapeutic or chemotherapeutic agents can include any of the therapeutic or chemotherapeutic agents described herein. Subjects can also be co-administered one or more agents used to treat an inflammatory condition such as any of those described above. Treatments can include, e.g., non-steroidal anti-inflammatory drugs (NSAIDs) (e.g., aspirin, ibuprofen, naproxen sodium and ketoprofen), COX-2 inhibitors, disease-modifying anti-rheumatic drugs (DMARDS) (e.g., methotrexate, hydroxychloroquine, penicillamine, or gold injections); biological response modifiers (e.g., tumor necrosis factor (TNF) inhibitors); or corticosteroids (e.g., prednisone) or any other described herein.

1. In Vitro Methods of Inhibiting MUC1 Expression by Inhibiting IL-6R

The invention provides an in vitro method of inhibiting MUC1 expression. The method includes the steps of: identifying a cell as expressing MUC1, and culturing a cell with a compound that inhibits an IL-6R reagent such as human IL-6R. Such methods can have general applicability in scientific studies on the role of MUC1 in IL-6R signal transduction pathways or in studies into the role of MUC1 or IL-6 in inflammation. These methods can also be useful in any studies where inhibition of IL-6R is advantageous. Furthermore, as above, such in vitro methods of inhibiting IL-6R can be used as secondary assays in screening cascades in the pursuit of inhibitors of the MUC1-IL-6R regulatory axis. Moreover, it can also serve as a "positive control" in assays to identify compounds with the same activity.

Methods for identifying or detecting a cell as expressing MUC1 mRNA or protein are well known to those in the art and are described above. Methods for culturing a cell with an inhibitor are widely known in the art and also described above. Suitable concentrations of the inhibitory compound can be elucidated through routine experimentation and such optimization is well known to one of skill in the art. As described above, the cell may be co-cultured with one or more additional therapeutic or chemotherapeutic agents (e.g., an anti-cancer therapy or anti-inflammatory).

Methods of determining inhibition of MUC1 expression (e.g., inhibition of MUC1 mRNA or protein expression) or increased degradation of MUC1 mRNA or MUC1 protein are described above.

Suitable methods of determining inhibition of IL-6R expression, IL-6R kinase activity, or one or more downstream effects of a IL-6R are described herein (see below).

Exemplary, but not in any exhaustive, methods of determining inhibition of IL-6R expression, either mRNA or protein expression, are described above.

Methods of determining the inhibition of IL-6R kinase activity are well known in the art. Inhibition of the kinase activity of IL-6R can be measured by monitoring the phosphorylation state of the receptor itself (autophosphorylation), or one or more endogenous, natural substrates of IL-6R (e.g., substrates such as GP130 or janus activated kinase (JAK)). Inhibition of IL-6R can also be determined by monitoring the phosphorylation of a downstream signaling target of IL-6R such as STAT3 (e.g., the phosphorylation of STAT3 by JAKs). Sometimes, for example, where the basal amount of IL-6R autophosphorylation or phosphorylation of its substrates is low, it can be preferable to also stimulate (e.g., activate) the receptor by treating the cells with an appropriate, cognate ligand (e.g., IL-6). The phosphorylation state of IL-6R receptor or one or more of IL-6R substrates can be measured in intact cells using antibody-mediated immunofluorescence or immunohistochemical techniques as described above (see, "In vitro Methods of Inhibiting MUC1 Expression by Inhibiting a Human Epidermal Growth Factor (HER)").

The phosphorylation state of one or more endogenous IL-6R substrates can alternatively be measured by methods described above.

Cell-based methods of determining inhibition of IL-6R can also include detecting inhibition of one or more downstream effects of IL-6R. Such downstream effects can include, e.g., inhibition of cell proliferation. Downstream effects are also understood to include, for example, changes in expression (e.g., inhibition of expression) of downstream targets of a IL-6R receptor such as MUC1, changes in the phosphorylation state (e.g., reduction in phosphorylation) of any of several proteins in the known IL-6 signaling pathway, or inhibition of STAT3 activity.

Since activated IL-6R promotes cell proliferation and viability, inhibition of cell growth or apoptosis of a cell in the presence of compound can be an indication that IL-6R is inhibited. Methods of determining inhibition of cell proliferation, viability, and apoptosis are known in the art and described above.

Methods for determining inhibition of expression of a target gene (e.g., MUC1) are also described herein.

Suitable methods for detecting a change in STAT3 activity are also described herein. STAT3 activity can be monitored by detecting STAT3 transcription activation activity, translocation of STAT3 to the nucleus of a cell.

Inhibition STAT3 transcriptional activity, as a measure of inhibition of IL-6R, can be monitored by cell-based methods involving monitoring the expression of STAT3 target genes or using a STAT3-driven reporter vector construct. Both of these methods are described above.

Methods of monitoring inhibition of STAT3 translocation to the cell nucleus, as a measure of inhibition of IL-6R, can include (but do not necessarily require) the administration of a cytokine (e.g., IL-6) or other appropriate IL-6R stimulating agents to activate STAT3 and promote its nuclear localization. A compound can thus be co-administered with the stimulator to assess the inhibition of STAT3 translocation. Thus, more nuclear localization of STAT3 in the absence of a compound as compared to the nuclear localization in the presence of the compound indicates that the compound has inhibited the nuclear localization of STAT3. Nuclear localization of STAT3 can be detected, for example, by cell fractionation (i.e., detecting the amount of STAT3 in a cytosolic versus a nuclear extract prepared from the same source of cells) and immunoblotting or ELISA. Alternatively, localization of STAT3 can be done in situ, generally by methods including, but not limited to: (i) fixing the cells; (ii) treatment of the fixed cells with detectably-labeled antibodies specific to STAT3; and (iii) detecting the signal produced by the detectable label using any of a number of methods known to those in the art, including FFC and confocal microscopy. The detectable label can be conjugated to the first antibody (the primary antibody which specifically recognizes STAT3) or on a secondary antibody which is capable of binding to the first antibody. Alternatively, the first antibody can be conjugated to the first member of a binding pair (i.e., strepavidin or biotin) and the second member of the binding pair can be linked to the detectable reagent. The detectable reagent can include radiolabels (e.g., $^{125}I$, $^{35}S$, $^{33}P$, or $^{32}P$), fluorescent labels (e.g., texas red, fluorescein), a luminescent reagent (e.g., a lanthanide), or a one or more members of a FRET pair.

Alternatively, inhibition of STAT3, as a measure of inhibition of IL-6R, can also involve inhibition of the binding of STAT3 to DNA (e.g., a STAT3-binding element, e.g., the STAT3-binding element of the MUC1 promoter) and suitable methods for this are described above.

2. In Vivo Methods of Inhibiting MUC1 Expression by Inhibiting IL-6R

The invention features an in vivo method of inhibiting MUC1 expression by inhibiting IL-6R, which includes the steps of: optionally identifying a subject as having, or at risk of developing (or suspected of having), a cancer comprising one or more cancer cells expressing MUC1; and delivering to the subject a compound that inhibits IL-6R. As discussed above, the method can involve the steps of determining whether one or more cancer cells of the subject's express MUC1 and/or determining whether inhibition of IL-6R has occurred.

The invention also features an in vivo method of inhibiting MUC1 expression, which includes the steps of identifying a subject as having, or at risk of developing (or suspected of having), an inflammatory condition mediated by one or more inflammatory cells expressing MUC1; and delivering to the subject a compound that inhibits IL-6R. The method can include the steps of determining whether one or more inflammatory cells mediating the inflammatory condition express MUC1 and/or determining whether inhibition of IL-6R has occurred In one in vivo approach, a compound that inhibits IL-6R is administered to a subject (e.g., any of the subjects described herein). The compounds of the invention will, generally, be suspended in a pharmaceutically-acceptable carrier (e.g., physiological saline) and administered by any of the methods described herein. Required dosage and administration schedules depends on a variety of factors set forth in the preceding sections. The compound can be administered alone (as a monotherapy) or can be administered in conjunction (as a multi-therapy regimen) with one or more additional therapeutic agents (e.g., a chemotherapy, a therapy for an inflammatory condition, or any other suitable therapies such as, but not limited to, those described herein).

Where an inhibitory compound is a polypeptide, a polynucleotide containing a nucleic acid sequence encoding the polypeptide can be delivered to appropriate cells in a mammal as described in detail above.

3. Ex Vivo Methods of Inhibiting MUC1 Expression by Inhibiting IL-6R

An ex vivo strategy can involve transfecting or transducing cells obtained from the subject (or another subject) with a polynucleotide encoding a polypeptide that inhibits IL-6R. The transfected or transduced cells are then administered to the subject. The cells can be any of a wide range of types including, without limitation, any of the cells described above. Such cells act as a source of the inhibitory polypeptide for as long as they survive in the subject. Alternatively, tumor cells or immune cells, preferably obtained from the subject (autologous) but potentially from a subject of the same species other than the subject (allogeneic), can be transfected or transformed by a vector encoding the inhibitory polypeptide. The tumor cells, preferably treated with an agent (e.g., ionizing irradiation) that ablates their proliferative capacity, are then introduced into the subject, where they secrete the polypeptide.

The ex vivo methods include the steps of harvesting cells from a subject, culturing the cells, transducing them with an expression vector, and maintaining the cells under conditions suitable for expression of the polypeptide that inhibits IL-6R. These methods are known in the art of molecular biology and suitable methods are described above.

L. Methods of Inhibiting MUC1 Expression by Inhibiting an Interaction Between IL-6 and IL-6R Provided herein are in vitro, in vivo, and ex vivo methods of inhibiting an interaction between IL-6 and IL-6R. While the invention is not limited by any particular theory or mechanism of action, IL-6 (through its binding to IL-6R) promotes the expression of MUC1 and thus the development or viability of a cell (e.g., in a human cancer cell or a human immune cell). Therefore, inhibition of this interaction can have general applicability in inhibiting the growth or viability of a cell. Inhibition of cell growth can be a reversible inhibition of cell growth as described above. Where the methods are in vivo or ex vivo, such methods can also be useful in the treatment of cancers or inflammatory conditions such as osteoarthritis, rheumatoid arthritis, spondyloarhrophathies, or any other inflammatory conditions described herein.

Inhibition of the interaction between IL-6 and IL-6R can include inhibition of an interaction between human IL-6 (e.g., a homolog of human IL-6 or an IL-6R-binding fragment thereof) and a human IL-6R protein (e.g., a homolog of human IL-6 or a extracellular portion or IL-6 binding fragment thereof) described herein. The cell can include any cell (e.g., any mammalian cell) that expresses IL-6R receptor.

The methods of inhibiting an interaction between IL-6 and IL-6R can optionally include a step of identifying a cell as one expressing MUC1 and/or optionally identifying a cell as one expressing IL-6R. Expression can be mRNA or protein and suitable methods of identifying (or detecting) the expression of proteins or mRNAs are described herein.

Compounds useful in the methods of inhibiting an interaction between IL-6 and IL-6R can include any of the compounds described herein, or any other compounds with the appropriate inhibitory activity. Suitable compounds can include small molecules, antibodies, an antibody fragments, polypeptides, or a peptidomimetics. Compounds can also include nucleic acids, for example, nucleic acids that inhibit the mRNA or protein expression of IL-6 or more particularly the IL-6R (e.g., siRNA or anti-sense nucleic acids; see "Methods of Inhibiting HER"). Other exemplary compounds for use in the methods include IL-6R polypeptides or their functional fragments (e.g., decoy receptors capable of binding soluble IL-6 and preventing the binding of IL-6 to the cell surface). Examples of potential functional fragments of IL-6R include, for example, the extracellular domain of IL-6R or IL-6-binding fragments thereof.

While the invention is not limited by any particular mechanism of action, it seems likely that the binding of IL-6 to IL-6R promotes MUC1 expression. Thus, co-culturing a cell in the presence of, or further administering to a subject (e.g., a human patient), an inhibitor of an interaction between IL-6 and IL-6R and one or more additional therapeutic agents can increase the efficacy of the one or more therapeutic agents, e.g., in the treatment of cancer or the treatment of an inflammatory condition. In methods of inhibiting the interaction between IL-6 and IL-6R, the cells or subjects can be further treated with one or more additional therapeutic agents as above. Such therapeutic agents can include, but are not limited to, one or more chemotherapeutic agents, one or more forms of ionizing radiation, or hyperthermotherapy, such as any of those described herein. Where the subject (e.g., human patient) to be treated has or is suspected of having an inflammatory condition such as rheumatoid arthritis (or any of the inflammatory conditions described herein) the subject can be further administered treatments such as, e.g., non-steroidal anti-inflammatory drugs (NSAIDs) (e.g., aspirin, ibuprofen, naproxen sodium and ketoprofen), COX-2 inhibitors, disease-modifying anti-rheumatic drugs (DMARDS) (e.g., methotrexate, hydroxychloroquine, penicillamine, or gold injections); biological response modifiers (e.g., tumor necrosis factor (TNF) inhibitors); or corticosteroids (e.g., prednisone).

1. In Vitro Methods of Inhibiting MUC1 Expression by Inhibiting an Interaction Between IL-6 and IL-6R Provided herein is an in vitro method of inhibiting an interaction between IL-6 and IL-6R. The method can be useful, for example, in scientific studies investigating the role of IL-6 or IL-6R in the control of MUC1 expression, cancer, or inflammatory conditions, or any other scientific studies in which inhibiting the interaction between an IL-6 reagent and an IL-6R reagent can be beneficial. Where the method is a cell-based method, it can also be useful as a further cell-based screening step, in e.g., a drug screening cascade, following the biochemical (e.g., a cell-free method of identifying a compound that inhibits the binding of IL-6 to IL-6R described above) identification of a compound that inhibits the binding of IL-6 to IL-6R. It can also be used as a positive control in assays to identify compounds with such activity.

The method can include the steps of: identifying a cell as one expressing MUC1 (e.g., a cell expressing MUC1 protein or MUC1 mRNA), and culturing the cell with a compound that inhibits the interaction between IL-6 and IL-6R. The cell can be any of the cells described herein (e.g., see above). As described above, the cell may be co-cultured with one or more additional therapeutic agents.

Methods of determining or detecting the inhibition of an interaction between IL-6 and IL-6R are known in the art, and include, for example, (i) in vitro or in situ methods of detecting inhibition of binding of IL-6 and IL-6R or (ii) inhibition of the activation of IL-6 following binding of IL-6. Inhibition of the activation of IL-6R following binding of IL-6 includes, for example, inhibition of IL-6R autophosphorylation, inhibition of the phosphorylation of a substrate by a IL-6R, or inhibition of one of the aforementioned downstream effects of IL-6R activation (see above).

Methods of determining inhibition of the binding between IL-6 and IL-6R can be cell-free methods. Suitable methods for detecting inhibition of an interaction of IL-6 and IL-6R can be derived from simple adaptation of methods described for "Inhibiting an Interaction Between Heregulin and a Human Epidermal Growth Factor Receptor (HER)" (see above).

Methods of detecting inhibition of the activation of IL-6R following binding of IL-6 such as, but not limited to, inhibition of IL-6R autophosphorylation, inhibition of the phosphorylation of a substrate by IL-6R, or inhibition of one of the aforementioned downstream effects of HER activation are described above in the section entitled "Methods of Inhibiting MUC1 Expression: Inhibiting IL-6R."

2. In Vivo Methods of Inhibiting MUC1 Expression by Inhibiting an Interaction Between IL-6 and IL-6R The invention features an in vivo method of inhibiting MUC1 expression, which includes the steps of: optionally identifying a subject as having, or at risk of developing (or suspected of having), a cancer comprising one or more cancer cells expressing MUC1; and delivering to the subject a compound that inhibits an interaction between IL-6 and IL-6R. The method can include the steps of (i) determining whether one or more cancer cells of the subject's cancer express MUC1 and/or (ii) determining whether inhibition of MUC1 expression and/or an inhibition of an interaction between IL-6 and IL-6R has occurred.

The invention also features an in vivo method of inhibiting MUC1 expression, which includes the steps of: identifying a subject as having, or at risk of developing (or suspected of having), an inflammatory condition mediated by one or more inflammatory cells expressing MUC1; and delivering to the subject a compound that inhibits an interaction between IL-6 and IL-6R. The method can optionally include the steps of determining whether one or more inflammatory cells involved in the inflammatory condition express MUC1 and/or (ii) determining whether inhibition of MUC1 expression and/ or an inhibition of an interaction between IL-6 and IL-6R has occurred.

In one in vivo approach, a compound that inhibits an interaction between IL-6 and IL-6R is administered to a subject (e.g., any of the subjects described herein). The compounds of the invention will, generally, be suspended in a pharmaceutically-acceptable carrier (e.g., physiological saline) and administered by any of the methods described herein. Required dosage and administration schedules depends on a variety of factors set forth in the preceding sections. The compound can be administered alone (as a monotherapy) or can be administered in conjunction (as a multi-therapy regimen) with one or more additional therapeutic agents (e.g., one or more chemotherapies or treatments for an inflammatory condition (described above), or any other suitable therapies such as, but not limited to, those described herein), or one or more additional treatments such as a treatment for pain or anemia.

Where an inhibitory compound is a polypeptide, a polynucleotide containing a nucleic acid sequence encoding the polypeptide can be delivered to appropriate cells in a mammal as described in detail above.

3. Ex Vivo Methods of Inhibiting MUC1 Expression by Inhibiting an Interaction Between IL-6 and IL-6R An ex vivo strategy can involve transfecting or transducing cells obtained from the subject (or another subject) with a polynucleotide encoding a polypeptide that inhibits an interaction between IL-6 and IL-6R. The transfected or transduced cells are then administered to the subject. The cells can be any of a wide range of types including, without limitation, any of the cells described above. Such cells act as a source of the inhibitory polypeptide for as long as they survive in the subject. Alternatively, tumor cells or immune cells, preferably obtained from the subject (autologous) but potentially from a subject of the same species other than the subject (allogeneic), can be transfected or transformed by a vector encoding the inhibitory polypeptide. The tumor cells, preferably treated with an agent (e.g., ionizing irradiation) that ablates their proliferative capacity, are then introduced into the subject, where they secrete the polypeptide.

The ex vivo methods include the steps of harvesting cells from a subject, culturing the cells, transducing them with an expression vector, and maintaining the cells under conditions suitable for expression of the polypeptide that inhibits an interaction between IL-6 and IL-6R. These methods are known in the art of molecular biology and suitable methods are described above.

M. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Induction of MUC1 Expression in the Response to Heregulin Treatment

Figure 2A:
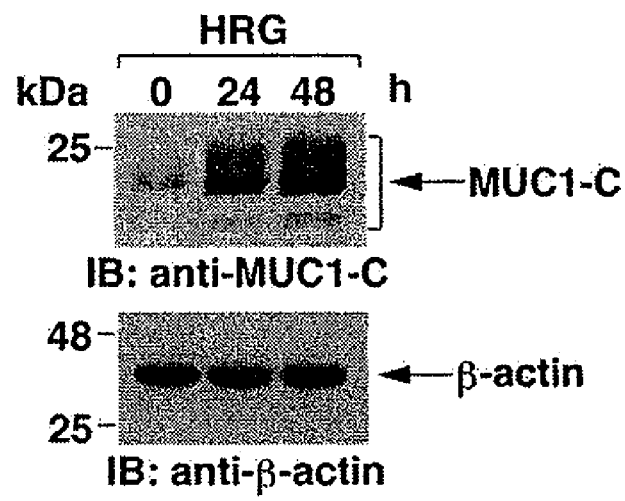
FIG. 2A is a pair of photographs of immunoblots depicting the induction of MUC1 expression following heregulin (HRG) treatment. MCF10A cells were cultured without ("0") and with HRG (20 ng/mL) for 24 ("24") and 48 ("48") hours. Cells were harvested at the indicated time points and lysed for western blot analysis. Whole-cell lysates were subjected to sodium dodecyl sulfate polyacrylamide gel electrophoresis (SDS-PAGE) under reducing conditions and proteins were detected (immunoblotted, "IB") using antibodies specific for MUC1-C and β-actin (top and bottom photographs, respectively). The relative positions (e.g., the molecular weights) of the proteins are reported in kilodaltons (kDa) and indicated to the left of each of the immunoblots (e.g., 25 kDa or 45 kDa). "HRG" indicates treatment with heregulin.

Heregulin treatment of cells results in (i) activation of ErbB2, ErbB3, and ErbB4 and (ii) induction of the formation of complexes between these receptors and MUC1. To assess if MUC1 is regulated by heregulin in normal cells, the induction of MUC1 expression by heregulin treatment was assessed in the immortalized, but non-cancer breast cell line MCF10A. MCF10A cells were grown overnight in mammary epithelial growth media (MEGM; Cambrex Corporation, East Rutherford, N.J.) and then stimulated with 20 ng/mL heregulin (HRG) (Calbiochem-Novabiochem) for 1 to 72 hours. Whole-cell lysates were prepared from the treated cell populations and were subjected to immunoblotting with anti-MUC1-C (Neomarkers, Lab Vision Corporation, Fremont, Calif.). As a control for loading, β-actin was detected using anti-β-actin (Sigma, St. Louis, Mo.). An increase in MUC1 protein expression was observed in MCF10A cells treated with HRG (FIG. 2A). Such results indicate that HRG regulates MUC1 expression in normal breast cells.

To determine if HRG regulates MUC1 expression in cancer cells, MCF-7, ZR-75-1, MB-231 and T47D breast cancer cells (cultured as described in Wei et al. (2006) Mol. Cell. 21:295-305) are grown overnight in medium with 0.1% serum. Whole-cell lysates are prepared and immunoblotted as above. Lysates are also immunoblotted with an antibody against HSF1 to assess HRG-induced HSF1 expression as previously shown in MCF-7 cells (Khaleque et al. (2005) Oncogene 24:6564-6563). No increase in MUC1 protein expression following HRG treatment in the MCF-7 breast cancer cells indicates that while HRG induces the expression of MUC1 in normal breast cells, expression of MUC1 is constitutive in cancer cells.

To investigate the signals that relay HRG-induced MUC1 expression, the MCF10A cells are preincubated with monoclonal antibodies Ab-7, Ab-5, and Ab-3, which bind to, and block HRG access to human epidermal growth factor receptors (HERs): ErbB2 (HER2), ErbB3 (HER3), and ErbB4 (HER4), respectively (Neomarkers). The cells are also pretreated with the Herceptin and 2C4 antibodies, which bind to ErbB2, and block interaction between ErbB2 and ErbB3 (Genentech, San Francisco, Calif.) (Jackson et al. (2004) Cancer Res. 64:2601-2609). The preincubations are performed at antibody concentrations of 20 μg/mL for 2 hours. Following the preincubation, the cells are treated with HRG and subsequently evaluated for MUC1 expression (as described above). Activation of ErbB2 is also confirmed by subjecting lysates to immunoblotting with anti-phospho-ErbB2-Tyr-1248 and anti-ErbB2 (Cell Signaling Technology, Danvers, Mass.). An inhibition of HRG-induced induction of MUC1 expression following pretreatment of MCF10A cells with the antibodies would indicate that HRG signals through HERs to induce MUC1 expression in normal breast cells.

Figure 2B:
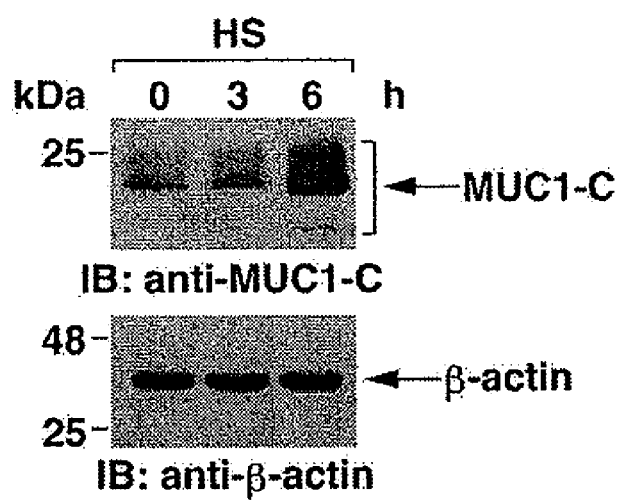
FIG. 2B is a pair of photographs of immunoblots depicting the induction of MUC1 expression following heat shock. MCF10A cells were treated without ("0") and with heat shock (1 hour at 43° C.) and then cultured at 37° C. for 3 ("3") and 6 ("6") hours. Cells were harvested at the indicated time points and lysed for western blot analysis. Whole-cell lysates were subjected to SDS-PAGE under reducing conditions and proteins were detected (immunoblotted, "IB") using antibodies specific for MUC1-C and β-actin (top and bottom photographs, respectively). The relative position (e.g., the molecular weights) of the proteins are reported in kilodaltons (kDa) and indicated to the left of each of the immunoblots (e.g., 25 kDa or 45 kDa). "HS" indicates heat shock treatment.

As described above, HRG treatment induces MUC1 expression in MCF10A cells as well as promoting an increased expression of HSF1. An HSF binding element (the Heat Shock regulatory Element or HSE) was discovered in the MUC1 promoter (see FIG. 1A). Consequently, to define the role of HSF1 in regulating MUC1 expression, cultured MCF10A cells were heated to 43° C. for 1 hour (heat shock). Following heat shock, the cells were maintained at 37° C. from 1 to 24 hours. Cells that were not heat shocked are also maintained for the same duration as a control. Whole-cell lysates were prepared from experimental and control cells and then immunoblotted with antibodies specific for MUC1-C and β-actin. As shown in FIG. 2B, an increased amount of MUC1 protein expression in MCF10A cells was observed following heat shock. Such results indicate that heat shock induces MUC1 expression in normal breast cells.

To determine if heat shock induces MUC1 expression in cancer cells, MCF-7, ZR-75-1, MB-231, and T47D breast cancer cells are cultured (as described in Wei et al. (2006) Mol. Cell. 21:295-305) and subjected to heat shock as described above. Whole-cell lysates are prepared and immunoblotted with antibodies to MUC1-C, MUC1-N, HSF1, and β-actin as a control. Stable MUC1 expression of MCF-7 with or without heat shock indicates that MUC1 is also is constitutively activated in breast cancer cells.

To determine if HSF1 is indeed responsible for HRG-induced upregulation of MUC1 expression, MCF10A cells are transfected with a HSF1 siRNA pool (Dharmacon, Lafayette, Colo.) to silence HSF1 expression. At 36 hours after transfection, the cells are treated with HRG, or as a control with heat shock, and are monitored for MUC1 and HSF1 levels by immunoblotting. As an alternative approach, the cells are also transfected to express a dominant-negative HSF1(1-379) construct (DN-HSF1; provided by Dr. S. Calderwood, Beth Israel Deaconess Medical Center) (Wang et al (2004) J. Biol. Chem. 279:32651-32659), which inhibits the endogenous HSF1 function, and then treated with HRG. Expression of MUC1 and the truncated DN-HSF1 are determined by immunoblotting SDS-PAGE resolved whole-cell lysates with anti-MUC1-C and anti-HSF1. No increased MUC1 expression following HRG treatment in MCF10A cells silenced for HSF1 or expressing DN-HSF1 would indicate that HRG signals to MUC1 through a HSF 1-dependent mechanism.

Example 2

Induction of MUC1 Expression in the Response to IL-6

Figure 2C:
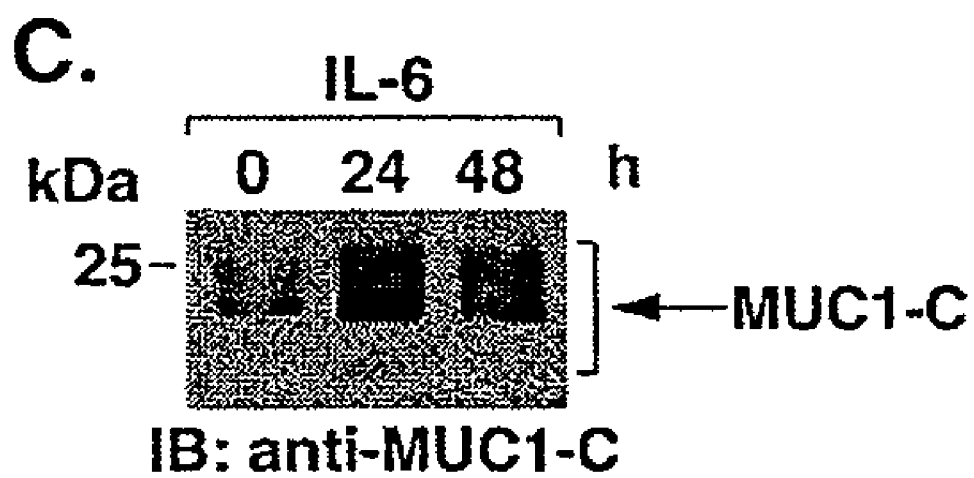
FIG. 2C is a photograph of an immunoblot depicting the induction of MUC1 expression following IL-6 treatment. MCF10A cells were treated without ("0") and with IL-6 (20 ng/mL) and then cultured at 37° C. for 24 ("24") and 48 ("48") hours. Cells were harvested at the indicated time points and lysed for western blot analysis. Whole-cell lysates were subjected to SDS-PAGE under reducing conditions and proteins were detected (immunoblotted, "IB") using antibodies specific for MUC1-C. The relative positions (e.g., the molecular weights) of the proteins are reported in kilodaltons (kDa) and indicated to the left of the immunoblot. "IL-6" indicates IL-6 treatment.

The inflammatory cytokine IL-6 activates STAT3 through the Janus kinases (JAKs) and has been linked to the development of cancer (Hodge et al. (2005) Eur. J. Cancer 41:2502-2512). Stimulation of MCF10A cells with IL-6 induces MUC1 expression (FIG. 2C). Moreover, the STAT3 binding site in the MUC1 promoter is located just downstream to the HSE and, could function alone or in concert with the HSE in activating MUC1 transcription (FIG. 1A). In this context, fever and inflammation activate both HSF1 and IL-6/STAT3 signaling pathways (Morimoto et al. (1998) Genes Dev. 12:3788-3796 and Hodge et al. (2005) Eur. J. Cancer 41:2502-2512).

To define the involvement of STAT3 activation in the regulation of MUC1 expression, the MCF10A and breast cancer cells are grown overnight in medium with 0.1% serum and then stimulated with 20 ng/mL IL-6 (R&D Systems, Minneapolis, Minn.). Since phosphorylation of STAT3 at tyrosine-705 leads to its activation, STAT3 activation is assessed by immunoblotting whole-cell lysates of the treated cells with anti-phospho-STAT3-Tyr-705 and anti-STAT3 (New England Biolabs) as a protein loading control. Lysates are also immunoblotted with anti-MUC1-N, anti-MUC1-C and anti-β-actin to assess induction of MUC1 expression. It is expected that treatment of cells with IL-6 will induce both STAT3 phosphorylation (activation) and MUC1 expression in MCF10A cells.

To determine if STAT3 is responsible for IL-6-induced increases in MUC1 expression, the cells are transfected with a STAT3 siRNA pool (Dharmacon) to silence STAT3 expression. At 36 h after transfection, the cells are treated with IL-6 and monitored for STAT3 and MUC1 levels by immunoblotting. A reduction or absence of IL-6-induced upregulation of MUC1 expression in cells lacking STAT3 would indicate that STAT3 is required for IL-6-induced MUC1 expression in MCF10A cells.

Example 3

Regulation of MUC1 Expression at the Transcriptional Level

Increases in MUC1 expression in MCF10A cells following HRG or IL-6 treatment could be due to, e.g., increased transcription of MUC1 mRNA, increased translation of MUC1 mRNA, and/or decreased degradation of MUC1 mRNA or protein. To determine if HRG and/or IL-6 upregulate MUC1 expression by activating MUC1 gene transcription, control and HRG- or IL-6-stimulated MCF10A cells are assayed for (i) MUC1 mRNA levels and (ii) activation of a MUC1 promoter-luciferase (pMUC1-Luc) reporter in cells transfected with the reporter construct (see below). To measure MUC1 mRNA levels, total cellular RNA is extracted in Trizol as described in Yin et al. (2003) J. Biol. Chem. 278:35458-35464. Reverse transcription polymerase chain reaction (RT-PCR) is then performed using the RNA with MUC1-specific primers (5'-TCTACTCTGGTGCACAACGG-3' (SEQ ID NO:6) and 5'-TTATATCGAGAGGCTGCTTCC-3' (SEQ ID NO: 7)) that span a region within genomic DNA that contains two introns, resulting in the amplification of a 489-bp fragment from RNA and a 738-bp fragment from genomic DNA. Primers for β-actin are used as a control (Yin et al. (2003) J. Biol. Chem. 278:35458-35464). The RNA is then reverse transcribed and amplified as described in Yin et al. (2003) J. Biol. Chem. 278:35458-35464. Amplified fragments are analyzed by electrophoresis in 2% agarose gels. To determine if the MUC1 promoter is activated by IL-6 or HRG, a fragment spanning the MUC1 promoter −686 to +31 was ligated into the firefly luciferase pG13-Basic vector (Abe et al. (1993) Proc. Natl. Acad. Sci. USA 90:282-286 and Yin et al. (2003) J. Biol. Chem. 278:35458-35464). Additional vectors can also be constructed that contain a mutated HSE and/or a mutated STAT3 binding site for use as controls. Cells are transfected with the pMUC1-Luc vectors and SV-40-*Renilla* (Promega, Madison, Wis.) in the presence of Lipofectamine for 14 hours. After washing and incubation for an additional 24 h, the cells are treated with heregulin (HRG) or IL-6 and harvested at intervals from 3 to 48 h. Lysates are analyzed for firefly and *Renilla* luciferase activities using the Dual Luciferase Reagent Assay Kit (Promega).

Increased MUC1 mRNA expression and MUC1 promoter activation in MCF10A cells treated with IL-6 or HRG would indicate that IL-6 and HRG induce MUC1 expression at the level of transcription.

Mutation of one or both of the HSE or STAT3 binding sites should decrease or prevent activation of the MUC1 promoter by HRG or IL-6, respectively. For example, the above reporter gene experiments can be performed with mutated MUC1 promoter sequences. Further experiments can be done to confirm the regulation of MUC1 transcription by HSE and STAT3 elements such as performing the pMUC1-Luc reporter assays on MCF10A cells transfected with HSF1 siRNA or STAT3 siRNA, which curtails the expression of HSF1 or STAT3, respectively. MCF10A cells which do not express HSF1 or STAT3 should have reduced or impaired MUC1 expression following treatment with HRG or STAT3 respectively. These results in totality will determine whether MUC1 gene transcription is activated in the response to (i) HRG through an HSF1-dependent mechanism, and/or (ii) IL-6 through a STAT3-dependent mechanism.

Example 4

Interaction Between MUC1-C and HSF1

Figure 3:
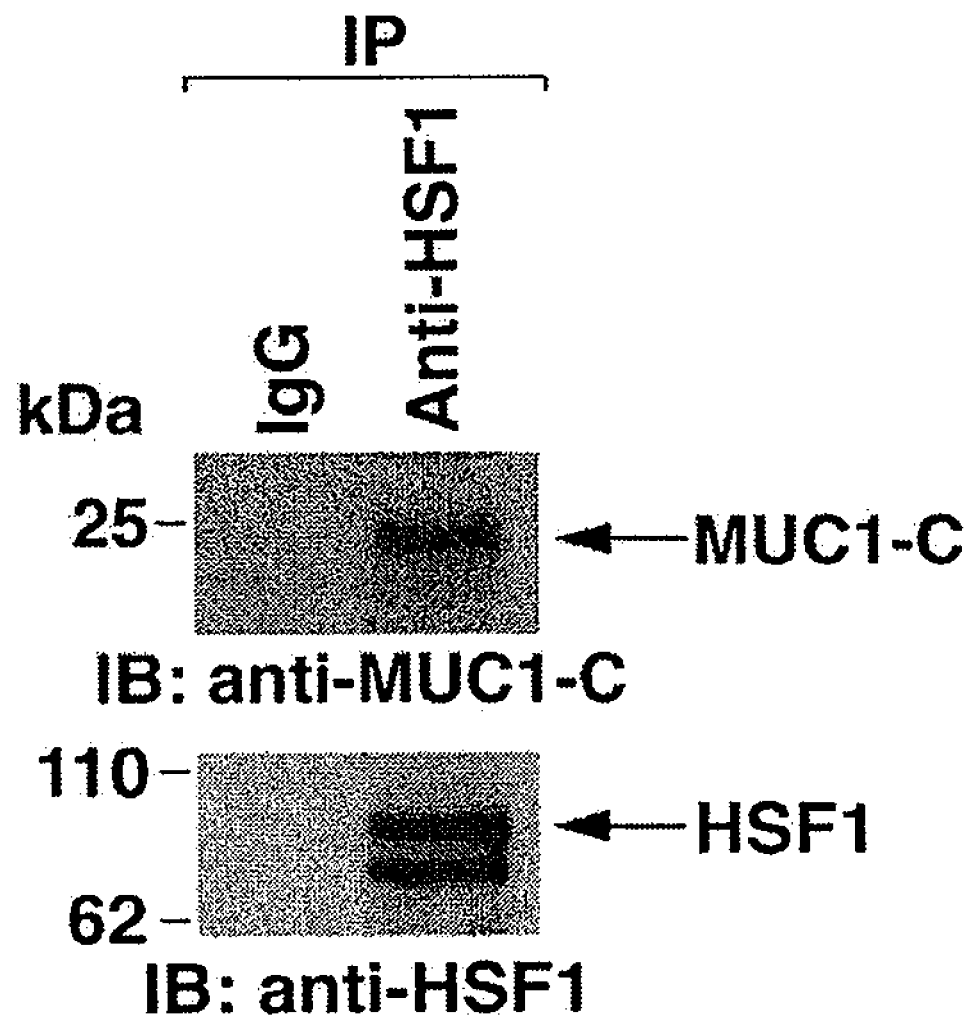
FIG. 3 is a pair of photographs of immunoblots depicting the in vivo association of MUC1 with HSF1. Whole-cell lysates were prepared from MCF10A cells and then subjected to immunoprecipation using antibodies specific for HSF1 ("anti-HSF") or an isotype non-specific antibody control ("IgG"). Immunoprecipitates were washed thoroughly, resuspended in Laemmli buffer and the immunoprecipitated proteins were resolved using SDS-PAGE. The various proteins were detected by western blot (immunoblot, "IB") using antibodies specific for MUC1-C and HSF1 (top and bottom photographs, respectively). The relative positions (e.g., the molecular weights) of the proteins are reported in kilodaltons (kDa) and indicated to the left of each of the immunoblots (e.g., 25 kDa or 110 kDa). "IP" indicates immunoprecipitation.

MUC1-C binds directly to β-catenin and coactivates the induction of β-catenin/Tcf target genes (Huang et al. (2003) Cancer Biol. Ther. 2:702-706). To determine if MUC1-C associates with HSF1, a coimmunoprecipitation experiment was performed using MCF-7 cell lysates and an antibody specific for MUC1. Immunoprecipitates were subjected to SDS-PAGE and immunoblotted with antibodies specific for MUC1 and HSF1 proteins. MUC1-C co-immunoprecipitated with HSF1 in MCF-7 cells (FIG. 3). These results indicated that MUC1 binds to HSF1.

One possibility is that HSF1 induces MUC1 expression and, in an autoregulatory loop, MUC1-C binds to HSF1 and coactivates HSF1-mediated transcription. To determine if the association between MUC1-C and HSF1 is regulated by HRG, whole-cell lysates from control and HRG-treated MCF10A cells will be subjected to anti-MUC1-C or anti-HSF1 antibodies to immunoprecipitate MUC1-C and HSF1, respectively. The precipitates will be immunoblotted using antibodies specific for MUC1-C and HSF1. As a control, the cells can be subjected to heat shock and then assayed (as above) for coimmunoprecipitation of MUC1-C and HSF1. HRG treatment of MCF10A cells should lead to increased association between MUC1 and HSF1. These results would provide further evidence for the above-mentioned autoregulatory model.

To determine if HRG treatment increases complex formation in breast cancer cells, MCF7 cells are treated with HRG followed by lysis and immunoprecipitation using antibodies specific for MUC1-C and HSF1 (as described above). While HRG treatment promotes complex formation in normal breast cells (MCF10A), it is expected that HRG would have less of an effect on this interaction in breast cancer cells and thus indicate that cancer cells have constitutive MUC1-HSF1 complex assembly.

The binding of MUC1 to HSF1 could be direct or indirect, for example, through a third protein. To determine if the interaction between MUC1 and HSF1 is a direct, physical interaction, in vitro binding assays are performed. GST- and GST-HSF1 (as described in Wang et al. (2006) J. Biol. Chem. 281:782-791) polypeptides are incubated with purified His-tagged MUC1-CD as described in Li et al. (1998) Mol. Cell. Biol. 18:7216-7224. The protein mixtures are then incubated with glutathione beads, which bind to the GST proteins and associated binding partners if present. The glutathione bead adsorbates are washed and immunoblotted with antibodies specific for His tags or to MUC1-C (as described above). His-tagged MUC1 is expected to be present in GST-HSF1 adsorbates but not GST-adsorbates. These results would indicate that MUC1 and HSF1 bind directly.

HSF1 contains a DNA binding domain, an adjacent hydrophobic repeat (HR-A/B) essential for trimer formation, a regulatory domain and an activation domain (FIG. 4A). To determine which region(s) of HSF1 protein binds to MUC1, similar binding studies can be performed with GST-tagged fragments of HSF1 (e.g., GST-tagged HSF1-DNA binding domain proteins) to define the region of HSF1 that interacts with MUC1-CD. Exemplary methods for generating such GST-tagged proteins are known in the art.

In addition, GST, GST-MUC1-CD(1-45) or GST-MUC1-CD(46-72) will be incubated with purified recombinant HSF1 (Stressgen (Nventa) San Diego, Calif.) to determine which region of MUC1-CD binds to HSF1. The adsorbates can also be immunoblotted with an anti-HSF1 antibody.

Example 5

Interaction Between MUC1-C and STAT3

To determine if MUC1-C associates with STAT3, a coimmunoprecipitation experiment was performed using MCF-7 cell lysates and an antibody specific for MUC1. Immunoprecipitates were subjected to SDS-PAGE and immunoblotted with antibodies specific for MUC1 and HSF1 proteins. MUC1-C co-immunoprecipitated with STAT3 in MCF-7 cells. These results indicated that MUC1 binds to STAT3.

The binding of MUC1 to HSF1 could be direct or indirect, for example, through a third protein. To determine if the interaction between MUC1 and HSF1 is a direct, physical interaction, in vitro binding assays was performed. GST- and GST-STAT3 polypeptides were incubated with purified His-tagged MUC1-CD (similar to GST-HSF1-His-MUC1 experiments described above). The protein mixtures were then incubated with glutathione beads, which bind to the GST proteins and associated binding partners if present. The glutathione bead adsorbates were washed and immunoblotted with antibodies specific for His tags or to MUC1-C (as described above). His-tagged MUC1 was present in GST-STAT3 adsorbates but not GST-adsorbates. These results indicated that MUC1 and STAT3 bind directly.

STAT3 contains, inter alia, a dimerization domain and a DNA binding domain. To determine which region(s) of STAT3 protein binds to MUC1, similar binding studies are performed with GST-tagged fragments of STAT3 (e.g., GST-tagged STAT3-DNA binding domain proteins) to define the region of STAT3 that interacts with MUC1-CD. Exemplary methods for generating such GST-tagged proteins are known in the art. In addition, GST, GST-MUC1-CD(1-45) or GST-MUC1-CD(46-72) are incubated with purified recombinant STAT3 to determine which region of MUC1-CD binds to STAT3. The adsorbates are also immunoblotted with an anti-STAT3 antibody.

Example 6

HSF1/STAT3 Occupancy of the MUC1 Promoter

Transcriptional activation of the MUC1 gene is of importance to the overexpression of MUC1 in human breast cancers. It is possible that HSF1 and STAT3 occupy the MUC1 promoter in the response of normal cells (e.g., non cancer cells, e.g., MCF10A cells) to HRG and IL-6, respectively, and (ii) HSF1 and/or STAT3 constitutively occupy the MUC1 promoter in breast cancer cells.

To study if HSF1 and/or STAT3 occupies the MUC1 promoter, ChIP assays are performed as described in Wei et al. (2006) Mol. Cell. 21:295-305. MCF10A cells are treated with IL-6 or HRG as described above followed by treatment with 1% formaldehyde to cross-link proteins to DNA and then lysates are prepared by sonication. Soluble chromatin from control and HRG- or IL-6-treated cells are immunoprecipitated with anti-HSF1, anti-STAT3 antibodies or a control IgG. The final DNA extractions are amplified by PCR using primers that cover the HSE (−841 to −620; 5'-GGCTCTGCTGC-CTCACTTAG-3' (SEQ ID NO:8) and 3'-CTTTCTCCAAG-GAGGGAACC-5' (SEQ ID NO:9)), the STAT3 binding site (−521 to −310; 5'-TAGAAGGGTGGGGCTATTCC-3'(SEQ ID NO:10) and 3'-TTAGTTGTTGCCCTGAGGCT-5'(SEQ ID NO:11)) and a control region (CR: −1686 to −1548; 5'-GTCTTGGGGCTGAGAACTG-3' (SEQ ID NO:12) and 3'-GCACACACCTCTTGGCTGT-5' (SEQ ID NO:13)). For PCR, 2 µl of a 50 µl DNA extraction is used with 30-38 cycles of PCR amplification. It is expected that following IL-6 or HRG treatment of MCF10A cells, an increased association of STAT3 and HSF1 respectively with the MUC1 promoter should be detected by PCR of associated chromatin. Such results would indicate that IL-6 and HRG induce the binding of STAT3 and HSF1 to the MUC1 promoter and thereby promote its expression.

The CREB binding protein (CBP) functions as a histone acetyltransferase and thereby a co-activator of gene transcription. By contrast, recruitment of the HDAC1 histone deacetylase represses gene transcription. To determine if HSF1 occupancy of the MUC1 promoter affects recruitment of CBP and HDAC1, re-ChIP assays are performed as described in Wei et al. (2005) Cancer Cell 7:167-178 and Wei et al. (2006) Mol. Cell. 21:295-305. In brief, soluble chromatin is immunoprecipitated with anti-HSF1 or anti-STAT3, eluted with DTT, diluted with re-ChIP buffer and immunoprecipitated further with anti-CBP (Santa Cruz Biotechnology) or anti-HDAC1 antibodies (Upstate Biotechnology Inc. (Millipore), Charlotteville, Va.). The final DNA extractions are then amplified by PCR using primers that cover the HSE, the STAT3 binding site and the control region (CR) (see above). It is expected that HSF1 and/or STAT3 occupancy of the MUC1 promoter will be associated with recruitment of CBP and not HDAC1. As an additional test for such a mechanism, the HSF1 and/or STAT3 binding motifs can be tested for an increase in histone H4 acetylation by performing ChIP assays with an antibody against acetylated H4 (anti-Ac-H4; Upstate Biotechnology Inc.) (as above).

Next, to determine whether MUC1-C associates with the HSE of the MUC1 promoter, ChIP assays are performed on control and HRG-treated cells (as described above). Soluble chromatin is immunoprecipitated with anti-MUC1-C or a control IgG. The precipitates are then analyzed for MUC1-C occupancy of the HSE and control region by PCR. The presence fo HSE of the MUC1 promoter DNA in anti-MUC1 immunoprecipitates (as assayed by PCR) would indicate that MUC1 associates with the HSE of the MUC1 promoter.

To determine if MUC1-C occupies the MUC1 promoter with HSF1, the anti-MUC1-C ChIPs are eluted with dithiothreitol (DTT) diluted with re-ChIP buffer and reimmunoprecipitated with anti-HSF1 before analysis by PCR (as described above). The presence of HSE of the MUC1 promoter anti-HSF1 reimmunoprecipates (as assessed by PCR) would indicate that both HSE and MUC1 occupy a region of the MUC1 promoter containing the HSE.

It is possible that MUC1-C will occupy the MUC1 promoter with HSF1 following stimulation of MCF10A breast cells with HRG and constitutively in breast cancer cells. To determine if MUC1-C binds to the MUC1 promoter in response to HRG stimulation, MCF10A cells are cultured in low serum and then stimulated with HRG as described above. ChIP assays are performed on cells with and without HRG treatment and the level of MUC1 associated with the MUC1 promoter is assessed, e.g., using quantitative PCR. Increased MUC1 association with MUC1 promoter will be observed following HRG treatment as compared to without HRG treatment. Such results would indicate that HRG stimulates the association of MUC1 with the MUC1 promoter. Similar ChIP experiments are performed in MCF7 breast cancer cells. The observation of little or no change in high basal levels of MUC1 association with the MUC1 promoter in MCF7 cells would indicate that MUC1 association with the MUC1 promoter is consititutive in breast cancer cells.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by this application.

What is claimed is:

1. A method of identifying a compound that inhibits the binding of MUC1 to STAT3, the method comprising:
    (a) contacting a MUC1 reagent comprising SEQ ID NO:2 with a STAT3 reagent comprising SEQ ID NO:5 in the presence of a candidate compound; and
    (b) determining whether the candidate compound inhibits binding of the MUC1 reagent to the STAT3 reagent.

* * * * *

UNITED STATES PATENT AND TRADEMARK OFFICE
CERTIFICATE OF CORRECTION

PATENT NO.         : 7,972,870 B2                                              Page 1 of 1
APPLICATION NO.    : 12/024692
DATED              : July 5, 2011
INVENTOR(S)        : Donald W. Kufe It is certified that error appears in the above-identified patent and that said Letters Patent is hereby corrected as shown below:

In column 1, lines 9-12, delete paragraph and insert
--This invention was made with government support under grant no. CA97098 awarded by the National Cancer Institute of the National Institutes of Health. The government has certain rights in the invention.-- therefor.

Signed and Sealed this
Twenty-seventh Day of September, 2011

David J. Kappos
*Director of the United States Patent and Trademark Office*

SEQUENCE LISTING

```
<160> NUMBER OF SEQ ID NOS: 16

<210> SEQ ID NO 1
<211> LENGTH: 203
<212> TYPE: PRT
<213> ORGANISM: Homo sapiens

<400> SEQUENCE: 1

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30
```

```
Gly Glu Lys Glu Thr Ser Ala Thr Gln Arg Ser Ser Val Pro Ser Ser
            35                  40                  45
Thr Glu Lys Asn Ala Ile Pro Ala Pro Thr Thr Thr Lys Ser Cys Arg
        50                  55                  60
Glu Thr Phe Leu Lys Cys Phe Cys Arg Phe Ile Asn Lys Gly Val Phe
65                  70                  75                  80
Trp Ala Ser Pro Ile Leu Ser Ser Val Ser Asp Val Pro Phe Pro Phe
                85                  90                  95
Ser Ala Gln Ser Gly Ala Gly Val Pro Gly Trp Gly Ile Ala Leu Leu
            100                 105                 110
Val Leu Val Cys Val Leu Val Ala Leu Ala Ile Val Tyr Leu Ile Ala
        115                 120                 125
Leu Ala Val Cys Gln Cys Arg Arg Lys Asn Tyr Gly Gln Leu Asp Ile
130                 135                 140
Phe Pro Ala Arg Asp Thr Tyr His Pro Met Ser Glu Tyr Pro Thr Tyr
145                 150                 155                 160
His Thr His Gly Arg Tyr Val Pro Pro Ser Ser Thr Asp Arg Ser Pro
                165                 170                 175
Tyr Glu Lys Val Ser Ala Gly Asn Gly Gly Ser Ser Leu Ser Tyr Thr
            180                 185                 190
Asn Pro Ala Val Ala Ala Thr Ser Ala Asn Leu
            195                 200

<210> SEQ ID NO 2
<211> LENGTH: 72
<212> TYPE: PRT
<213> ORGANISM: Homo sapiens

<400> SEQUENCE: 2

Cys Gln Cys Arg Arg Lys Asn Tyr Gly Gln Leu Asp Ile Phe Pro Ala
1               5                   10                  15
Arg Asp Thr Tyr His Pro Met Ser Glu Tyr Pro Thr Tyr His Thr His
            20                  25                  30
Gly Arg Tyr Val Pro Pro Ser Ser Thr Asp Arg Ser Pro Tyr Glu Lys
        35                  40                  45
Val Ser Ala Gly Asn Gly Gly Ser Ser Leu Ser Tyr Thr Asn Pro Ala
    50                  55                  60
Val Ala Ala Ala Ser Ala Asn Leu
65                  70

<210> SEQ ID NO 3
<211> LENGTH: 1725
<212> TYPE: DNA
<213> ORGANISM: Homo sapiens

<400> SEQUENCE: 3
gcttccgtgc gcctagagcg cagcctgcga ctgcgggacc caacaaccac gtgctgccgc    60
ggcctgggat agcttcctcc cctctggcac tgctgccgca cacacctctt ggctgtcgcg   120
cattacgcac ctcacgtgtg cttttgcccc cgcctacgtg cctacctgtc cccaatacca   180
ctctgctccc caaaggatag ttctgtgtcc gtaaatccca ttctgtcacc ccacctactc   240
tctgcccccc ccttttttgt tttgagacgg agtcttgctc tgtcgcccag gctggagtgc   300
aatggcgcga tctcggctca ctgcaacctc cgcctcccgg gttcaagcga ttctcctgcc   360
tcagcctcct gagtagctgg ggttacagcc ccgccaccac cgtcggcta atttttgtag   420 tttttagtag agacgaggtt tcaccatctt ggccaggctg tcttgaacc cctgaccttg   480
```

-continued

```
tgatccactc gcctcggcct tccaaagtgt tgggattacg ggcgtgacga ccgtgccacg    540
cccgatctgc ctcttaagta cataacggcc cacacagaac gtgtccaact cccccgccca    600
cgttccaacg tcctctccca catacctcgg tgcccttcc acatacctca ggaccccacc     660
cgcttagctc catttcctcc agacgccacc accacgcgtc ccggagtgcc cctcctaaa     720 gctcccagcc gtccaccatg ctgtgcgttc ctccctccct ggccacggca gtgacccttc    780
tctcccgggc cctgcttccc tctcgcgggc tctcgctgcc tcacttaagc agcgctgccc    840
ttactcctct ccgcccggtc cgagcggccc ctcagcttgc gcggcccagc ccgcaaggc     900 tcccggtgac cactagaggg cgggaggagc tcctggccag tggtggagag tggcaaggaa    960
ggaccctagg gttcatcgga gcccaggttt actcccttaa gtggaaattt cttcccccac   1020
tccctccttg gctttctcca aggagggaac ccaggctgct ggaaagtccg gctgggcgg    1080 ggactgtggg tttcagggta gaactgcgtg tggaacggga cagggagcgg ttagaagggt   1140
ggggctattc cgggaagtgg tgggggagg gagcccaaaa ctagcaccta gtccactcat    1200
tatccagccc tcttatttct cggccccgct ctgcttcagt ggacccgggg agggcgggga   1260
agtggagtgg gagacctagg ggtgggcttc ccgaccttgc tgtacaggac ctcgacctag   1320
ctggctttct tccccatccc cacgttagtt gttgccctga ggctaaaact agagcccagg   1380
ggccccaagt tccagactgc ccctccccc tccccggag ccaggagtg gttggtgaaa     1440 gggggaggcc agctggagaa caaacgggta gtcagggggt tgagcgatta gagcccttgt   1500
accctaccca ggaatggttg gggaggagga ggaagaggta ggaggtaggg gaggggcgg    1560 ggttttgtca cctgtcacct gctccggctg tgcctagggc gggcgggcgg ggagtggggg   1620
gaccggtata aagcggtagg cgcctgtgcc cgctccacct tcaagcagc cagcgcctgc    1680 ctgaatctgt tctgccccct ccccacccat ttcaccacca ccatg                   1725
```

<210> SEQ ID NO 4
<211> LENGTH: 10
<212> TYPE: DNA
<213> ORGANISM: Homo sapiens

<400> SEQUENCE: 4
ggaaatttct                                                            10

<210> SEQ ID NO 5
<211> LENGTH: 192
<212> TYPE: PRT
<213> ORGANISM: Homo sapiens

<400> SEQUENCE: 5

Met Asp Gly Ser Gly Glu Gln Pro Arg Gly Gly Pro Thr Ser Ser
1               5                   10                  15

Glu Gln Ile Met Lys Thr Gly Ala Leu Leu Leu Gln Gly Phe Ile Gln
                20                  25                  30

Asp Arg Ala Gly Arg Met Gly Gly Glu Ala Pro Glu Leu Ala Leu Asp
            35                  40                  45

Pro Val Pro Gln Asp Ala Ser Thr Lys Lys Leu Ser Glu Cys Leu Lys
        50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95

Ala Asp Met Phe Ser Asp Gly Asn Phe Asn Trp Gly Arg Val Val Ala
                100                 105                 110

```
Leu Phe Tyr Phe Ala Ser Lys Leu Val Leu Lys Ala Leu Cys Thr Lys
            115                 120                 125

Val Pro Glu Leu Ile Arg Thr Ile Met Gly Trp Thr Leu Asp Phe Leu
        130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190

<210> SEQ ID NO 6
<211> LENGTH: 20
<212> TYPE: DNA
<213> ORGANISM: Homo sapiens

<400> SEQUENCE: 6
tctactctgg tgcacaacgg                                             20

<210> SEQ ID NO 7
<211> LENGTH: 21
<212> TYPE: DNA
<213> ORGANISM: Homo sapiens

<400> SEQUENCE: 7
ttatatcgag aggctgcttc c                                           21

<210> SEQ ID NO 8
<211> LENGTH: 20
<212> TYPE: DNA
<213> ORGANISM: Homo sapiens

<400> SEQUENCE: 8
ggctctgctg cctcacttag                                             20

<210> SEQ ID NO 9
<211> LENGTH: 20
<212> TYPE: DNA
<213> ORGANISM: Homo sapiens

<400> SEQUENCE: 9
ctttctccaa ggagggaacc                                             20

<210> SEQ ID NO 10
<211> LENGTH: 20
<212> TYPE: DNA
<213> ORGANISM: Homo sapiens

<400> SEQUENCE: 10
tagaagggtg gggctattcc                                             20

<210> SEQ ID NO 11
<211> LENGTH: 20
<212> TYPE: DNA
<213> ORGANISM: Homo sapiens

<400> SEQUENCE: 11
ttagttgttg ccctgaggct                                             20

<210> SEQ ID NO 12
<211> LENGTH: 19
<212> TYPE: DNA
```

-continued

<213> ORGANISM: Homo sapiens

<400> SEQUENCE: 12
gtcttggggc tgagaactg                                                   19

<210> SEQ ID NO 13
<211> LENGTH: 19
<212> TYPE: DNA
<213> ORGANISM: Homo sapiens

<400> SEQUENCE: 13
gcacacacct cttggctgt                                                   19

<210> SEQ ID NO 14
<211> LENGTH: 529
<212> TYPE: PRT
<213> ORGANISM: Homo sapiens

<400> SEQUENCE: 14

```
Met Asp Leu Pro Val Gly Pro Gly Ala Ala Gly Pro Ser Asn Val Pro
1               5                   10                  15

Ala Phe Leu Thr Lys Leu Trp Thr Leu Val Ser Asp Pro Asp Thr Asp
            20                  25                  30

Ala Leu Ile Cys Trp Ser Pro Ser Gly Asn Ser Phe His Val Phe Asp
        35                  40                  45

Gln Gly Gln Phe Ala Lys Glu Val Leu Pro Lys Tyr Phe Lys His Asn
    50                  55                  60

Asn Met Ala Ser Phe Val Arg Gln Leu Asn Met Tyr Gly Phe Arg Lys
65                  70                  75                  80

Val Val His Ile Glu Gln Gly Gly Leu Val Lys Pro Glu Arg Asp Asp
                85                  90                  95

Thr Glu Phe Gln His Pro Cys Phe Leu Arg Gly Gln Glu Gln Leu Leu
            100                 105                 110

Glu Asn Ile Lys Arg Lys Val Thr Ser Val Ser Thr Leu Lys Ser Glu
        115                 120                 125

Asp Ile Lys Ile Arg Gln Asp Ser Val Thr Lys Leu Leu Thr Asp Val
    130                 135                 140

Gln Leu Met Lys Gly Lys Gln Glu Cys Met Asp Ser Lys Leu Leu Ala
145                 150                 155                 160

Met Lys His Glu Asn Glu Ala Leu Trp Arg Glu Val Ala Ser Leu Arg
                165                 170                 175

Gln Lys His Ala Gln Gln Lys Val Val Asn Lys Leu Ile Gln Phe
            180                 185                 190

Leu Ile Ser Leu Val Gln Ser Asn Arg Ile Leu Gly Val Lys Arg Lys
        195                 200                 205

Ile Pro Leu Met Leu Asn Asp Ser Gly Ser Ala His Ser Met Pro Lys
    210                 215                 220

Tyr Ser Arg Gln Phe Ser Leu Glu His Val His Gly Ser Gly Pro Tyr
225                 230                 235                 240

Ser Ala Pro Ser Pro Ala Tyr Ser Ser Ser Leu Tyr Ala Pro Asp
                245                 250                 255

Ala Val Ala Ser Ser Gly Pro Ile Ile Ser Asp Ile Thr Glu Leu Ala
            260                 265                 270

Pro Ala Ser Pro Met Ala Ser Pro Gly Gly Ser Ile Asp Glu Arg Pro
        275                 280                 285

Leu Ser Ser Ser Pro Leu Val Arg Val Lys Glu Glu Pro Pro Ser Pro
    290                 295                 300
```

```
Pro Gln Ser Pro Arg Val Glu Ala Ser Pro Gly Arg Pro Ser Ser
305                 310                 315                 320

Val Asp Thr Leu Leu Ser Pro Thr Ala Leu Ile Asp Ser Ile Leu Arg
            325                 330                 335

Glu Ser Glu Pro Ala Pro Ala Ser Val Thr Ala Leu Thr Asp Ala Arg
            340                 345                 350

Gly His Thr Asp Thr Glu Gly Arg Pro Pro Ser Pro Pro Pro Thr Ser
            355                 360                 365

Thr Pro Glu Lys Cys Leu Ser Val Ala Cys Leu Asp Lys Asn Glu Leu
    370                 375                 380

Ser Asp His Leu Asp Ala Met Asp Ser Asn Leu Asp Asn Leu Gln Thr
385                 390                 395                 400

Met Leu Ser Ser His Gly Phe Ser Val Asp Thr Ser Ala Leu Leu Asp
                405                 410                 415

Leu Phe Ser Pro Ser Val Thr Val Pro Asp Met Ser Leu Pro Asp Leu
            420                 425                 430

Asp Ser Ser Leu Ala Ser Ile Gln Glu Leu Leu Ser Pro Gln Glu Pro
        435                 440                 445

Pro Arg Pro Pro Glu Ala Glu Asn Ser Ser Pro Asp Ser Gly Lys Gln
    450                 455                 460

Leu Val His Tyr Thr Ala Gln Pro Leu Phe Leu Leu Asp Pro Gly Ser
465                 470                 475                 480

Val Asp Thr Gly Ser Asn Asp Leu Pro Val Leu Phe Glu Leu Gly Glu
                485                 490                 495

Gly Ser Tyr Phe Ser Glu Gly Asp Gly Phe Ala Glu Asp Pro Thr Ile
            500                 505                 510

Ser Leu Leu Thr Gly Ser Glu Pro Pro Lys Ala Lys Asp Pro Thr Val
            515                 520                 525

Ser
```

```
<210> SEQ ID NO 15
<211> LENGTH: 770
<212> TYPE: PRT
<213> ORGANISM: Homo sapiens

<400> SEQUENCE: 15

Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
            20                  25                  30

Phe Leu Ala Pro Trp Ile Glu Ser Gln Asp Trp Ala Tyr Ala Ala Ser
        35                  40                  45

Lys Glu Ser His Ala Thr Leu Val Phe His Asn Leu Leu Gly Glu Ile
    50                  55                  60

Asp Gln Gln Tyr Ser Arg Phe Leu Gln Glu Ser Asn Val Leu Tyr Gln
65                  70                  75                  80

His Asn Leu Arg Arg Ile Lys Gln Phe Leu Gln Ser Arg Tyr Leu Glu
                85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
        115                 120                 125

Ala Asn His Pro Thr Ala Ala Val Val Thr Glu Lys Gln Gln Met Leu
    130                 135                 140
```

-continued

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
            165                 170                 175

Lys Thr Leu Lys Ser Gln Gly Asp Met Gln Asp Leu Asn Gly Asn Asn
        180                 185                 190

Gln Ser Val Thr Arg Gln Lys Met Gln Gln Leu Glu Gln Met Leu Thr
    195                 200                 205

Ala Leu Asp Gln Met Arg Arg Ser Ile Val Ser Glu Leu Ala Gly Leu
210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln
        275                 280                 285

Gln Lys Val Ser Tyr Lys Gly Asp Pro Ile Val Gln His Arg Pro Met
290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
            340                 345                 350

Val Lys Phe Pro Glu Leu Asn Tyr Gln Leu Lys Ile Lys Val Cys Ile
        355                 360                 365

Asp Lys Asp Ser Gly Asp Val Ala Ala Leu Arg Gly Ser Arg Lys Phe
370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
            420                 425                 430

Thr Glu Glu Leu His Leu Ile Thr Phe Glu Thr Glu Val Tyr His Gln
        435                 440                 445

Gly Leu Lys Ile Asp Leu Glu Thr His Ser Leu Pro Val Val Val Ile
450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
        515                 520                 525

Ala Glu Lys Leu Leu Gly Pro Gly Val Asn Tyr Ser Gly Cys Gln Ile
530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

-continued

```
Leu Ala Leu Trp Asn Glu Gly Tyr Ile Met Gly Phe Ile Ser Lys Glu
                580                 585                 590

Arg Glu Arg Ala Ile Leu Ser Thr Lys Pro Pro Gly Thr Phe Leu Leu
                595                 600                 605

Arg Phe Ser Glu Ser Ser Lys Glu Gly Gly Val Thr Phe Thr Trp Val
            610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
                660                 665                 670

Leu Tyr Pro Asp Ile Pro Lys Glu Glu Ala Phe Gly Lys Tyr Cys Arg
                675                 680                 685

Pro Glu Ser Gln Glu His Pro Glu Ala Asp Pro Gly Ser Ala Ala Pro
            690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
            740                 745                 750

Glu Ser Leu Thr Phe Asp Met Glu Leu Thr Ser Glu Cys Ala Thr Ser
                755                 760                 765

Pro Met
770

<210> SEQ ID NO 16
<211> LENGTH: 296
<212> TYPE: PRT
<213> ORGANISM: Homo sapiens

<400> SEQUENCE: 16

Met Glu Ile Tyr Ser Pro Asp Met Ser Glu Val Ala Ala Glu Arg Ser
1               5                   10                  15

Ser Ser Pro Ser Thr Gln Leu Ser Ala Asp Pro Ser Leu Asp Gly Leu
                20                  25                  30

Pro Ala Ala Glu Asp Met Pro Glu Pro Gln Thr Glu Asp Gly Arg Thr
            35                  40                  45

Pro Gly Leu Val Gly Leu Ala Val Pro Cys Cys Ala Cys Leu Glu Ala
        50                  55                  60

Glu Arg Leu Arg Gly Cys Leu Asn Ser Glu Lys Ile Cys Ile Val Pro
65                  70                  75                  80

Ile Leu Ala Cys Leu Val Ser Leu Cys Leu Cys Ile Ala Gly Leu Lys
                85                  90                  95

Trp Val Phe Val Asp Lys Ile Phe Glu Tyr Asp Ser Pro Thr His Leu
                100                 105                 110

Asp Pro Gly Gly Leu Gly Gln Asp Pro Ile Ile Ser Leu Asp Ala Thr
            115                 120                 125

Ala Ala Ser Ala Val Trp Val Ser Ser Glu Ala Tyr Thr Ser Pro Val
        130                 135                 140

Ser Arg Ala Gln Ser Glu Ser Glu Val Gln Val Thr Val Gln Gly Asp
145                 150                 155                 160

Lys Ala Val Val Ser Phe Glu Pro Ser Ala Ala Pro Thr Pro Lys Asn
                165                 170                 175
```

```
Arg Ile Phe Ala Phe Ser Phe Leu Pro Ser Thr Ala Pro Ser Phe Pro
            180                 185                 190

Ser Pro Thr Arg Asn Pro Glu Val Arg Thr Pro Lys Ser Ala Thr Gln
        195                 200                 205

Pro Gln Thr Thr Glu Thr Asn Leu Gln Thr Ala Pro Lys Leu Ser Thr
        210                 215                 220

Ser Thr Ser Thr Thr Gly Thr Ser His Leu Val Lys Cys Ala Glu Lys
225                 230                 235                 240

Glu Lys Thr Phe Cys Val Asn Gly Gly Glu Cys Phe Met Val Lys Asp
            245                 250                 255

Leu Ser Asn Pro Ser Arg Tyr Leu Cys Lys Cys Pro Asn Glu Phe Thr
            260                 265                 270

Gly Asp Arg Cys Gln Asn Tyr Val Met Ala Ser Phe Tyr Ser Thr Ser
            275                 280                 285

Thr Pro Phe Leu Ser Leu Pro Glu
    290                 295
```